United States Patent
Khvorova et al.

(10) Patent No.: US 12,180,477 B2
(45) Date of Patent: Dec. 31, 2024

(54) DYNAMIC PHARMACOKINETIC-MODIFYING ANCHORS

(71) Applicant: UNIVERSITY OF MASSACHUSETTS, Boston, MA (US)

(72) Inventors: Anastasia Khvorova, Westborough, MA (US); Bruno Miguel da Cruz Godinho, Worcester, MA (US); Matthew Hassler, Worcester, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 0 days.

(21) Appl. No.: 17/725,102

(22) Filed: Apr. 20, 2022

(65) Prior Publication Data

US 2022/0372476 A1 Nov. 24, 2022

Related U.S. Application Data

(62) Division of application No. 16/746,555, filed on Jan. 17, 2020, now Pat. No. 11,492,619.

(60) Provisional application No. 62/794,123, filed on Jan. 18, 2019.

(51) Int. Cl.
C12N 15/113 (2010.01)

(52) U.S. Cl.
CPC ........ *C12N 15/113* (2013.01); *C12N 2310/11* (2013.01); *C12N 2310/14* (2013.01); *C12N 2310/314* (2013.01); *C12N 2310/315* (2013.01); *C12N 2310/3181* (2013.01); *C12N 2310/321* (2013.01); *C12N 2310/322* (2013.01); *C12N 2310/3231* (2013.01); *C12N 2310/351* (2013.01); *C12N 2310/3513* (2013.01); *C12N 2310/3515* (2013.01); *C12N 2310/531* (2013.01); *C12N 2320/32* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,194,596 A | 3/1993 | Tischer et al. |
| 5,219,739 A | 6/1993 | Tischer et al. |
| 5,240,848 A | 8/1993 | Keck et al. |
| 5,328,470 A | 7/1994 | Nabel et al. |
| 5,332,671 A | 7/1994 | Ferrara et al. |
| 5,684,143 A | 11/1997 | Grayaznov et al. |
| 5,814,014 A | 9/1998 | Elsberry et al. |
| 5,858,988 A | 1/1999 | Wang |
| 5,939,402 A | 8/1999 | Weis et al. |
| 6,025,335 A | 2/2000 | Weis et al. |
| 6,093,180 A | 7/2000 | Elsberry et al. |
| 6,107,094 A | 8/2000 | Crooke |
| 6,168,587 B1 | 1/2001 | Bellhouse et al. |
| 6,177,403 B1 | 1/2001 | Stedman |
| 6,194,389 B1 | 2/2001 | Johnston et al. |
| 6,291,438 B1 | 9/2001 | Wang |
| 6,312,900 B1 | 11/2001 | Dean et al. |
| 6,383,814 B1 | 5/2002 | Lee et al. |
| 6,447,768 B1 | 9/2002 | van Zonneveld et al. |
| 6,471,996 B1 | 10/2002 | Sokoll et al. |
| 6,472,375 B1 | 10/2002 | Hoon et al. |
| 6,489,464 B1 | 12/2002 | Agrawal et al. |
| 7,250,496 B2 | 7/2007 | Bentwich |
| 7,459,547 B2 | 12/2008 | Zamore et al. |
| 7,691,997 B2 | 4/2010 | Khvorova et al. |
| 7,723,512 B2 | 5/2010 | Manoharan et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 7,790,867 B2 | 9/2010 | Bentwich |
| 7,834,171 B2 | 11/2010 | Leake et al. |
| 8,013,136 B2 | 9/2011 | Manoharan et al. |
| 8,097,752 B2 | 1/2012 | Calogeropolou et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 8,431,544 B1 | 4/2013 | Agrawal et al. |
| 8,501,706 B2 | 8/2013 | Yamada et al. |
| 8,507,661 B2 | 8/2013 | Manoharan et al. |
| 8,664,189 B2 | 3/2014 | Khvorova et al. |

(Continued)

FOREIGN PATENT DOCUMENTS

| | | |
|---|---|---|
| CN | 101199858 A | 6/2008 |
| CN | 101365801 A | 2/2009 |

(Continued)

OTHER PUBLICATIONS

U.S. Appl. No. 15/089,319 2016/0355808 U.S. Pat. No. 9,809,817, filed Apr. 1, 2016 Dec. 8, 2016 Nov. 7, 2017, Anastasia Khvorova, Oligonucleotide Compounds for Targeting Huntingtin mRNA.
U.S. Appl. No. 15/697,120 2018/0094263 U.S. Pat. No. 10,435,688, filed Sep. 6, 2017 Apr. 5, 2018 Oct. 8, 2019, Anastasia Khvorova, Oligonucleotide Compounds for Targeting Huntingtin mRNA.
U.S. Appl. No. 16/263,200 2019/0225965 U.S. Pat. No. 10,744,327, filed Jan. 31, 2019 Jul. 25, 2019 Sep. 15, 2020, Anastasia Khvorova, Oligonucleotide Compounds for Targeting Huntingtin mRNA.
U.S. Appl. No. 16/811,580 2020/0308584 U.S. Pat. No. 11,230,713, filed Mar. 6, 2020 Oct. 1, 2020 Jan. 5, 2022, Anastasia Khvorova, Oligonucleotide Compounds for Targeting Huntingtin mRNA.
U.S. Appl. No. 17/536,647 2022/0251554, filed Nov. 29, 2021 Aug. 11, 2022, Anastasia Khvorova, Oligonucleotide Compounds for Targeting Huntingtin mRNA.

(Continued)

*Primary Examiner* — Brian Whiteman
(74) *Attorney, Agent, or Firm* — LATHROP GPM LLP; James H. Velema, Esq.; Michael J. Spellberg

(57) ABSTRACT

Therapeutic oligonucleotides comprising pharmacokinetic (PK)-modifying anchors are provided. Methods for treating diseases or disorders comprising administering to a subject a therapeutic oligonucleotide comprising one or more PK-modifying anchors are provided.

32 Claims, 51 Drawing Sheets
(48 of 51 Drawing Sheet(s) Filed in Color)

(56) References Cited

U.S. PATENT DOCUMENTS

| | | |
|---|---|---|
| 8,703,731 B2 | 4/2014 | Jimenez et al. |
| 8,796,443 B2 | 8/2014 | Khvorova et al. |
| 8,815,818 B2 | 8/2014 | Samarsky et al. |
| 8,871,774 B2 | 10/2014 | Charifson et al. |
| 8,877,439 B2 | 11/2014 | Butora et al. |
| 8,906,874 B2 | 12/2014 | Rao et al. |
| 8,993,738 B2 | 3/2015 | Prakash et al. |
| 9,029,389 B2 | 5/2015 | No et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,198,981 B2 | 12/2015 | Ambati et al. |
| 9,303,259 B2 | 4/2016 | Khvorova et al. |
| 9,340,786 B2 | 5/2016 | Khvorova et al. |
| 9,493,774 B2 | 11/2016 | Kamens et al. |
| 9,745,574 B2 | 8/2017 | Woolf et al. |
| 9,796,756 B2 | 10/2017 | Hadwiger et al. |
| 9,809,817 B2 | 11/2017 | Khvorova et al. |
| 9,862,350 B2 | 1/2018 | Guerrero et al. |
| 9,862,952 B2 | 1/2018 | Khvorova et al. |
| 9,867,882 B2 | 1/2018 | Manoharan et al. |
| 10,087,210 B2 | 10/2018 | Prakash et al. |
| 10,435,688 B2 | 10/2019 | Khvorova et al. |
| 10,478,503 B2 | 11/2019 | Khvorova et al. |
| 10,479,992 B2 | 11/2019 | Woolf et al. |
| 10,519,451 B2 | 12/2019 | Khvorova et al. |
| 10,633,653 B2 | 4/2020 | Khvorova et al. |
| 10,774,327 B2 | 9/2020 | Khvorova et al. |
| 10,799,591 B2 | 10/2020 | Khvorova et al. |
| 10,844,377 B2 | 11/2020 | Khvorova et al. |
| 11,230,713 B2 | 1/2022 | Khvorova et al. |
| 11,279,930 B2 | 3/2022 | Khvorova et al. |
| 11,345,917 B2 | 5/2022 | Khvorova et al. |
| 11,492,619 B2 | 11/2022 | Khvorova et al. |
| 11,667,915 B2 | 6/2023 | Woolf et al. |
| 11,702,659 B2 | 7/2023 | Khvorova et al. |
| 11,753,638 B2 | 9/2023 | Khvorova et al. |
| 11,827,882 B2 | 11/2023 | Khvorova et al. |
| 11,896,669 B2 | 2/2024 | Khvorova et al. |
| 2001/0027251 A1 | 10/2001 | Cook et al. |
| 2003/0045705 A1 | 3/2003 | Cook |
| 2003/0143732 A1 | 7/2003 | Fosnaugh et al. |
| 2004/0121426 A1 | 6/2004 | Hsieh |
| 2004/0198640 A1 | 10/2004 | Leake et al. |
| 2004/0205839 A1 | 10/2004 | Doutriaux et al. |
| 2005/0096284 A1 | 5/2005 | McSwiggen |
| 2005/0220766 A1 | 10/2005 | Amalfitano et al. |
| 2005/0255487 A1 | 11/2005 | Khvorova et al. |
| 2006/0009409 A1 | 1/2006 | Woolf |
| 2006/0024715 A1 | 2/2006 | Liu et al. |
| 2006/0078542 A1 | 4/2006 | Mah et al. |
| 2006/0094032 A1 | 5/2006 | Fougerolles et al. |
| 2006/0105998 A1 | 5/2006 | Calogeropoulou et al. |
| 2007/0004664 A1 | 1/2007 | McSwiggen et al. |
| 2007/0004665 A1 | 1/2007 | McSwiggen et al. |
| 2007/0099860 A1 | 5/2007 | Sah et al. |
| 2007/0135372 A1 | 6/2007 | MacLachlan et al. |
| 2007/0160534 A1 | 7/2007 | Dennis et al. |
| 2007/0191273 A1 | 8/2007 | Ambat et al. |
| 2007/0259827 A1 | 11/2007 | Aronin et al. |
| 2008/0039415 A1 | 2/2008 | Stewart et al. |
| 2008/0108583 A1 | 5/2008 | Feinstein |
| 2008/0108801 A1 | 5/2008 | Manoharan |
| 2008/0119427 A1 | 5/2008 | Bhat et al. |
| 2008/0188429 A1 | 8/2008 | Iyer |
| 2008/0269149 A1 | 10/2008 | Bowles et al. |
| 2009/0143322 A1 | 6/2009 | Burkoth et al. |
| 2009/0234109 A1 | 9/2009 | Han et al. |
| 2009/0281299 A1 | 11/2009 | Manorahan et al. |
| 2009/0306178 A1 | 12/2009 | Bhat et al. |
| 2009/0318676 A1 | 12/2009 | Manoharan et al. |
| 2010/0015706 A1 | 1/2010 | Quay et al. |
| 2010/0093085 A1 | 4/2010 | Yamada et al. |
| 2010/0184209 A1 | 7/2010 | Vermeulen et al. |
| 2010/0186103 A1 | 7/2010 | Gao et al. |
| 2010/0240730 A1 | 9/2010 | Beigelman et al. |
| 2011/0039914 A1 | 2/2011 | Pavco et al. |
| 2011/0046206 A1 | 2/2011 | Bhat et al. |
| 2011/0086905 A1 | 4/2011 | Glazer |
| 2011/0097716 A1 | 4/2011 | Natt et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2012/0016005 A1 | 1/2012 | Samarsky et al. |
| 2012/0040459 A1 | 2/2012 | Khvorova et al. |
| 2012/0052487 A9 | 3/2012 | Khvorova et al. |
| 2012/0059046 A1 | 3/2012 | Woolf et al. |
| 2012/0065243 A1 | 3/2012 | Woolf et al. |
| 2012/0136039 A1 | 5/2012 | Aronin et al. |
| 2013/0065298 A1 | 3/2013 | Davidson et al. |
| 2013/0131141 A1 | 5/2013 | Khvorova et al. |
| 2013/0131142 A1 | 5/2013 | Libertine et al. |
| 2013/0196434 A1 | 8/2013 | Maier et al. |
| 2013/0197055 A1 | 8/2013 | Kamens et al. |
| 2013/0345218 A1 | 12/2013 | Charifson et al. |
| 2014/0005192 A1 | 1/2014 | Charifson et al. |
| 2014/0005197 A1 | 1/2014 | Charifson et al. |
| 2014/0113950 A1 | 4/2014 | Khvorova et al. |
| 2014/0155387 A1 | 6/2014 | No et al. |
| 2014/0296486 A1 | 10/2014 | Gao et al. |
| 2014/0315974 A1 | 10/2014 | Khvorova et al. |
| 2014/0364482 A1 | 12/2014 | Khvorova et al. |
| 2015/0025122 A1 | 1/2015 | Smith |
| 2015/0190525 A1 | 7/2015 | Tatro |
| 2015/0209441 A1 | 7/2015 | Carell |
| 2015/0232840 A1 | 8/2015 | Aronin et al. |
| 2015/0267200 A1 | 9/2015 | McSwiggen et al. |
| 2015/0315584 A1 | 11/2015 | MacDonald et al. |
| 2016/0017323 A1 | 1/2016 | Prakash et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0130583 A1 | 5/2016 | Yokota et al. |
| 2016/0244765 A1 | 8/2016 | Khvorova et al. |
| 2016/0281148 A1 | 9/2016 | Greenlee et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2016/0376598 A1 | 12/2016 | Lee et al. |
| 2017/0009239 A1 | 1/2017 | Khvorova et al. |
| 2017/0009304 A1 | 1/2017 | Zhou |
| 2017/0037456 A1 | 2/2017 | Kokoris et al. |
| 2017/0043024 A1 | 2/2017 | Khvorova et al. |
| 2017/0043204 A1 | 2/2017 | James |
| 2017/0051283 A1 | 2/2017 | Khvorova |
| 2017/0051286 A1 | 2/2017 | Smith |
| 2017/0067056 A1 | 3/2017 | Khvorova et al. |
| 2017/0183655 A1 | 6/2017 | Grabcysk et al. |
| 2017/0189541 A1 | 7/2017 | Foster |
| 2017/0281795 A1 | 10/2017 | Geall |
| 2017/0312367 A1 | 11/2017 | Khvorova et al. |
| 2017/0327524 A1 | 11/2017 | Nanna et al. |
| 2017/0369882 A1 | 12/2017 | Khvorova et al. |
| 2018/0023082 A1 | 1/2018 | Stanek et al. |
| 2018/0087052 A1 | 3/2018 | Hung et al. |
| 2018/0094263 A1 | 4/2018 | Khvorova et al. |
| 2018/0179546 A1 | 6/2018 | Khvorova et al. |
| 2018/0251764 A1 | 9/2018 | Albaek et al. |
| 2019/0024082 A1 | 1/2019 | Khvorova et al. |
| 2019/0144860 A1 | 5/2019 | Konstantinova et al. |
| 2019/0185855 A1 | 6/2019 | Khvorova et al. |
| 2019/0225965 A1 | 7/2019 | Khvorova et al. |
| 2019/0247507 A1 | 8/2019 | Khvorova et al. |
| 2020/0087663 A1 | 3/2020 | Aronin |
| 2020/0095580 A1 | 3/2020 | Hauptmann et al. |
| 2020/0123543 A1 | 4/2020 | Khvorova et al. |
| 2020/0165618 A1 | 5/2020 | Khvorova et al. |
| 2020/0270605 A1 | 8/2020 | Khvorova et al. |
| 2020/0308578 A1 | 10/2020 | Woolf et al. |
| 2020/0308584 A1 | 10/2020 | Khvorova et al. |
| 2020/0339983 A1 | 10/2020 | Khvorova et al. |
| 2020/0385740 A1 | 12/2020 | Khvorova et al. |

(56) References Cited

U.S. PATENT DOCUMENTS

| | | |
|---|---|---|
| 2021/0024926 A1 | 1/2021 | Khvorova et al. |
| 2021/0071117 A9 | 3/2021 | Khvorova et al. |
| 2021/0085793 A1 | 3/2021 | Khvorova et al. |
| 2021/0115442 A1 | 4/2021 | Khvorova et al. |
| 2021/0139901 A1 | 5/2021 | Khvorova et al. |
| 2021/0355491 A1 | 11/2021 | Khvorova et al. |
| 2021/0363523 A1 | 11/2021 | Khvorova et al. |
| 2022/0010309 A1 | 1/2022 | Khvorova et al. |
| 2022/0090069 A1 | 3/2022 | Khvorova et al. |
| 2022/0228141 A1 | 7/2022 | Khvorova et al. |
| 2022/0251554 A1 | 8/2022 | Khvorova et al. |
| 2022/0251555 A1 | 8/2022 | Khvorova et al. |
| 2022/0364100 A1 | 11/2022 | Khvorova et al. |
| 2023/0061751 A1 | 3/2023 | Khvorova et al. |
| 2023/0078622 A1 | 3/2023 | Khvorova et al. |
| 2023/0193281 A1 | 6/2023 | Khvorova et al. |
| 2023/0313198 A1 | 10/2023 | Khvorova et al. |
| 2023/0340475 A1 | 10/2023 | Khvorova et al. |
| 2023/0348907 A1 | 11/2023 | Khvorova et al. |
| 2023/0416735 A1 | 12/2023 | Khvorova et al. |

FOREIGN PATENT DOCUMENTS

| | | |
|---|---|---|
| CN | 104884618 A | 11/2015 |
| CN | 105194689 A | 12/2015 |
| EP | 1752536 A1 | 2/2007 |
| EP | 2407539 A1 | 1/2012 |
| EP | 2601204 A2 | 6/2013 |
| EP | 2853597 A1 | 4/2015 |
| EP | 3277811 A1 | 2/2018 |
| EP | 3277814 A1 | 2/2018 |
| EP | 3277815 A1 | 2/2018 |
| EP | 3408391 A1 | 12/2018 |
| EP | 3550021 A1 | 10/2019 |
| EP | 3642341 A1 | 4/2020 |
| EP | 3929293 A2 | 12/2021 |
| EP | 3946369 A2 | 2/2022 |
| EP | 4126040 A2 | 2/2023 |
| JP | H06-41183 A | 2/1994 |
| JP | H6-504680 A | 6/1994 |
| JP | 2001-501614 A | 2/2001 |
| JP | 2009-504782 A | 2/2009 |
| JP | 2010-506598 A | 3/2010 |
| JP | 2012-502657 A | 2/2012 |
| JP | 2013-049714 A | 3/2013 |
| JP | 2015-061534 A | 4/2015 |
| JP | 2016-171815 A | 9/2016 |
| JP | 2016-526529 A | 9/2016 |
| JP | 2018-516091 A | 6/2018 |
| WO | WO 1992/013869 A1 | 8/1992 |
| WO | WO 1993/009239 A1 | 5/1993 |
| WO | WO 1993/024641 A2 | 12/1993 |
| WO | WO 1994/022890 A1 | 10/1994 |
| WO | WO 1996/003500 A1 | 2/1996 |
| WO | WO 1998/013526 A1 | 4/1998 |
| WO | WO 2003/029459 A2 | 4/2003 |
| WO | WO 2004/008946 A2 | 1/2004 |
| WO | WO 2004/013280 A2 | 2/2004 |
| WO | WO 2004/044136 A2 | 5/2004 |
| WO | WO 2004/061081 A2 | 7/2004 |
| WO | WO 2004/108956 A1 | 12/2004 |
| WO | WO 2005/078095 A1 | 8/2005 |
| WO | WO 2006/019430 A2 | 2/2006 |
| WO | WO 2007/022470 A2 | 2/2007 |
| WO | WO 2007/022506 A2 | 2/2007 |
| WO | WO 2007/051045 A2 | 5/2007 |
| WO | WO 2007/056153 A2 | 5/2007 |
| WO | WO 2007/091269 A2 | 8/2007 |
| WO | WO 2007/094218 A1 | 8/2007 |
| WO | WO 2007/112414 A2 | 10/2007 |
| WO | WO 2008/005562 A2 | 1/2008 |
| WO | WO 2008/154482 A2 | 12/2008 |
| WO | WO 2008/154482 A3 | 12/2008 |
| WO | WO 2009/002944 A1 | 12/2008 |
| WO | WO 2009/054551 A2 | 4/2009 |
| WO | WO 2009/099991 A2 | 8/2009 |
| WO | WO 2009/102427 A2 | 8/2009 |
| WO | WO 2010/008582 A2 | 1/2010 |
| WO | WO 2010/011346 A1 | 1/2010 |
| WO | WO 2010/033246 A1 | 3/2010 |
| WO | WO 2010/033247 A2 | 3/2010 |
| WO | WO 2010/033248 A2 | 3/2010 |
| WO | WO 2010/048352 A2 | 4/2010 |
| WO | WO 2010/048585 A2 | 4/2010 |
| WO | WO 2010/059226 A2 | 5/2010 |
| WO | WO 2010/078536 A1 | 7/2010 |
| WO | WO 2010/090762 A1 | 8/2010 |
| WO | WO 2010/111503 A2 | 9/2010 |
| WO | WO 2010/118263 A1 | 10/2010 |
| WO | WO 2011/097643 A1 | 8/2011 |
| WO | WO 2011/109698 A1 | 9/2011 |
| WO | WO 2011/119852 A1 | 9/2011 |
| WO | WO 2011/119871 A1 | 9/2011 |
| WO | WO 2011/119887 A1 | 9/2011 |
| WO | WO 2011/125943 A1 | 10/2011 |
| WO | WO 2011/139702 A2 | 11/2011 |
| WO | WO 2011/158924 A1 | 12/2011 |
| WO | WO 2012/005898 A2 | 1/2012 |
| WO | WO 2012/058210 A1 | 5/2012 |
| WO | WO 2012/118911 A1 | 9/2012 |
| WO | WO 2012/131365 A1 | 10/2012 |
| WO | WO 2012/177906 A1 | 12/2012 |
| WO | WO 2013/089283 A1 | 6/2013 |
| WO | WO 2013/165816 A2 | 11/2013 |
| WO | WO 2014/009429 A1 | 1/2014 |
| WO | WO 2014/043544 A1 | 3/2014 |
| WO | WO 2014/076195 A1 | 5/2014 |
| WO | WO 2014/089313 A1 | 6/2014 |
| WO | WO 2014/201306 A1 | 12/2014 |
| WO | WO 2014/203518 A1 | 12/2014 |
| WO | WO 2015/025122 A1 | 2/2015 |
| WO | WO 2015/113004 A2 | 7/2015 |
| WO | WO 2015/161184 A1 | 10/2015 |
| WO | WO 2015/200078 A1 | 12/2015 |
| WO | WO 2016/028649 A1 | 2/2016 |
| WO | WO 2016/077321 A1 | 5/2016 |
| WO | WO 2016/077349 A1 | 5/2016 |
| WO | WO 2016/149331 A2 | 9/2016 |
| WO | WO 2016/161374 A1 | 10/2016 |
| WO | WO 2016/161378 A1 | 10/2016 |
| WO | WO 2016/161388 A1 | 10/2016 |
| WO | WO 2016/164866 | 10/2016 |
| WO | WO 2016/164866 A1 | 10/2016 |
| WO | WO 2016/205410 A2 | 12/2016 |
| WO | WO 2017/015555 A1 | 1/2017 |
| WO | WO 2017/024239 A1 | 2/2017 |
| WO | WO 2017/030973 A1 | 2/2017 |
| WO | WO 2017/062862 A2 | 4/2017 |
| WO | WO 2017/132669 A1 | 8/2017 |
| WO | WO 2017/174572 | 10/2017 |
| WO | WO 2018/031933 A2 | 2/2018 |
| WO | WO 2018/041973 A1 | 3/2018 |
| WO | WO 2018/185241 A1 | 10/2018 |
| WO | WO 2018/223056 A1 | 12/2018 |
| WO | WO 2018/237245 A1 | 12/2018 |
| WO | WO 2019/075418 A1 | 4/2019 |
| WO | WO 2019/075419 A1 | 4/2019 |
| WO | WO 2019/217459 A1 | 11/2019 |
| WO | WO 2019/232255 A1 | 12/2019 |
| WO | WO 2020/033899 A1 | 2/2020 |
| WO | WO 2020/041769 A1 | 2/2020 |
| WO | WO 2020/150636 A1 | 7/2020 |
| WO | WO 2020/198509 A2 | 10/2020 |
| WO | WO 2021/216556 A2 | 10/2021 |
| WO | WO 2021/195533 A2 | 11/2021 |
| WO | WO 2021/242883 A1 | 12/2021 |

OTHER PUBLICATIONS

U.S. Appl. No. 15/089,437 2016/0355826 U.S. Pat. No. 9,862,952, filed Apr. 1, 2016 Dec. 8, 2016 Jan. 9, 2018, Anastasia Khvorova, Oligonucleotide Compounds for Treatment of Preelampsia and Other Angiogenic Disorders.

(56) References Cited

OTHER PUBLICATIONS

U.S. Appl. No. 15/814,350 2018/0179546 U.S. Pat. No. 10,519,451, filed Nov. 15, 2017 Jun. 28, 2018 Dec. 31, 2019, Anastasia Khvorova, Oligonucleotide Compounds for Treatment of Preelampsia and Other Angiogenic Disorders.
U.S. Appl. No. 16/675,369 2020/0165618 U.S. Pat. No. 11,3445,917, filed Nov. 6, 2019 May 28, 2020 May 11, 2022, Anastasia Khvorova, Oligonucleotide Compounds for Treatment of Preelampsia and Other Angiogenic Disorders.
U.S. Appl. No. 17/718,918, filed Apr. 12, 2022, Anastasia Khvorova, Oligonucleotide Compounds for Treatment of Preelampsia and Other Angiogenic Disorders.
Alexopoulou, et al., Recognition of Double-Stranded RNA and Activation of NF-κB by Toll-like receptor 3, Nature, vol. 413, No. 6857, pp. 732-738, Oct. 18, 2001.
Alisky, et al., "Gene Therapy for Amyotrophic Lateral Sclerosis and Other Motor Neuron Diseases", Human Gene Therapy, vol. 11, Issue 17, pp. 2315-2329, Nov. 20, 2000.
Allerson et al., "Fully 2'-modified oligonucleotide duplexes with improved in vitro potency and stability compared to unmodified small interfering RNA", J Med Chem., Feb. 24, 2005, 48(4): 901-904.
Alterman, et al., Hydrophobically Modified siRNAs Silence Huntingtin mRNA in Primary Neurons and Mouse Brain, Molecular Therapy-Nucleic Acids, vol. 4, pp. e266, Dec. 1, 2015.
Alvarez-Erviti, et al., "Delivery of siRNA to the Mouse Brain by Systemic Injection of Targeted Exosomes", Nature Biotechnology, vol. 29, No. 4, pp. 341-345, Apr. 2011.
Alves, et al., Selectivity, Cooperativity, and Reciprocity in the Interactions between the δ-Opioid Receptor, its Ligands, and G-proteins, Journal of Biological Chemistry, vol. 279 No. 43, pp. 4673-44682, Aug. 17, 2004.
Amarzguioui, et al., "Tolerance for Mutations And Chemical Modifications in a siRNA", Nucleic Acids Research, Jan. 15, 2003, 31(2): 589-595.
Ambardekar et al., "The modification of siRNA with 3' cholesterol to increase nuclease protection and suppression of native mRNA by select siRNA polyplexes", Biomaterials, Elsevier, Amsterdam, NL, vol. 32, No. 5, pp. 1404-1411. (Nov. 2, 2010).
Ambros, et al., MicroRNAs and Other Tiny Endogenous RNAs in C. elegans, Current Biology, vol. 13, Issue 10, pp. 807-818, May 13, 2003.
Ameres, et al., Molecular Basis for Target RNA Recognition and Cleavage by Human RISC, Cell, vol. 130, Issue 1, pp. 101-112, Jul. 13, 2007.
Anderson, et al., Experimental Validation of the Importance of Seed Complement Frequency to siRNA Specificity, RNA, vol. 14, No. 5, pp. 853-861, Mar. 26, 2008.
Anderson, et al., Identifying siRNA-Induced Off-Targets by Microarray Analysis, Methods in Molecular Biology, vol. 442, pp. 45-63, 2008.
Atwell, et al., Stable Heterodimers from Remodeling the Domain Interface of a Homodimer Using a Phage Display Library, Journal of Molecular Biology, vol. 270, Issue 1, pp. 26-35, Jul. 4, 1997.
Aubuchon, et al., "Preeclampsia: Animal Models for a Human Cure", Proceedings of the National Academy of Sciences, vol. 108, No. 4, pp. 1197-1198, Jan. 25, 2011.
Aureli, et al., GM1 Ganglioside: Past Studies and Future Potential, Molecular Neurobiology, vol. 53, Issue 3, pp. 1824-1842, Apr. 2016.
Avino, et al., Branched Rna: A New Architecture for RNA Interference, Journal of Nucleic Acids, Article IC586935, 7 pages, Mar. 6, 2011.
Bagella, et al., Cloning of Murine CDK9/PITALRE and its Tissue-Specific Expression in Development, Journal of cellular physiology, vol. 177, No. 2, pp. 206-213, Dec. 7, 1998.
Bartlett, et al., Can Metastatic Colorectal Cancer Be Cured?, Journal Oncology, Cancer Network, vol. 26, No. 3, pp. 266-275, Mar. 15, 2012.
Bartlett, et al., Insights into the Kinetics of siRNA-Mediated Gene Silencing from Live-Cell And Live-Animal Bioluminescent Imaging, Nucleic Acids Research, vol. 34, Issue 1, pp. 322-333, Jan. 1, 2006.
Behlke, et al., Chemical Modification of siRNAs for in Vivo Use, Oligonucleotides, vol. 18, No. 4, pp. 305-320, Nov. 29, 2008.
Bell, et al., Liposomal Transfection Efficiency and Toxicity on Glioma Cell Lines: in Vitro and in Vitro Studies, Neuroreport, vol. 9, Issue 5, pp. 793-798, Mar. 30, 1998.
Billy, et al., Specific Interference with Gene Expression Induced by Long, Double-Stranded RNA in Mouse Embryonal Teratocarcinoma Cell Lines, Proceedings of the National Academy of Sciences, vol. 98, No. 25, pp. 14428-14433, Dec. 4, 2001.
Birmingham, et al., 3' UTR Seed Matches, but Not Overall Identity, Are Associated with RNAi Off-Targets, Nature Methods, vol. 3, No. 3, pp. 199-204, Feb. 17, 2006.
Birmingham, et al., A Protocol For Designing siRNAs With High Functionality And Specificity, Nature Protocols, vol. 2, No. 9, pp. 2068-2078, Aug. 23, 2007.
Boutla et al., "Short 5'-phosphorylated double-stranded RNAs induce RNA interference in Drosophila", Biology, 2001, 11: 1776-1780.
Braasch, et al., "RNA Interference in Mammalian Cells by Chemically-Modified RNA", Biochemistry, vol. 42, No. 26, pp. 7967-7975, Jun. 11, 2003.
Brennecke, et al., Towards a Complete Description of the microRNA Complement of Animal Genomes, Genome Biology, vol. 4, No. 9, 3 Pages, Aug. 21, 2003.
Brummelkamp, et al., A System for Stable Expression of Short Interfering RNAs in Mammalian Cells, Science, vol. 296, Issue 5567, pp. 550-553, Apr. 19, 2002.
Burchard, et al., MicroRNA-Like Off-Target Transcript Regulation by siRNAs is Species Specific, RNA, vol. 15, No. 2, pp. 308-315, 2009.
Burke, et al., "Spiral Arterial Remodeling Is Not Essential for Normal Blood Pressure Regulation in Pregnant Mice", Hypertension, vol. 55, No. 3, pp. 729-737, Jan. 25, 2010.
Byrne, et al., Novel Hydrophobically Modified Asymmetric RNAi Compounds (sd-rxRNA) Demonstrate Robust Efficacy in the Eye, Journal of Ocular Pharmacology and Therapeutics, vol. 29, Issue 10, pp. 855-864, Dec. 3, 2013.
Calegari, et al., Tissue-Specific RNA Interference in Postimplantation Mouse Embryos with Endoribonuclease-Prepared Short Interfering RNA, Proceedings of the National Academy of Sciences, vol. 99, No. 22, pp. 14236-14240, Oct. 29, 2002.
Carter, "Handbook of Parvoviruses", ed., P. Tijsser, CRC Press, pp. 155-168, 1990.
Chang, et al., Enhanced intracellular delivery and multi-target gene silencing triggered by tripodal RNA Structure, The journal of gene Medicine, vol. 14, No. 2, pp. 138-146, Feb. 2012.
Chang, et al., Transgenic Animal Models for Study of the Pathogenesis of Huntington's Disease and Therapy, Drug design, development and therapy, vol. 9, pp. 2179-2188, Apr. 2015.
Charnock-Jones, et al., "Identification and Localization of Alternately Spliced mRNAs for Vascular Endothelial Growth Factor in Human Uterus and Estrogen Regulation in Endometrial Carcinoma Cell Lines", Biology of Reproduction, vol. 48, pp. 1120-1128, 1993.
Charrier, et al., Inhibition of SRGAP2 Function by its Human-Specific Paralogs Induces Neoteny during Spine Maturation, Cell, vol. 149, Issue 4, pp. 923-935, May 11, 2012.
Chen et al., "Lipophilic siRNAs mediate efficient gene silencing in oligodendrocytes with direct CNC delivery", Journal Of Controlled Release, Elsevier, vol. 144, pp. 227-232. (Feb. 17, 2010).
Chen et al., "Thermoresponsive polypeptides from pegylated poly-L-glutamates", Biomacromolecules 2011, 12: 2859-2863.
Chen, et al., "Gene Therapy for Brain Tumors: Regression of Experimental Gliomas by Adenovirus-Mediated Gene Transfer in Vivo", Proceedings of the National Academy of Sciences, vol. 91, No. 8, pp. 3054-3057, 1994.
Cheng, et al., Enhanced Hepatic Uptake and Bioactivity of Type α1(I) Collagen Gene Promoter-Specific Triplex-Forming Oligonucleotides after Conjugation with Cholesterol, Journal of Pharmacology and Experimental Therapeutics, vol. 370, Issue 2, pp. 797-805, Aug. 1, 2019.

(56) References Cited

OTHER PUBLICATIONS

Cheung, et al., Effects of All-Trans-Retinoic Acid on Human SH-SYSY Neuroblastoma as in Vitro Model in Neurotoxicity Research, Neurotoxicology, vol. 30, No. 1, pp. 127-135, Jan. 1, 2009.

Cho, et al., Vascular Endothelial Growth Factor Receptor 1 Morpholino Decreases Angiogenesis in a Murine Corneal Suture Model, Investigative ophthalmology & visual science, vol. 53, Issue 2, pp. 685-692, Feb. 2012.

Choe, et al., Crystal Structure of Human Toll-Like Receptor 3 (TLR3) Ectodomain, Science, vol. 309, Issue 5734, pp. 581-585, Jun. 16, 2005.

Chung et al., "Reducible siRNA Dimeric Conjugates for Efficient Cellular Uptake and Gene Silencing", Bioconjugate Chem., 2011, 22(2): 299-306.

Coelho, et al., Safety and Efficacy of RNAi Therapy for Transthyretin Amyloidosis, New England Journal of Medicine, vol. 369, No. 9, pp. 819-829, Aug. 29, 2013.

Coles, et al., A High-Throughput Method for Direct Detection of Therapeutic Oligonucleotide-Induced Gene Silencing in Vivo, Nucleic Acid Therapeutics, vol. 26, Issue 2, pp. 86-92, Apr. 11, 2016.

Cui, et al., "Role of Corin in Trophoblast Invasion and Uterine Spiral Artery Remodelling in Pregnancy", Nature, vol. 484, No. 7393, pp. 246-250, Mar. 21, 2012.

Damha et al. (1990) "An improved procedure for derivatization of controlled-pore glass beads for solid-phase oligonucleotide synthesis," Nucleic Acids Research, 18(13):3813-3821.

Dass, Crispin R., Cytotoxicity Issues Pertinent to Lipoplex-Mediated Gene Therapy in-Vivo, Journal of Pharmacy and Pharmacology, vol. 54, Issue 5, pp. 593-601, Feb. 18, 2010.

Davidson, et al., A Model System for in Vivo Gene Transfer into the Central Nervous System Using an Adenoviral Vector, Nature Genetics, vol. 3, No. 3, pp. 219-223, Mar. 1, 1993.

Davidson, et al., Recombinant Adeno-Associated Virus Type 2, 4, and 5 Vectors: Transduction of Variant Cell Types And Regions in the Mammalian Central Nervous System, Proceedings of the National Academy of Sciences, vol. 97, No. 7, pp. 3428-3432, Mar. 28, 2000.

De Fougerolles, et al., "Interfering With Disease: a Progress Report on siRNA-based Therapeutics", Nature Reviews Drug Discovery, vol. 6, pp. 443-453, Jun. 2007.

De Marre et al., "Synthesis, characterization, and in vitro biodegradation of poly(ethylene glycol) modified poly[5N-(2-hydroxyethyl-L-glutamine]", J Bioact Compat Polym, 1996, 11: 85-99.

DeLeavey, et al., The 5' Binding MID Domain of Human Argonaute2 Tolerates Chemically Modified Nucleotide Analogues, Nucleic acid therapeutics, vol. 23, No. 1, pp. 81-87, Feb. 7, 2013.

DiFiglia, et al., Therapeutic Silencing of Mutant Huntingtin with siRNA Attenuates Striatal and Cortical Neuropathology and Behavioral Deficits, Proceedings of the National Academy of Sciences, vol. 104, No. 43, pp. 17204-17209, Oct. 23, 2007.

Dinusha, Differnce Between Sterol and Steroid, Home / Health / Medicine / Nutrients & Drugs, Aug. 4, 2011.

Doench, et al., siRNAs Can Function as miRNAs, Genes & Development, vol. 17, pp. 438-442, 2003.

Dohmen et al., "Defined Folate-PEG-siRNA Conjugates for Receptor-specific Gene Slicing", Molecular Therapy-Nucleic Acids, 2012, 1(1): e7.

Dufour, et al., Intrajugular Vein Delivery of AAV9-RNAi Prevents Neuropathological Changes and Weight Loss in Huntington's Disease Mice, Molecular Therapy, vol. 22, No. 4, pp. 797-810, Jan. 6, 2014.

Dyall, et al., Long-chain omega-3 fatty acids and the brain: a review of the independent and shared effects of EPA, DPA and DHA, Frontiers in Aging Neuroscience, vol. 7, p. 52, Apr. 21, 2015.

Eckstein, Phosphorothioate Oligodeoxynucleotides: What is Their Origin and What is Unique About Them?, Antisense and Nucleic Acid Drug Development, vol. 10, Issue 2, pp. 117-121, Jan. 30, 2009.

Egusquiaguirre, et al., "Nanoparticle Delivery Systems for Cancer Therapy: Advances in Clinical and Preclinical Research", Clinical and Translational Oncology, vol. 14, pp. 83-93, 2012.

El Andaloussi, et al., "Exosome-Mediated Delivery of siRNA in Vitro and in Vivo", Nature Protocols, vol. 7, No. 12, pp. 2112-2126, Nov. 15, 2012.

El Andaloussi, et al., "Exosomes for Targeted siRNA Delivery Across Biological Barriers", Advanced Drug Delivery Reviews, vol. 65, pp. 391-397, 2013.

El Andaloussi, et al., "Extracellular Vesicles: Biology and Emerging Therapeutic Opportunities", Nature Reviews Drug Discovery, vol. 12, pp. 347-357, May 2013.

Elmen, et al., Locked Nucleic Acid (LNA) Mediated Improvements in siRNA Stability and Functionality, Nucleic Acids Research, vol. 33, Issue 1, pp. 439-447, Jan. 14, 2005.

EMBL Database, WO 2005116204-A/113070: Double Strand Polynucleotides Generating RNA Interference, EBI Accession No. EM PAT:FW706544, XP055753619, , Apr. 18, 2011.

Eremina, et al., "Glomerular-Specific Alterations of VEGF-A Expression Lead to Distinct Congenital and Acquired Renal Diseases", Journal of Clinical Investigation, vol. 111, No. 5, pp. 707-716, Mar. 2003.

Eremina, et al., "VEGF Inhibition and Renal Thrombotic Microangiopathy", New England Journal of Medicine, vol. 358, No. 11, pp. 1129-1136, Mar. 13, 2008.

Evers, et al., Antisense Oligonucleotides in Therapy for Neurodegenerative Disorders, Advanced Drug Delivery Reviews, vol. 87, pp. 90-103, Jun. 29, 2015.

Extended European Search Report for European Patent Application No. 16837593.9, dated Mar. 20, 2019.

Extended European Search Report for European Patent Application No. 17745083.0, dated on Jul. 31, 2019.

Extended European Search Report for European Patent Application No. 17840367.1, dated Oct. 14, 2020.

Extended European Search Report for European Patent Application No. 20164108.1, dated on Dec. 3, 2020.

Extended European Search Report for European Patent Application No. 20216265.7, dated Feb. 10, 2022.

Extended European Search Report for European Patent Application No. 18819571.3, dated May 14, 2021.

Extended European Search Report for European Patent Application No. 21197881.2, dated Oct. 31, 2022.

Fan, et al., Endometrial VEGF Induces Placental sFLT1 and Leads to Pregnancy Complications, The Journal of clinical investigation, vol. 124, No. 11, pp. 4941-4952, Oct. 20, 2014.

Fattal, et al., Biodegradable Polyalkylcyanoacrylate Nanoparticles for the Delivery of Oligonucleotides, Journal of Controlled Release, vol. 53, pp. 137-143, May 1998.

Fedorov, et al., Off-Target Effects by siRNA Can Induce Toxic Phenotype, RNA, vol. 12, No. 7, pp. 1188-1196, May 2006.

Felber, et al., The Interactions of Amphiphilic Antisense Oligonucleotides with Serum Proteins and Their Effects on in Vitro Silencing Activity, Biomaterials, vol. 33, Issue 25, pp. 5955-5965, Sep. 2012.

Figueroa, et al., Neurorestorative Targets of Dietary Long-Chain Omega-3 Fatty Acids in Neurological Injury, Molecular Neurobiology, vol. 50, Issue 1, pp. 197-213, Aug. 2014.

Fisher, et al., Transduction with Recombinant Adeno-Associated Virus for Gene Therapy is Limited by Leading-Strand Synthesis, Journal of virology, vol. 70, No. 1, pp. 520-532, Jan. 1996.

Franich, et al., AAV Vector-Mediated RNAi of Mutant Huntingtin Expression is Neuroprotective in a Novel Genetic Rat Model of Huntington's Disease, Molecular Therapy, vol. 16, Issue 5, pp. 947-956, Mar. 25, 2008.

Frazier, Antisense Oligonucleotide Therapies: The Promise and the Challenges from a Toxicologic Pathologist's Perspective, Toxicologic pathology, vol. 43, Issue 1, pp. 78-89, Nov. 9, 2014.

Frigg et al., Relationships between vitamin A and vitamin E in the chick, Int J Vitam Nutr Res., 1984, 54(2-3): 125-133.

Furuhashi et al., Expression of Low Density Lipoprotein Receptor Gene in Hjuman Placenta during Pregnancy, Molecular Endocrinology, 1989, 3: 1252-1256.

(56) References Cited

OTHER PUBLICATIONS

Gaglione, et al., Recent Progress in Chemically Modified siRNAs, Mini Reviews in Medicinal Chemistry, vol. 10, No. 7, pp. pp. 578-595, 2010.
Gavrilov et al. (Jun. 2012) "Therapeutic siRNA: principles, challenges, and strategies", Yale Journal of Biology and Medicine, 85:187-200.
Geary, et al., Pharmacokinetics, Biodistribution and Cell Uptake of Antisense Oligonucleotides, Advanced Drug Delivery Reviews, vol. 87, pp. 46-51, Jun. 29, 2015.
Genbank, Mus Musculus Non-Coding RNA, Oocyte_Clustered_Small_RNA6599, Complete Sequence, GenBank Accession No. AB341398.1, May 24, 2008, 1 page.
Genbank, Rattus Norvegicus piRNA piR-182271, Complete Sequence, GenBank Accession No. DQ766949.1, Jul. 12, 2006, 1 Page.
Genbank, Signal Recognition Particle 54 kDa protein 2 [Perkinsus marinus ATCC 50983], NCBI Reference Sequence: XP_002784438.1, Apr. 30, 2010.
Gilany, et al., The Proteome of the Human Neuroblastoma Cell Line SH-SY5Y: An Enlarged Proteome, Biochimica et Biophysica Acta (BBA)—Proteins and Proteomics, vol. 1784, Issues 7-8, pp. 983-985, July-Aug. 2008.
Gilbert, et al., "Hypertension Produced by Reduced Uterine Perfusion in Pregnant Rats is Associated With Increased Soluble fms-like Tyrosine Kinase-1 Expression", Hypertension, vol. 50, No. 6, pp. 1142-1147, Oct. 8, 2007.
Gille, et al., "Analysis of Biological Effects and Signaling Properties of Flt-1 (VEGFR-1) and KDR (VEGFR-2)", Mechanisms of Signal Transduction, vol. 276, Issue 5, pp. 3222-3230, Feb. 2001.
Godard, et al., "Antisense Effects of Cholesterol-Oligodeoxynucleotide Conjugates Associated with Poly(alkylcyanoacrylate) Nanoparticles", European Journal of Biochemistry banner, vol. 232, pp. 404-410, 1995.
Grad, et al., Computational and Experimental Identification of C. elegans microRNAs, Molecular Cell, vol. 11, Issue 5, pp. 1253-1263, May 2003.
Gray, et al., Human Mutant Huntingtin with a Stable Polyglutamine Repeat Can Elicit Progressive and Selective Neuropathogenesis in BACHD Mice, Journal of Neuroscience, vol. 28, Issue 24, pp. 6182-6195, Jun. 11, 2008.
Griffiths-Jones, SAN, The microRNA Registry, Nucleic Acids Research, vol. 32, Issue Supplement 1, pp. D109-D111, Jan. 1, 2004.
Grimm, D, Asymmetry in siRNA Design, Gene Therapy, vol. 16, No. 7, pp. 827-829, Apr. 30, 2009.
Grimm, et al., Fatality in Mice Due to Oversaturation of Cellular MicroRNA/short Hairpin RNA Pathways, Nature, vol. 441, No. 7092, pp. 537-541, May 25, 2006.
Hamajima, et al., Intranasal Administration of HIV-DNA Vaccine Formulated with a Polymer, Carboxymethylcellulose, Augments Mucosal Antibody Production and Cell-Mediated Immune Response, Clinical Immunology and Immunopathology, vol. 88, Issue 2, pp. 205-210, Aug. 1998.
Haraszti, et al., "5'-Vinylphosphonate improves tissue accumulation and efficacy of conjugated siRNAs in vivo", Nucleic Acids Research, Jul. 27, 2017, 45(13): 7581-7592.
Herdewijn, Piet, Heterocyclic Modifications of Oligonucleotides and Antisense Technology, Antisense and Nucleic Acid Drug Development, vol. 10, Issue 4, pp. 297-310, Jul. 8, 2004.
Heydarian, et al., Novel Splice Variants of sFlt1 are Upregulated in Preeclampsia, Placenta, vol. 30, Issue 3, pp. 250-255, Mar. 2009.
Heyer, et al., An Optimized Kit-Free Method for Making Strand-Specific Deep Sequencing Libraries From RNA Fragments, Nucleic Acids Research, vol. 43, Issue 1, pp. 1-14, Jan. 9, 2015.
Hirashima, et al., "Trophoblast Expression of Fms-like Tyrosine Kinase 1 is Not Required for the Establishment of the Maternal-fetal Interface in the Mouse Placenta", Proceedings of the National Academy of Sciences of the United States of America, vol. 100, No. 26, pp. 15637-15642, Dec. 23, 2003.
Hodgson, et al., A YAC Mouse Model for Huntington's Disease with Full-Length Mutant Huntingtin, Cytoplasmic Toxicity, and Selective Striatal Neurodegeneration, Neuron, vol. 23, Issue 1, pp. 181-192, May 1999.
Hult, et al., Mutant Huntingtin Causes Metabolic Imbalance by Disruption of Hypothalamic Neurocircuits, Cell Metabolism, vol. 13, Issue 4, pp. 428-439, Apr. 6, 2011.
Hutvagner, et al., A microRNA in a Multiple-Turnover RNAi Enzyme Complex, Science, vol. 297, Issue 5589, pp. 2056-2060, Sep. 20, 2002.
Intapad, et al., "Reduced Uterine Perfusion Pressure Induces Hypertension in the Pregnant Mouse", American Journal of Physiology-Regulatory, Integrative and Comparative Physiology, vol. 307, Issue 11, pp. R1353-R1357, Dec. 2014.
International Search Report & Written Opinion Received for PCT Application No. PCT/US2019/046013, mailed on Jan. 9, 2020.
International Search Report & Written Opinion Received for PCT Application No. PCT/US2020/014181, mailed on Jun. 2, 2020.
International Search Report and Written Opinion in related PCT Application No. PCT/US2020/014146, mailed May 22, 2020.
International Search Report and Written Opinion received for PCT Patent Application No. PCT/US2016/025722, mailed on Aug. 12, 2016.
International Search Report and Written Opinion received for PCT Patent Application No. PCT/US2016/025731, mailed on Sep. 9, 2016.
International Search Report and Written Opinion received for PCT Patent Application No. PCT/US2016/025753, mailed on Sep. 14, 2016.
International Search Report and Written Opinion received for PCT Patent Application No. PCT/US2016/046810, mailed on Nov. 29, 2016.
International Search Report and Written Opinion received for PCT Patent Application No. PCT/US2017/015633, mailed on May 11, 2017.
International Search Report and Written Opinion received for PCT Patent Application No. PCT/US2018/038952, mailed on Sep. 24, 2018.
International Search Report and Written Opinion received for PCT Patent Application No. PCT/US2020/045487, mailed on Dec. 31, 2020.
International Search Report and Written Opinion received for PCT Patent Application No. PCT/US2021/013620, mailed on Apr. 26, 2021.
Iriyama et al., Hypoxia-independent up-regulation of placental HIF-1α gene expression contributes to the pathogenesis of preeclampsia, Hypertension, Jun. 2015, 65(6): 1307-1315, Supplemental Data.
Iriyama et al., Hypoxia-independent up-regulation of placental HIF-1α gene expression contributes to the pathogenesis of preeclampsia, Hypertension, Jun. 2015, 65(6): 1307-1315.
Iversen et al., "Optimized siRNA-PEG Conjugates for Extended Blood Circulation and Reduced Urine Excretion in Mice", Feb. 25, 2013, Theranostics 2013, vol. 3, Issue 3, pp. 201-209.
Jackson, et al., Position-Specific Chemical Modification of siRNAs Reduces "Off-Target" Transcript Silencing, RNA, vol. 12, No. 7, pp. 1197-1205, May 8, 2006.
Jackson, et al., Recognizing and Avoiding siRNA Off-Target Effects for Target Identification and Therapeutic Application, Nature Reviews Drug Discovery, vol. 9, No. 1, pp. 57-67, Jan. 1, 2010.
Jacque, et al., Modulation of HIV-1 replication by RNA interference, Nature, vol. 418, No. 6896, pp. 435-438, Jun. 26, 2002.
Janssen, et al., Long-Chain Polyunsaturated Fatty Acids (LCPUFA) from Genesis to Senescence: The Influence of LCPUFA on Neural Development, Aging, and Neurodegeneration, Progress in Lipid Research, vol. 53, pp. 1-17, Jan. 2014.
Jebbink et al., "Expression of Placental FLT1 Transcript Variants Relates to Both Gestational Hypertensive Disease and Fetal Growth", Hypertension, Apr. 25, 2011, 58(1): 70-76.
Jin, et al., DARPP-32 to Quantify Intracerebral Hemorrhage-induced Neuronal Death in Basal Ganglia, Translational Stroke Research, vol. 4, No. 1, pp. 130-134, Feb. 1, 2013.

(56) References Cited

OTHER PUBLICATIONS

Jo, et al., Selection and Optimization of Asymmetric siRNA Targeting the Human c-MET Gene, Molecules and cells, vol. 32, No. 6, pp. 543-548, Dec. 31, 2011.
Judge, et al., Design of Noninflammatory Synthetic siRNA Mediating Potent Gene Silencing in Vivo, Molecular Therapy, vol. 13, Issue 3, pp. 494-505, Mar. 2006.
Kamba, et al., "VEGF-dependent Plasticity of Fenestrated Capillaries in the Normal Adult Microvasculature", American Journal of Physiology-Heart and Circulatory Physiology, vol. 29, pp. H560-H576, Feb. 1, 2006.
Karlin, et al., Applications and Statistics for Multiple High-Scoring Segments in Molecular Sequences, Proceedings of the National Academy of Sciences of the USA, vol. 90, pp. 5873-5877, Jun. 1993.
Karlin, et al., Methods For Assessing the Statistical Significance of Molecular Sequence Features by Using General Scoring Schemes, Proceedings of the National Academy of science of the USA, vol. 87, No. 6, pp. 2264-2268, Mar. 1990.
Karra, et al., Transfection Techniques for Neuronal Cells, Journal of Neuroscience, vol. 30, No. 18, pp. 6171-6177, May 5, 2010.
Kenski et al. (2012) "siRNA-optimized Modifications for Enhanced in Vivo Activity," Mol. Ther. Nucleic Acids. 1:e5. pp. 1-8.
Khankin, et al., "Intravital High-frequency Ultrasonography to Evaluate Cardiovascular and Uteroplacental Blood Flow in Mouse Pregnancy", Pregnancy Hypertension: An International Journal of Women's Cardiovascular Health, vol. 2, pp. 84-92, 2012.
Khvorova, et al., Abstract IA27: Advances in Oligonucleotide Chemistry for the Treatment of Neurodegenerative Disorders and Brain Tumors, Cancer Research, vol. 76, Issue 6, Abstract IA27, Mar. 2016.
Khvorova, et al., Functional siRNAs and miRNAs Exhibit Strand Bias, Cell, vol. 115, Issue 2, pp. 209-216, Oct. 17, 2003.
Kordasiewicz, et al., Sustained Therapeutic Reversal of Huntington's Disease by Transient Repression of Huntingtin Synthesis, Neuron, vol. 74, Issue 6, pp. 1031-1044, Jun. 21, 2012.
Kubo et al., "Lipid-Conjugated 27-Nucleotide Double-Stranded RNAs with Dicer-Substrate Potency enhance RNAi-Mediated Gene Silencing", Molecular Pharmaceutics, American Chemical Society, US, vol. 9, No. 5, pp. 1374-1382, DOI: 10.1021/MP2006278. (Apr. 11, 2012).
Kubo et al., "Palmitic Acid-Conjugated 21-Nucleotide siRNA Enhances Gene-Silencing Activity", Molecular Pharmaceutics, vol. 8, No. 6, pp. 2193-2203, DOI: 10.1021/mp200250f. (Oct. 10, 2011).
Kumar, et al., "Shielding of Lipid Nanoparticles for siRNA Delivery: Impact on Physicochemical Properties", Cytokine Induction, and Efficacy, Molecular Therapy-Nucleic Acids, vol. 3, e210, pp. 1-7, Nov. 18, 2014.
Lagos-Quintana, et al., Identification of Novel Genes Coding for Small Expressed RNAs, Science, vol. 294, Issue 5543, pp. 853-858, Oct. 26, 2001.
Lagos-Quintana, et al., Identification of Tissue-Specific MicroRNAs from Mouse, Current Biology, vol. 12, Issue 9, pp. 735-739, Apr. 30, 2002.
Lagos-Quintana, et al., New microRNAs From Mouse And Human, RNA, vol. 9, No. 2, pp. 175-179, 2003.
Lai, et al., Computational Identification of Drosophila microRNA Genes, Genome Biology, vol. 4, No. 7, pp. 1-20, Jun. 30, 2003.
Lam, et al., "A New Type of Synthetic Peptide Library For Identifying Ligand-Binding Activity", Nature, vol. 354, pp. 82-84, Nov. 7, 1991.
Lambert, et al., "Nanoparticulate Systems for the Delivery of Antisense Oligonucleotides", Advanced Drug Delivery Reviews, vol. 47, pp. 99-112, 2001.
Lan, et al., Neuroactive Steroid Actions at the GABAA Receptor, Hormones and Behavior, vol. 28, Issue 4, pp. 537-544, Dec. 1994.
Landis, et al., "A Call for Transparent Reporting to Optimize the Predictive Value of Preclinical Research", Nature, vol. 490, pp. 187-191, Oct. 10, 2012.
Lau, et al., An Abundant Class of Tiny RNAs with Probable Regulatory Roles in Caenorhabditis elegans, Science, vol. 294, Issue 5543, pp. 858-862, Oct. 26, 2001.
Lau, et al., Characterization of the piRNA Complex from Rat Testes, Science, vol. 313, Issue 5785, pp. 363-367, Jul. 21, 2006.
Laufer, et al., "Selected Strategies for the Delivery of siRNA in Vitro and in Vivo", RNA Technologies and Their Applications, 2010, pp. 29-58.
Lee, et al., "Recent Developments in Nanoparticle-Based siRNA Delivery for Cancer Therapy", BioMed Research International, vol. 2013, Article ID 782041, 10 Pages, Jun. 2013.
Lee, et al., An Extensive Class of Small RNAs in Caenorhabditis elegans, Science, vol. 294, Issue 5543, pp. 862-864, Oct. 26, 2001.
Lee, et al., Expression of Small Interfering RNAs Targeted Against HIV-1 rev Transcripts in Human Cells, Nature Biotechnology, vol. 20, No. 5, pp. 500-505, May 1, 2002.
Lee, et al., RNA Interference-Mediated Simultaneous Silencing of Four Genes Using Cross-Shaped RNA, Molecules and Cells, vol. 35, No. 4, pp. 320-326, Apr. 4, 2013.
Lee, et al., Small-interfering RNA (siRNA)-based functional micro- and nanostructures for efficient and selective gene silencing, Accounts of Chemical Research, vol. 45, No. 7, pp. 1014-1025, Jul. 17, 2012.
Levine, et al., "Circulating Angiogenic Factors and the Risk of Preeclampsia", The New England Journal of Medicine, vol. 350, pp. 672-683, 2004.
Li, et al., "Recombinant Vascular Endothelial Growth Factor 121 Attenuates Hypertension and Improves Kidney Damage in a Rat Model of Preeclampsia", Hypertension, vol. 50, pp. 686-692, 2007.
Li, et al., Distribution of 5-Hydroxymethylcytosine in Different Human Tissues, "SAGE—Hindawi Access to Research, Journal of Nucleic Acids, vol. 2011", pp. 1-7, 2011.
Li, et al., Huntington's Disease Gene (IT15) is Widely Expressed in Human and Rat Tissues, Neuron, vol. 11, No. 5, pp. 985-993, Nov. 1993.
Lim, et al., The microRNAs of Caenorhabditis elegans, Genes & Development, vol. 17, No. 8, pp. 991-1008, 2003.
Lim, et al., Vertebrate MicroRNA Genes, Science, vol. 299, Issue 5612, p. 1540, Mar. 7, 2003.
Lima, et al., Single-Stranded siRNAs Activate RNAi in Animals, Cell, vol. 150, Issue 5, pp. 883-894, Aug. 31, 2012.
Lopes, et al., Comparison Between Proliferative and Neuron-Like SH-SY5Y Cells as an in Vitro Model for Parkinson Disease Studies, Brain Research, vol. 1337, pp. 85-94, Jun. 14, 2010.
Lorenz, et al., Steroid and Lipid Conjugates of siRNAs to Enhance Cellular Uptake and Gene Silencing in Liver Cells, Bioorganic & Medicinal Chemistry Letters, vol. 14, Issue 19, pp. 4975-4977, Oct. 4, 2004.
Lundh, et al., Hypothalamic Expression of Mutant Huntingtin Contributes to the Development of Depressive-Like Behavior in the Bac Transgenic Mouse Model of Huntington's Disease, Human Molecular Genetics, vol. 22, Issue 17, pp. 3485-3497, Sep. 1, 2013.
Luo, et al., Photoreceptor Avascular Privilege is Shielded by Soluble VEGF Receptor-1, Elife, vol. 2, pp. 1-22, Jun. 18, 2013.
Makris, et al., "Uteroplacental Ischemia Results in Proteinuric Hypertension and Elevated sFLT-1", Kidney International, vol. 71, Issue 1, pp. 977-984, May 2, 2007.
Maltepe, et al., "The Placenta: Transcriptional, Epigenetic, and Physiological Integration During Development", The Journal of Clinical Investigation, vol. 120, No. 4, pp. 1016-1025, Apr. 1, 2010.
Mangiarini, et al., Exon 1 of the HD Gene with an Expanded CAG Repeat Is Sufficient to Cause a Progressive Neurological Phenotype in Transgenic Mice, Cell, vol. 87, Issue 3, pp. 493-506, Nov. 1, 1996.
Mantha, et al., Rnai-Based Therapies for Huntington's Disease: Delivery Challenges and Opportunities, Therapeutic Delivery, vol. 3, No. 9, pp. 1061-1076, Aug. 29, 2012.
Marcus, et al., FedExosomes: Engineering Therapeutic Biological Nanoparticles that Truly Deliver, Pharmaceuticals, vol. 6, No. 5, pp. 659-680, Apr. 29, 2013.
Marques, et al., A Structural Basis for Discriminating Between Self and Nonself Double-Stranded Rnas in Mammalian Cells, Nature biotechnology, vol. 23, No. 11, pp. 1399-1405, 2005.

(56) References Cited

OTHER PUBLICATIONS

Masotti, et al., Comparison of Different Commercially Available Cationic Liposome-DNA Lipoplexes: Parameters Influencing Toxicity And Transfection Efficiency, Colloids and Surfaces B: Biointerfaces, vol. 68, Issue 2, pp. 136-144, Feb. 1, 2009.

Maynard, et al., "Excess Placental Soluble fms-like Tyrosine Kinase 1 (sFltl) may Contribute to Endothelial Dysfunction", Hypertension, and Proteinuria in Preeclampsia, The Journal of Clinical Investigation, vol. 111, pp. 649-658, 2003.

Mccaffrey, et al., Gene Expression: RNA Interference in Adult Mice, Nature, vol. 418, No. 6893, pp. 38-39, Jul. 4, 2002.

Mcmanus, et al., Gene Silencing Using Micro-RNA Designed Hairpins, RNA, vol. 8, Issue 6, pp. 842-850, Aug. 20, 2002.

Miyagishi, et al., U6 promoter-driven siRNAs with Four Uridine 3' Overhangs Efficiently Suppress Targeted Gene Expression in Mammalian Cells, Nature Biotechnology, vol. 20, No. 5, pp. 497-500, May 1, 2002.

Mok, et al., Multimeric small interfering ribonucleic acid for highly efficient sequence-specific gene silencing~, Nature Materials, vol. 9, pp. 272-278, Jan. 24, 2010.

Molitoris, et al., siRNA Targeted to p53 Attenuates Ischemic and Cisplatin-Induced Acute Kidney Injury, Journal of the American Society of Nephrology, vol. 20, Issue 8, pp. 1754-1764, Aug. 1, 2009.

Morrissey et al., "Activity of stabilized short interfering RNA in a mouse model of hepatitis B virus replication", Hepatology, 2005, 41: 1349-1356.

Mourelatos, et al., miRNPs: A Novel Class Of Ribonucleoproteins Containing Numerous microRNAs, Genes & Development, vol. 16, No. 6, pp. 720-728, 2002.

Mullen, et al., NeuN, A Neuronal Specific Nuclear Protein in Vertebrates, Development, vol. 116, No. 1, pp. 201-211, 1992.

Myers, et al., Optimal Alignments in Linear Space, Computer Applications in the Biosciences, vol. 4, No. 1, pp. 11-17, Mar. 1988.

Nagamatsu, et al., "Cytotrophoblasts Up-Regulate Soluble Fms-Like Tyrosine Kinase-1 Expression under Reduced Oxygen: An Implication for the Placental Vascular Development and the Pathophysiology of Preeclampsia", Endocrinology, vol. 145, Issue 11, pp. 4838-484, Nov. 1, 2004.

Nair, et al., Multivalent N-Acetylgalactosamine-Conjugated siRNA Localizes in Hepatocytes and Elicits Robust RNAi-Mediated Gene Silencing, Journal of the American Chemical Society, vol. 136, No. 49, p. 16958-16961, Dec. 10, 2014.

Nelson et al. (1992) "Oligonucleotide labeling methods 3. Direct labeling of oligonucleotides employing a novel, non-nucleosidic, 2-aminobutyl-1,3-propanediol backbone," 20(23):6253-6259.

Neufeld, et al., "Similarities and Differences Between the Vascular Endothelial Growth Factor (VEGF) Splice Variants", Cancer and Metastasis Reviews, vol. 15, pp. 153-158, Jun. 1996.

Nielsen, et al., Sequence-Selective Recognition of DNA by Strand Displacement with a Thymine-Substituted Polyamide, Science, vol. 254, Issue 5037, pp. 1497-1500, Dec. 6, 1991.

Nikan, et al., Docosahexaenoic Acid Conjugation Enhances Distribution and Safety of SiRNA upon Local Administration in Mouse Brain, Molecular Therapy—Nucleic Acids, vol. 5, No. 8, pp. 1-11, Aug. 9, 2016.

Nishina et al., "Efficient in Vivo Delivery of siRNA to the Liver by Conjugation of α-Tocopherol", Mol Ther., Apr. 2008, 16(4): 734-740.

Ohnishi, et al., "Enhancement of Allele Discrimination by Introduction of Nucleotide Mismatches into siRNA in Allele-Specific Gene Silencing by RNAi", Plos One, vol. 3, Issue 5, e2248, 9 Pages, May 2008.

Osborn, et al., "Improving siRNA Delivery in Vivo Through Lipid Conjugation", Nucleic Acid Therapeutics, vol. 28, No. 3, pp. 128-136, May 10, 2018.

Østergaard, et al., "Fluorinated Nucleotide Modifications Modulate Allele Selectivity of SNP-Targeting Antisense Oligonucleotides", Molecular Therapy Nucleic Acids, vol. 7, pp. 20-30, Jun. 2017.

Ouimet, et al., DARPP-32, A Dopamine- and Adenosine 3':5'-Monophosphate-Regulated Phosphoprotein Enriched in Dopamine-Innervated Brain Regions. III. Immunocytochemical Localization, Journal of Neuroscience, vol. 4, No. 1, pp. 111-124, Jan. 1, 1984.

Overhoff, et al., "Quantitative Detection of siRNA and Single-stranded Oligonucleotides: Relationship Between Uptake and Biological Activity of siRNA", Nucleic Acids Research, vol. 32, Issue 21, pp. 1-5, Dec. 2, 2004.

Owen, Morpholino-Mediated Increase in Soluble Flt-1 Expression Results in Decreased Ocular and Tumor Neovascularization, PLoS One, vol. 7, No. 3, pp. e33576, Mar. 15, 2012.

Paddison, et al., Short Hairpin RNAs (shRNAs) Induce Sequence-Specific Silencing in Mammalian Cells, Genes & Development, vol. 16, No. 8, pp. 948-958, 2002.

Partial European Search Report for European Patent Application No. 20216265.7, dated Nov. 10, 2021.

Partial European Search Report for European Patent Application No. 21197881.2, mailed Mar. 14, 2022.

Pasquinelli, et al., Conservation of the Sequence and Temporal Expression of let-7 Heterochronic Regulatory RNA, Nature, vol. 408, No. 6808, pp. 86-89., Nov. 2, 2000.

Paul, et al., Effective Expression of Small Interfering RNA in Human Cells, Nature Biotechnology, vol. 20, No. 5, pp. 505-508, May 1, 2002.

Peel, et al., Conjugation and Evaluation of Small Hydrophobic Molecules to Triazole-Linked siRNAs, ACS medicinal chemistry letters, vol. 6, No. 2, pp. 117-122, Dec. 4, 2014.

Pei, et al., Quantitative Evaluation of siRNA Delivery in Vivo, RNA, vol. 16, No. 12, pp. 2553-2563, Oct. 12, 2010.

Petersen, et al., LNA: A Versatile Tool for Therapeutics and Genomics, Trends in Biotechnology, vol. 21, Issue 2, pp. 74-81, Feb. 2003.

Pfister, et al., "Five siRNAs Targeting Three SNPs in Huntingtin May Provide Therapy for Three-Quarters of Huntington's Disease Patients", Current Biology, vol. 19, No. 9, pp. 774-778., May 12, 2009.

Podbevsek et al., "Solution-state structure of a fully alternately 2'-F/2'-OMe modified 42-nt dimeric siRNA construct", Nucleic Acids Research, vol. 38, No. 20, pp. 7298-7307, DOI: 10.1093/nar/gkq621. (Jul. 12, 2010).

Posocco, et al., "Impact of siRNA Overhangs for Dendrimer-mediated siRNA Delivery and Gene Silencing", Molecular Pharmaceutics, Aug. 5, 2013, 10(8): 3262- 3273.

Powe, et al., "Preeclampsia, a Disease of the Maternal Endothelium: the Role of Antiangiogenic Factors and Implications for Later Cardiovascular Disease", Circulation, vol. 123, No. 24, pp. 2856-2869, Jun. 11, 2011.

Pubchem Database, Amino-Teg-Diol, National Institute or Biotechnology Information, PubChem Accession No. 22136768, 2003.

Pubchem Database, SCHEMBL867745, National Institute for Biotechnology Information, PubChem Accession No. 12454428, 12 pages, 2005.

Putnam, David A., Antisense Strategies and Therapeutic Applications, American Journal of Health System Pharmacy, vol. 53, No. 2, pp. 151-160, Jan. 15, 1996.

Raouane et al., "Lipid Conjugated Oligonucleotides: A Useful Strategy for Delivery", Chem., 2012, 23: 1091-1104.

Reinhart, et al., Small RNAs Correspond to Centromere Heterochromatic Repeats, Science, vol. 297, No. 5588, 1 Page, Sep. 13, 2002.

Rigo, et al., Pharmacology of a Central Nervous System Delivered 2'-O-Methoxyethyl-Modified Survival of Motor Neuron Splicing Oligonucleotide in Mice and Nonhuman Primates, Journal of Pharmacology and Experimental Therapeutics, vol. 350, Issue 1, pp. 46-55, Jul. 1, 2014.

Rodriguez-Lebron, et al., Intrastriatal rAAV-Mediated Delivery of Anti-Huntingtin shRNAs Induces Partial Reversal of Disease Progression in R6/1 Huntington's Disease Transgenic Mice, Molecular Therapy, vol. 12, Issue 4, pp. 618-633, Oct. 2005.

Rupprecht, et al., Neuroactive Steroids: Mechanisms of Action and Neuropsychopharmacological Properties, Psychoneuroendocrinology, vol. 28, Issue 2, pp. 139-168, Feb. 2003.

Rusckowski, et al., Biodistribution and Metabolism of a Mixed Backbone Oligonucleotide (GEM 231) Following Single and Mul-

(56) References Cited

OTHER PUBLICATIONS tiple Dose Administration in Mice, Antisense and Nucleic Acid Drug Development, vol. 10, Issue 5, pp. 333-345, Jan. 30, 2009.
Sah, et al., Oligonucleotide Therapeutic Approaches for Huntington disease, The Journal of Clinical Investigation, vol. 121, No. 2, pp. 500-507, Feb. 1, 2011.
Samuelson, Kristin W., Post-Traumatic Stress Disorder and Declarative Memory Functioning: A Review, Dialogues in Clinical Neuroscience, vol. 13, No. 3, pp. 346-351, Sep. 2011.
Schirle, et al., Structural Basis for MicroRNA Targeting, Science, vol. 346, Issue 6209, pp. 608-613, Oct. 31, 2014.
Schwab, et al., An Approach for New Anticancer Drugs:Oncogene-Targeted Antisense DNA, Annals of Oncology, vol. 5, Issue 4, pp. 55-58, 1994.
Schwarz, et al., Asymmetry in the Assembly of the RNAi Enzyme Complex, Cell, vol. 115, Issue 2, pp. 199-208, Oct. 17, 2003.
Seq Id No. 1112 from U.S. Pat. No. 7,790,867. [Accessed Nov. 28, 2018, http://seqdata.USPTO.gov/.psipsv?pageRequest=viewSequence&DocID=7790867&seqID=1112.].
Song, et al., Sustained Small Interfering RNA-Mediated Human Immunodeficiency Virus Type 1 Inhibition in Primary Macrophages, Journal of Virology, vol. 77, No. 13, pp. 7174-7181, 2003.
Soutschek, et al., Therapeutic Silencing of an Endogenous Gene by Systemic Administration of Modified siRNAs, Nature, vol. 432, No. 7014, pp. 173-178, Nov. 11, 2004.
Stalder, et al., The Rough Endoplasmatic Reticulum is a Central Nucleation Site of SiRNA-Mediated RNA Silencing, The EMBO Journal, vol. 32, Issue 8, pp. 1115-1127, Mar. 19, 2013.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.
Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.
Stokman, et al., Application of siRNA in Targeting Protein Expression in Kidney Disease, Advanced Drug Delivery Reviews, vol. 62, Issue 14, pp. 1378-1389, Nov. 30, 2010.
Sui, et al., A Dna Vector-Based RNAi Technology to Suppress Gene Expression in Mammalian Cells, Proceedings of the National Academy of Sciences, vol. 99, No. 8, pp. 5515-5520, Apr. 16, 2002.
Tabernero, et al., First-in-Humans Trial of an RNA Interference Therapeutic Targeting VEGF and KSP in Cancer Patients with Liver Involvement, vol. 3, Issue 4, pp. 406-417, Apr. 2013.
Tang, et al., "Excess Soluble Vascular Endothelial Growth Factor Receptor-1 in Amniotic Fluid Impairs Lung Growth in Rats: Linking Preeclampsia With Bronchopulmonary Dysplasia", American Journal of Physiology-Lung Cellular and Molecular Physiology, vol. 302, No. 1, pp. L36-L46, Jan. 1, 2012.
Thadani, et al., "Pilot Study of Extracorporeal Removal of Soluble fms-like Tyrosine kinase 1 in Preeclampsia", Circulation, vol. 124, No. 8, pp. 940-950, Aug. 1, 2011.
Thomas et al. (2007) "Intronic polyadenylation signal sequences and alternate splicing generate human soluble Flt1 variants and regulate the abundance of soluble Flt1 in the placenta," The FASEB Journal, 21(14):3885-3895.
Thomas, et al., A Recently Evolved Novel Trophoblast-Enriched Secreted Form of fms-Like Tyrosine Kinase-1 Variant is Up-Regulated in Hypoxia and Preeclampsia, The Journal of Clinical Endocrinology & Metabolism, vol. 94, Issue 7, pp. 2524-2530, Jul. 1, 2009.
Tischer, et al., "The Human Gene for Vascular Endothelial Growth Factor. Multiple Protein Forms are Encoded Through Alternative Exon Splicing", The Journal of Biological Chemistry, vol. 266, p. 11947-11954, Jun. 25, 1991.
Turanov et al., "RNAi Modulation of Placental sFLT1 for the Treatment of Preeclampsia", Nature Biotechnology, Nov. 19, 2018, 36: 1164-1173.
Tuschl et al. (May 6, 2004) "The siRNA User Guide," Accessible on the Internet at URL: http://diyhpl.US/~bryan/irc/protocol-online/protocol-cache/sirna.html. [Last Accessed Aug. 11, 2016].
Tuschl, et al., Expanding small RNA interference, Nature Biotechnology, vol. 20, No. 5, pp. 446-448, 2002.
Uchida, et al., "An Integrated Approach for the Systematic Identification and Characterization of Heart-enriched Genes With Unknown Functions", BMC Genomics, vol. 10, No. 100, pp. 1-12, Mar. 2009.
Ueno et al., "Synthesis and silencing properties of siRNAs possessing lipophilic groups at their 3'-termini", Nucleic Acids Symposium Series, vol. 52, Issue 1, pp. 503-504, https://doi.org/10.1093/nass/nrn255. (Sep. 2008).
Vaught, et al., T7 RNA Polymerase Transcription with 5-Position Modified UTP Derivatives, Journal of the American Chemical Society, vol. 126, No. 36, pp. 11231-11237, Aug. 19, 2004.
Videira, et al., "Preclinical Development of siRNA Therapeutics: Towards the Match Between Fundamental Science and Engineered Systems", Nanomedicine: Nanotechnology, Biology and Medicine, vol. 10, No. 4, pp. 689-702, 2014.
Vorlová, et al., "Induction of Antagonistic Soluble Decoy Receptor Tyrosine Kinases by Intronic polyA Activation", Molecular Cell, vol. 43, Issue 6, pp. 927-939, Sep. 16, 2011.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wada et al., "Evaluation of the effects of chemically different linkers on hepatic accumulations, cell tropism and gene silencing ability of cholesterol-conjugated antisense oligonucleotides", Journal Of Controlled Release, Elsevier, vol. 226, pp. 57-65, Doi: 10.1016/J.JCONREL.2016.02.007. (Feb. 5, 2016).
Wang, et al., Nanoparticle-Based Delivery System for Application of siRNA in Vivo, Current Drug Metabolism, vol. 11, No. 2, pp. 182-196, 2010.
Watanabe, et al., Endogenous siRNAs From Naturally Formed dsRNAs Regulate Transcripts In Mouse Oocytes, Nature, vol. 453, No. 7194, pp. 539-543, Apr. 10, 2008.
Weyer, et al., Developmental and Cell Type-Specific Expression of the Neuronal Marker NeuN in the Murine Cerebellum, Journal of Neuroscience Research, vol. 73, Issue 3, pp. 400-409, May 23, 2003.
Whitehead, et al., "Knocking Down Barriers: Advances in siRNA Delivery", Nature Reviews Drug Discovery, vol. 8, No. 2, pp. 129-138, Feb. 2009.
Wolfrum et al., "Mechanisms and optimization of in vivo delivery of lipophilic siRNAs", Nature Biotechnology, Oct. 2007, 25(10): 1149-1157.
Wong, et al., Co-Injection of a Targeted, Reversibly Masked Endosomolytic Polymer Dramatically Improves the Efficacy of Cholesterol-Conjugated Small Interfering RNAs in Vivo, Nucleic Acid Therapeutics, vol. 22, No. 6, pp. 380-390, Nov. 26, 2012.
Wooddell, et al., Hepatocyte-targeted RNAi Therapeutics for the Treatment of Chronic Hepatitis B Virus Infection, Molecular Therapy, vol. 21, Issue 5, pp. 973-985, May 2013.
Wright, et al., Identification of Factors That Contribute to Recombinant AAV2 Particle Aggregation and Methods to Prevent its Occurrence During Vector Purification and Formulation, Molecular Therapy, vol. 12, Issue 1,, pp. 171-178, Jul. 2005.
Xia, et al., siRNA-Mediated Gene Silencing in Vitroand in Vivo, Nature Biotechnology, vol. 20, No. 10, pp. 1006-1010, Sep. 16, 2002.
Young, et al., Pathogenesis of Preeclampsia, Annual Review of Pathology: Mechanisms of Disease, vol. 5, pp. 173-192, Feb. 2, 2010.
Younis, et al., Overview of the Nonclinical Development Strategies and Class-Effects of Oligonucleotide-Based Therapeutics, A Comprehensive Guide to Toxicology in Preclinical Drug Development, Chapter 26, pp. 647-664, 2013.
Yu, et al., RNA Interference by Expression of Short-Interfering RNAs and Hairpin Rnas in Mammalian Cells, Proceedings of the National Academy of Sciences, vol. 99, No. 9, pp. 6047-6052., Apr. 30, 2002.
Yu, et al., Single-Stranded RNAs Use RNAi to Potently and Allele-Selectively Inhibit Mutant Huntingtin Expression, Cell, vol. 150, Issue 5, pp. 895-908, Aug. 31, 2012.

(56) References Cited

OTHER PUBLICATIONS

Yuan, et al., Recent Advances of siRNA Delivery by Nanoparticles, Expert Opinion on Drug Delivery vol. 8, Issue 4, pp. 521-536, 2011.
Zeng, et al., Both Natural and Designed Micro RNAs Can Inhibit the Expression of Cognate mRNAs When Expressed in Human Cells, Molecular Cell, vol. 9, pp. 1327-1333, Jun. 2002.
Zeng, et al., Sequence Requirements for Micro RNA Processing and Function in Human Cells, RNA, vol. 9, pp. 112-123, 2003.
Zhang, et al., "Birth-weight-for-gestational-age Patterns by Race, Sex, and Parity in the United States Population", Obstetrics & Gynecology, vol. 86, No. 2, pp. 200-208, 1995.
Zhang, et al., "Several rAAV Vectors Efficiently Cross the Blood-brain Barrier and Transduce Neurons and Astrocytes in the Neonatal Mouse Central Nervous System", Molecular Therapy, vol. 19, Issue 8, pp. 1440-1448, Aug. 1, 2011.
Zhang, et al., Cyclohexane 1,3-Diones and Their Inhibition of Mutant SOD1—Dependent Protein Aggregation and Toxicity in PC12 Cells, Bioorganic & Medicinal Chemistry, vol. 20, Issue 2, pp. 1029-1045, Jan. 15, 2012.
Zou, et al., Liposome-Mediated NGF Gene Transfection Following Neuronal Injury: Potential Therapeutic Applications, Gene Therapy, vol. 6, No. 6, pp. 994-1005, Jun. 25, 1999.
Zuccato, et al., Molecular Mechanisms and Potential Therapeutical Targets in Huntington's Disease, Physiological Reviews, vol. 90, No. 3, pp. 905-981, Jul. 1, 2010.
Akinc et al., A Combinatorial Library of Lipid-like Materials for Delivery of RNAi Therapeutics, Nature Biotechnology, vol. 26, No. 5, 20 Pages, May 2008.
Alagia, et al., Exploring PAZ/3'-overhang Interaction to Improve siRNA Specificity. A Combined Experimental and Modeling Study, Chemical Science, vol. 9, No. 8, pp. 2074-2086, 2018.
Alterman et al., "A divalent siRNA chemical scaffold for potent and sustained modulation of gene expression throughout the central nervous system", Nat Biotechnol., Aug. 2019, 37(8): 884-894.
Ämmälä, et al., Targeted Delivery of Antisense Oligonucleotides to Pancreatic β-cells, Science Advances, vol. 4, No. 10, eaat3386, pp. 1-11, Oct. 17, 2018.
Betkekar, et al., A Tandem Enyne/Ring Closing Metathesis Approach to 4-Methylene-2-cyclohexenols: An Efficient Entry to Otteliones and Loloanolides, Organic Letters, Dec. 6, 2011, vol. 14, No. 1, pp. 198-201,.
Biscans et al., "Docosanoic acid conjugation to siRNA enables functional and safe delivery to skeletal and cardiac muscles", Molecular Therapy, Apr. 2021, vol. 29, No. 4, pp. 1382-1394.
Biscans et al., "Hydrophobicity of Lipid-Conjugated siRNAs Predicts Productive Loading to Small Extracellular Vesicles", Molecular Therapy, Jun. 2018, vol. 26, No. 6, pp. 1520-1528.
Biscans et al., "The Chemical Structure and Phosphorothioate content of hydrophobically modified siRNAs impact extrahepatic distribution and efficacy", Nucleic Acids Research, 2020, vol. 48, No. 14, pp. 7665-7680.
Biscans et al., Diverse Lipid Conjugates for Functional Extra-Hepatic siRNA Delivery in Vivo, Nucleic Acids Research, vol. 47, No. 3, pp. 1082-1096, Dec. 14, 2018.
Biscans, et al., The Valency of Fatty Acid Conjugates Impacts siRNA Pharmacokinetics, Distribution, and Efficacy in Vivo, Journal of Controlled Release, vol. 302, pp. 116-125, Mar. 2019.
Brown, et al., Effect of Phosphorothioate Modification of Oligodeoxynucleotides on Specific Protein Binding, Journal of Biological Chemistry, vol. 269, No. 43, pp. 26801-26805, 1994.
Chang, et al., Asymmetric Shorter-duplex siRNA Structures Trigger Efficient Gene Silencing with Reduced Nonspecific Effects, Molecular Therapy, vol. 17, Issue 4, pp. 725-732, Apr. 2009.
Chappell, et al., Mechanisms of Palmitic Acid-conjugated Antisense Oligonucleotide Distribution in Mice, Nucleic Acids Research, vol. 48, Issue 8, ,, pp. 4382-4395, May 7, 2020.
Chen et al., Influence of Particle Size on the in Vivo Potency of Lipid Nanoparticle Formulations of siRNA, Journal of Controlled Release, vol. 235, pp. 236-244, Aug. 10, 2016.

Choi et al., Suppression of diacylglycerol acyltransferase-2 (DGAT2), but not DGAT1, with antisense oligonucleotides reverses diet-induced hepatic steatosis and insulin resistance, J Biol Chem., Aug. 3, 2007, 282(31): 22678-22688.
Chu, et al., Potent RNAi by Short RNA Triggers, RNA, vol. 14, pp. 1714-1719, 2008.
Collis, "The synthesis of vinylphosphonate-linked RNA", Ph.D. Thesis, University of Nottingham, Feb. 2008.
Crooke, et al., Cellular Uptake and Trafficking of Antisense Oligonucleotides, Nature Biotechnology, vol. 35, No. 3, pp. 230-237, Mar. 2017.
Crooke, et al., Phosphorothioate Modified Oligonucleotide-Protein Interactions, Nucleic Acids Research, May 1, 2020, 48(10): 5235-5253.
Czauderna, et al., Structural Variations and Stabilising Modifications of Synthetic siRNAs in Mammalian Cells, Nucleic Acids Research, vol. 31, Issue 11, pp. 2705-2716, Jun. 2003.
Dahlman et al., In Vivo Endothelial siRNA Delivery using Polymeric Nanoparticles with Low Molecular Weight, Nature Nanotechnology, vol. 9, No. 8, 17 Pages, Aug. 2014.
De Paula et al., "Hydrophobization and bioconjugation for enhanced siRNA delivery and targeting", RNA, Feb. 28, 2007, vol. 13, No. 4, pp. 431-456.
Doddridge et al., Effects of Vinylphosphonate Internucleotide Linkages on the Cleavage Specificity of Exonuclease III and on the Activity of DNA Polymerase I, Biochemistry, Mar. 25, 2003, 42(11): 3239-3246.
Dowdy, Overcoming Cellular Barriers for RNA Therapeutics, Nature Biotechnology, vol. 35, pp. 222-229, Feb. 27, 2017.
Ducruix, et al., Crystallization of Nucleic Acids and Proteins: A Practical Approach, Second Edition, 1999, pp. 201-216.
Echevarría, et al., Evaluating the Impact of Variable Phosphorothioate Content in Tricyclo-DNA Antisense Oligonucleotides in a Duchenne Muscular Dystrophy Mouse Model, Nucleic Acid Therapeutics, vol. 29, No. 3, pp. 148-160, May 30, 2019.
Eckstein, Developments in RNA Chemistry, A Personal View, Biochimie, vol. 84, No. 9, pp. 841-848, Sep. 2002.
Egli, et al., Re-engineering RNA Molecules into Therapeutic Agents, Accounts of Chemical Research, vol. 52, pp. 1036-1047, 2019.
Elbashir, et al., RNA Interference is Mediated By 21- and 22-Nucleotide RNAs, Genes & Development, vol. 15, No. 2, pp. 188-200, 2001.
Etzold et al., "The extension of the sugar chain of thymidine: a new route to 5'-deoxyhexose nucleosides", Chemical Communications (London), 1968, Issue 7.
Extended European Search Report for European Patent Application No. 19852320.1, dated May 2, 2022.
Extended European Search Report for European Patent Application No. 20741865.8, dated Apr. 26, 2023.
Extended European Search Report for European Patent Application No. 19847586.5, dated Jun. 21, 2023.
Fitzgerald, et al., A Highly Durable RNAi Therapeutic Inhibitor of PCSK9, New England Journal of Medicine, vol. 376, No. 1, pp. 41-51, Jan. 5, 2017.
Foster et al., "Advanced siRNA Designs Further Improve in Vivo Performance of GalNAc-siRNA Conjugates", Molecular Therapy, vol. 26, No. 3, pp. 709-717, Mar. 2018.
Frank et al., Structural Basis for 5'-Nucleotide Base-specific Recognition of Guide RNA by Human AGO2, Nature, vol. 465, pp. 818-822, Jun. 2010.
Gaus, et al., Characterization of the Interactions of Chemically-modified Therapeutic Nucleic Acids with Plasma Proteins Using a Fluorescence Polarization Assay, Nucleic Acids Research, vol. 47, No. 3, pp. 1110-1122, 2019.
Geary, Antisense Oligonucleotide Pharmacokinetics and Metabolism, Expert Opinion on Drug Metabolism & Toxicology, vol. 5, pp. 381-391, Apr. 1, 2009.
Ghidini et al., "An RNA modification with remarkable resistance to RNase A", Chemical Communicaitons, Aug. 8, 2013, 49(79): 9036-9038.
Godinho et al., Pharmacokinetic Profiling of Conjugated Therapeutic Oligonucleotides: A High-Throughput Method based upon Serial

(56) References Cited

OTHER PUBLICATIONS

Blood Microsampling Coupled to Peptide Nucleic Acid Hybridization Assay, Nucleic Acid Therapeutics, vol. 27, pp. 323-334, Dec. 1, 2017.
Goodson et al., Dental Applications, Medical Applications of Controlled Release, vol. 2, pp. 115-138, 1984.
Gvozdeva et al., "Noncanonical Synthetic RNAi Inducers InL RNA Interference", InTech, Apr. 6, 2016.
Haly et al., "An extended phosphate linkage: Synthesis, hybridization and modeling studies of modified oligonucleotides", Nucleosides and Nucleotides, 1996, 15(7-8): 1383-1395.
Hammerling et al., Monoclonal Antibodies and T-Cell Hybridomas, Research Monographs in Immunology, vol. 3, pp. 563-681, 1981.
Hanuš et al., "-CH2—lengthening of the internucleotide linkage in the ApA dimer can improve its conformational compatibility with its natural polynucleotide counterpart", Nucleic Acids Research, Dec. 15, 2001, 29(24): 5182-5194.
Harborth et al., Sequence, Chemical, and Structural Variation of Small Interfering RNAs and Short Hairpin RNAs and the Effect on Mammalian Gene Silencing, Antisense and Nucleic Acid Drug Development, vol. 13, pp. 83-105, Apr. 1, 2003.
Hassler et al., Comparison of Partially and Fully Chemically-Modified siRNA in Conjugate-Mediated Delivery in Vivo, Nucleic Acids Research, vol. 46, No. 5, pp. 2185-2196, Mar. 16, 2018.
Hillier et al., yw97a12.r1 Soares_placenta_8to9weeks_2NbHP8to9W Homo sapiens cDNA clone Image:260158 5' similar to GB:X51602_cds1 Vascular Endothelial Growth Factor Receptor 1 (Human); contains element OFR repetitive element, mRNA sequence, NIH, Genbank Accession No. N47911.1, Feb. 14, 1996.
Hong et al., "Reducible Dimeric Conjugates of Small Internally Segment Interfering RNA for Efficient Gene Silencing", Macromolecular Bioscience, Jun. 2016, vol. 16, No. 10, pp. 1442-1449.
Huang, Preclinical and Clinical Advances of GalNAc-Decorated Nucleic Acid Therapeutics, Molecular Therapy—Nucleic Acids, vol. 6,, pp. 116-132, Mar. 17, 2017.
International Preliminary Report on Patentability for PCT International Patent Application No. PCT/US2019/046013, mailed Apr. 28, 2020.
International Preliminary Report on Patentability for PCT Patent Application No. PCT/US2020/025017, mailed Sep. 28, 2021.
International Preliminary Report on Patentability for PCT Patent Application No. PCT/US2021/034290, mailed Nov. 17, 2022.
International Search Report and Written Opinion for PCT International Patent Application No. PCT/US2019/048027 mailed Nov. 15, 2019.
International Search Report and Written Opinion for PCT International Patent Application No. PCT/US2020/047492, mailed Feb. 17, 2022.
International Search Report and Written Opinion for PCT International Patent Application No. PCT/US2020/025017, mailed Sep. 18, 2020.
International Search Report and Written Opinion in related PCT Application No. PCT/US2021/024425, mailed Oct. 15, 2021.
International Search Report and Written Opinion received for PCT Patent Application No. PCT/US2021/034290, mailed on Nov. 4, 2021.
International Search Report and Written Opinion received for PCT Patent Application No. PCT/US2021/041946, mailed on Oct. 29, 2021.
International Search Report and Written Opinion received for PCT Patent Application No. PCT/US2021/060356, mailed on Apr. 13, 2022.
Jung et al., "Gene silencing efficiency of siRNA-PEG conjugates: Effect of PEGylation site and PEG molecular weight", Journal of Controlled Release, Mar. 4, 2010, vol. 144, No. 3, pp. 306-313.
Kachare et al., "Phospho-carboxylic anhydride of a homologated nucleoside leads to primer degradation in the presence of a polymerase", Bioorg Med Chem Letters, Jun. 15, 2014, 24(12): 2720-2723.

Karaki et al., Lipid-Oligonucleotide Conjugates Improve Cellular Uptake and Efficiency of TCTP-Antisense in Castration-Resistant Prostate Cancer, Journal of Controlled Release, vol. 258, pp. 1-9, Jul. 28, 2017.
Kaura, et al., Synthesis, Hybridization Characteristics, and Fluorescence Properties of Oligonucleotides Modified with Nucleobase-Functionalized Locked Nucleic Acid Adenosine and Cytidine Monomers, The Journal of Organic Chemistry, Jun. 16, 2014, 79: 6256-6268.
Khan et al., Silencing Myostatin using Cholesterol-Conjugated siRNAs Induces Muscle Growth, Molecular Therapy, Nucleic Acids, vol. 5, 9 Pages, Jan. 1, 2016.
Khvorova, Oligonucleotide Therapeutics—A New Class of Cholesterol-Lowering Drugs, The New England Journal of Medicine, vol. 376, No. 1, pp. 4-7, Jan. 5, 2017.
Kim et al., "LHRH Receptor-Mediated Delivery of siRNA Using Polyelectrolyte Complex Micelles Self-Assembled from siRNA-PEG-LHRH Conjugate and PEI", Bioconjugate Chemistry, Oct. 14, 2008, vol. 19, No. 11, pp. 2156-2162.
Kim et al., "PEG conjugated VEGF siRNA for anti-angiogenic gene therapy", Journal of Controlled Release, Jun. 3, 2006, vol. 116, No. 2, pp. 123-129.
Kofoed et al., "Oligodeoxynucleotides with Extended 3'- and 5'-Homologous Internucleotide Linkages", Acta Chemica Scandanavia, 1997, 51: 318-324.
Kubo, et al., Modified 27-nt dsRNAs With Dramatically Enhanced Stability in Serum and Long-term RNAi Activity, Oligonucleotides, vol. 17, No. 4, pp. 445-464, 2007.
Lebedeva et al., "Phosphorothioate oligodeoxynucleotides as inhibitors of gene expression: antisense and non-antisense effects", Applications of Antisense therapies to restenosis, 1999, p. 101.
Lee et al., "Current preclinical small interfering RNA (siRNA)-based conjugate systems for RNA therapeutics", Advanced Drug Delivery Reviews, Oct. 27, 2015, vol. 104, pp. 78-92.
Liang, et al., Identification and Characterization of Intracellular Proteins That Bind Oligonucleotides With Phosphorothioate Linkages, Nucleic Acids Research, vol. 43, Issue 5, pp. 2927-2945, Mar. 11, 2015.
Liu et al., Snapshot PK: A Rapid Rodent in Vivo Preclinical Screening Approach, Drug Discovery Today, vol. 13, No. 7-8, pp. 360-367, Apr. 1, 2008.
Loy et al., "Allele-Specific Gene Silencing in Two Mouse Models of Autosomal Dominant Skeletal Myopathy", PLoS One, Nov. 2012, 7(11): e49757, 11 pages.
Ly et al., Visualization of Self-Delivering Hydrophobically Modified siRNA Cellular Internalization, Nucleic Acids Research, vol. 45, pp. 15-25, Nov. 29, 2016.
Ma et al., Structural Basis For 5'-End-Specific Recognition of Guide RNA by the A. Fulgidus Piwi Protein, Nature, vol. 434, No. 7033, pp. 666-670, Mar. 31, 2005.
Ma, et al., Structural Basis for Overhang-Specific Small Interfering RNA Recognition by the PAZ Domain, Nature, vol. 429, No. 6989, pp. 318-322, May 20, 2004.
Magner et al., "Influence of mismatched and bulged nucleotides on SNP-preferential RNase H cleavage of RNA-antisense gapmer heteroduplexes", Scientific Reports, Oct. 2017, 7(12532), 16 pages.
Matsuda et al., siRNA Conjugates Carrying Sequentially Assembled Trivalent N-Acetylgalactosamine Linked Through Nucleosides Elicit Robust Gene Silencing in Vivo in Hepatocytes, ACS Chemical Biology, vol. 10, No. 5, pp. 1181-1187, Mar. 2, 2015.
Mazur et al., "Isosteres of natural phosphates. 11. Synthesis of a phosphonic acid analogue of an oligonucleotide", Tetrahedron, 1984, 40(20): 3949-3956.
Mikhailov et al., "Use of 5-deoxy-ribo-hexofuranose derivatives for the preparation of 5'-nucleotide phosphonates and homoribonucleosides", Collect Czech Chem Commun., 1989, 54(4): 1055-1066.
Miller, et al., Receptor-mediated Uptake of Phosphorothioate Antisense Oligonucleotides in Different Cell Types of the Liver, Nucleic Acid Therapeutics, vol. 28, No. 3, pp. 119-127, 2018.
Monteys et al., "Artificial miRNAs Targeting Mutant Huntingtin Show Preferential Silencing in Vitro and in Vivo", Molecular Therapy, Nucleic Acids, 2015, 4: E234, 11 pages.

(56) References Cited

OTHER PUBLICATIONS

Nair, et al., Impact of Enhanced Metabolic Stability on Pharmacokinetics and Pharmacodynamics of GalNAc-siRNA Conjugates, Nucleic Acids Research, vol. 45, Issue 19, pp. 10969-10977, Nov. 2, 2017.
Nallagatla et al., Nucleoside Modifications Modulate Activation of the Protein Kinase PKR in an RNA Structure-Specific Manner, RNA, vol. 14, pp. 1201-1213, Jun. 1, 2008.
Nikan et al., Synthesis and Evaluation of Parenchymal Retention and Efficacy of a Metabolically Stable, O-Phosphocholine-N-Docosahexaenoyl-L-serine siRNA Conjugate in Mouse Brain, Bioconjugate Chemistry, vol. 28, No. 6, 21 Pages, Jun. 21, 2017.
Oberbauer et al., Renal Uptake of an 18-mer Phosphorothioate Oligonucleotide, Kidney International, vol. 48, pp. 1226-1232, 1995.
Ohtsuka et al., "Joining of synthetic ribotrinucleotides with defined catalyzed by T4 RNA ligase", European Journal of Biochemistry, 1977, 81(2): 285-291.
Osborn et al., Hydrophobicity Drives the Systemic Distribution of Lipid-Conjugated siRNAs via Lipid Transport Pathways, Nucleic Acids Research, vol. 47, No. 3, pp. 1070-1081, Dec. 8, 2018.
Padiukova et al., "Synthesis of 5'-derivatives of thymidine", Bioorg Khim., 1990, 16(5): 668-673 [Article in Russian—no abstract available].
Parmar, et al., 5'-(E)-Vinylphosphonate: A Stable Phosphate Mimic can Improve the RNAi Activity of siRNA-GalNAc Conjugates, ChemBioChem, vol. 17, pp. 985-989, Jun. 2, 2016.
Partial Supplementary European Search Report for European Patent Application No. 20741865.8, mailed Dec. 20, 2022.
Partial Supplementary European Search Report for European Patent Application No. 20777915.8, mailed Apr. 5, 2023.
Pokholenko et al., Lipid Oligonucleotide Conjugates as Responsive Nanomaterials for Drug Delivery, Journal of Materials Chemistry B, vol. 1, 6 Pages, 2013.
Prakash et al., Targeted Delivery of Antisense Oligonucleotides to Hepatocytes Using Triantennary N-Acetyl Galactosamine Improves Potency 10-Fold in Mice, Nucleic Acids Research, vol. 42, Issue 13, pp. 8796-8807, Jul. 29, 2014.
Prakash, et al., Identification of Metabolically Stable 5'-Phosphate Analogs That Support Single-Stranded siRNA Activity, Nucleic Acids Research, Mar. 9, 2015, 43(6): 2993-3011.
PubChem Detabase, CID-16131506, Compund Summary: dGTGGGTGGGT, Jul. 3, 2007, Retrieved from url: https://pubchem.ncbi.nlm.nih.gov/compound/16131506.
Raal, et al., Inclisiran for the Treatment of Heterozygous Familial Hypercholesterolemia, New England Journal of Medicine, vol. 382, No. 16, pp. 1520-1530, Apr. 16, 2020.
Rajeev et al., Hepatocyte-Specific Delivery of Sirnas Conjugated to Novel Non-Nucleosidic Trivalent N-Acetylgalactosamine Elicits Robust Gene Silencing in Vivo, ChemBioChem, vol. 16, pp. 903-908, Apr. 13, 2015.
Reed et al., Forty Mouse Strain Survey of Body Composition, Physiology & Behavior, vol. 91, No. 5, 15 Pages, Aug. 15, 2007.
Reynolds, A, et al., Rational siRNA Design for RNA Interference, Nature Biotechnology, vol. 22, No. 3, pp. 326-330, Apr. 2004.
Roy et al., "Synthesis of DNA/RNA and Their Analogs via Phosphoramidite and H-Phosphonate Chemistries", Molecules, 2013, 18(11): 14268-14284.
Rozners et al., "Synthesis and Properties of RNA Analogues Having Amides as Interuridine Linkages at Selected Positions", JACS Articles, Sep. 6, 2003, 125: 12125-12136.
Sarett et al., Lipophilic siRNA Targets Albumin in Situ and Promotes Bioavailability, tumor Penetration, and Carrier-Free Gene Silencing, Proceedings of the National Academy of Sciences, vol. 114, pp. E6490-E6497, Jul. 24, 2017.
Scherman et al., Genetic Pharmacology: Progresses in siRNA Delivery and Therapeutic Applications, Gene Therapy, vol. 24, pp. 151-156, Mar. 2017.
Schlegal et al., "Chirality Dependent Potency Enhancement and Structural Impact of Glycol Nucleic Acid Modification on siRNA", JACS, Jun. 1, 2017, pp. 1-28.
Schoch, et al., Antisense Oligonucleotides: Translation From Mouse Models to Human Neurodegenerative Diseases, Neuron, vol. 94, Issue 6, pp. 1056-1070, Jun. 21, 2017.
Setten, et al., The Current State and Future Directions of RNAi-based Therapeutics, Nature Reviews Drug Discovery, vol. 18, pp. 421-446, Mar. 7, 2019.
Shen, et al., 2'-fluoro-modified Phosphorothioate Oligonucleotide Can Cause Rapid Degradation of P54nrb and PSF, Nucleic Acids Research, vol. 43, Issue 9, pp. 4569-4578, May 19, 2015.
Shen, et al., Acute Hepatotoxicity of 2' Fluoro-modified 5-10-5 Gapmer Phosphorothioate Oligonucleotides in Mice Correlates With Intracellular Protein Binding and the Loss of DBHS Proteins, Nucleic Acids Research, vol. 46, Issue 5, pp. 2204-2217, Mar. 16, 2018.
Shen, et al., Chemical Modification of PS-ASO Therapeutics Reduces Cellular Protein-binding and Improves the Therapeutic Index, Nature Biotechnology, vol. 37, pp. 640-650, Apr. 29, 2019.
Shukla et al., "Exploring Chemical Modifications for siRNA Therapeutics: A Structural and Functional Outlook", ChemMedChem, Feb. 19, 2010, 5(3): 328-349.
Sipova et al., "5'-O-Methylphosphonate nucleic acids—new modified DNAs that increase the Escherichia coli RNase H cleavage rate of hybrid duplexes", Nucleic Acids Research, 2014, 42(8): 5378-5389.
Smith et al., Reversed-Phase High Performance Liquid Chromatography of Phosphatidylcholine: A Simple Method for Determining Relative Hydrophobic Interaction of Various Molecular Species, Journal of Lipid Research, vol. 22, pp. 697-704, May 1, 1981.
Solano et al., Toxicological and Pharmacokinetic Properties of QPI-1007, a Chemically Modified Synthetic siRNA Targeting Caspase 2 mRNA, Following Intravitreal Injection, Nucleic Acid Therapeutics, vol. 24, pp. 258-266, Aug. 1, 2014.
Stein, et al., Physicochemical Properties of Phosphorothioate Oligodeoxynucleotides, Nucleic Acids Research, vol. 16, No. 8, pp. 3209-3221, Apr. 25, 1988.
Sugo et al., "Development of antibody-siRNA conjugate targeted to cardiac and skeletal muscles", Journal of Controlled Release, Jun. 29, 2016, vol. 237, pp. 1-13.
Suhr et al., Efficacy and Safety of Patisiran for Familial Amyloidotic Polyneuropathy: A Phase II Multi-Dose Study, Orphanet Journal of Rare Diseases, vol. 10, pp. 1-9, Dec. 1, 2015.
Sun, et al., Asymmetric RNA Duplexes Mediate RNA Interference in Mammalian Cells, Nature Biotechnology, vol. 26, pp. 1379-1382, Dec. 2008.
Tan et al., "Allele-Specific Targeting of microRNAs to HLA-G and Risk of Asthma", American Journal of Human Genetics, Oct. 2007, 81(4): 829-834.
Taniguchi et al., Plasmodium Berghei ANKA Causes Intestinal Malaria Associated with Dysbiosis, Scientific Reports, vol. 5, pp. 1-12, Oct. 27, 2015.
Tanowitz et al., Asialoglycoprotein Receptor 1 Mediates Productive Uptake of N-Acetylgalactosamine-Conjugated and Unconjugated Phosphorothioate Antisense Oligonucleotides into Liver Hepatocytes, Nucleic Acids Research, vol. 45, No. 21, pp. 12388-12400, Dec. 1, 2017.
Teng et al., "A GDF15 3' UTR variant, rs1054564, results in allele-specific translational repression of GDF15 by hsa-miR-1233-3p", PLoS One, Aug. 2017, 12(8): e0183187, 15 pages.
Thompson et al., Toxicological and Pharmacokinetic Properties of Chemically Modified siRNAs Targeting p53 RNA Following Intravenous Administration, Nucleic Acid Therapeutics, vol. 22, No. 4, pp. 255-264, Aug. 1, 2012.
Vickers, et al., Development of a Quantitative BRET Affinity Assay for Nucleic Acid-protein Interactions, PLoS One, vol. 11, No. 8, p. e0161930, pp. 1-17, Aug. 29, 2016.
Wanke et al., Overgrowth of Skin in Growth Hormone Transgenic Mice Depends on the Presence of Male Gonads, Journal of Investigative Dermatology, vol. 113, pp. 967-971, Dec. 1, 1999.
Whitehead et al., Degradable Lipid Nanoparticles with Predictable in Vivo siRNA Delivery Activity, Nature Communications, vol. 5, pp. 1-10, Jun. 27, 2014.

(56) References Cited

OTHER PUBLICATIONS

Wickstrom, Oligodeoxynucleotide Stability in Subcellular Extracts and Culture Media, Journal of Biochemical and Biophysical Methods, vol. 13, Issue 2, pp. 97-102, Sep. 1986.
Yamana, et al., 2'-Pyrene Modified Oligonucleotide Provides a Highly Sensitive Fluorescent Probe of RNA, Nucleic Acids Research, 1999, 27(11): 2387-2392.
Yekta, et al., MicroRNA-Directed Cleavage of HOXB8 mRNA, Science, Apr. 23, 2004, 304(5670): 594-596.
Zamore, et al., Ancient Pathways Programmed by Small RNAs, Science, May 17, 2002, 296(5571): 1265-1269.
Zhou et al., Nanoparticle-based Delivery of RNAi Therapeutics: Progress and Challenges, Pharmaceuticals, vol. 6, pp. 85-107, Jan. 2013.
Zimmermann et al., Clinical Proof of Concept for a Novel Hepatocyte-Targeting GalNAc-siRNA Conjugate, Molecular Therapy, vol. 25, Issue 1, pp. 71-78, Jan. 4, 2017.
Zlatev, et al., Reversal of siRNA-mediated Gene Silencing in Vivo, Nature Biotechnology, vol. 36, No. 6, pp. 509-511, 2018.
U.S. Appl. No. 15/089,423 2016/0319278, filed Apr. 1, 2016 Nov. 3, 2016, Anastasia Khvorova, Fully Stabilized Asymmetric siRNA.
U.S. Appl. No. 15/691,120 2017/0369882, filed Aug. 30, 2017 Dec. 28, 2017, Anastasia Khvorova, Fully Stabilized Asymmetric siRNA.
U.S. Appl. No. 16/927,543 2021/0024926, filed Jul. 13, 2020 Jan. 28, 2021, Anastasia Khvorova, Fully Stabilized Asymmetric siRNA.
U.S. Appl. No. 15/236,051 2017/0043024 U.S. Pat. No. 10,633,653, filed Aug. 12, 2016 Feb. 16, 2017 Apr. 28, 2020, Anastasia Khvorova, Bioactive Conjugates for Oligonucleotide Delivery.
U.S. Appl. No. 16/812,714 2020/0339983, filed Mar. 9, 2020 Oct. 29, 2020, Anastasia Khvorova, Bioactive Conjugates for Oligonucleotide Delivery.
U.S. Appl. No. 15/419,593 2017/0312367 U.S. Pat. No. 10,478,503, filed Jan. 30, 2017 Nov. 2, 2017 Nov. 19, 2019, Anastasia Khvorova, Branched Oligonucleotides.
U.S. Appl. No. 16/390,712 2019/0247507 U.S. Pat. No. 10,799,591, filed Apr. 22, 2019 Aug. 15, 2019 Oct. 13, 2020, Anastasia Khvorova, Branched Oligonucleotides.
U.S. Appl. No. 17/012,787 2021/0085793, filed Sep. 4, 2020 Mar. 25, 2021, Anastasia Khvorova, Branched Oligonucleotides.
U.S. Appl. No. 16/322,212 2019/0185855, filed Jan. 31, 2019 Jun. 20, 2019, Anastasia Khvorova, Conjugated Oligonucleotides.
U.S. Appl. No. 16/015,440 2019/0024082 U.S. Pat. No. 10,844,377, filed Jun. 22, 2018 Jan. 24, 2019 Nov. 24, 2020, Anastasia Khvorova, Two-Tailed Self-Delivering siRNA.
U.S. Appl. No. 17/071,473 2021/0139901, filed Oct. 15, 2020 May 13, 2021, Anastasia Khvorova, Two-Tailed Self-Delivering siRNA.
U.S. Appl. No. 16/537,374 2020/0123543, filed Aug. 9, 2019 Apr. 23, 2020, Anastasia Khvorova, Modified Oligonucleotides Targeting SNPs.
U.S. Appl. No. 16/988,391 2021/007117, filed Aug. 7, 2020 Mar. 11, 2021, Anastasia Khvorova, Modified Oligonucleotides Targeting SNPs.
U.S. Appl. No. 16/746,555 2020/0270605 U.S. Pat. No. 11,492,619, filed Jan. 17, 2020 Aug. 27, 2020 Nov. 8, 2022, Anastasia Khvorova, Dynamic Pharmacokinetic-Modifying Anchors.
U.S. Appl. No. 17/792,705 2023/0061751, filed Jul. 13, 2022 Mar. 2, 2023, Anastasia Khvorova, Universal Dynamic Pharmacokinetic-Modifying Anchors.
U.S. Appl. No. 16/550,076 2020/0087663 U.S. Pat. No. 11,279,930, filed Aug. 23, 2019 Mar. 19, 2020 Mar. 22, 2022, Anastasia Khvorova, O-Methyl Rich Fully Stabilized Oligonucleotides.
U.S. Appl. No. 16/999,759 2021/0115442, filed Aug. 21, 2020 Apr. 22, 2021, Anastasia Khvorova, O-Methyl Rich Fully Stabilized Oligonucleotides.
U.S. Appl. No. 17/580,269 2022/0251555, filed Jan. 20, 2022 Aug. 11, 2022, Anastasia Khvorova, O-Methyl Rich Fully Stabilized Oligonucleotides.
U.S. Appl. No. 17/022,678 2021/0108200, filed Sep. 16, 2020 Apr. 15, 2021, Anastasia Khvorova, Branched Lipid Conjugates of siRNA for Specific Tissue Delivery.
U.S. Appl. No. 17/235,153 2021/0355491, filed Apr. 20, 2021 Nov. 18, 2021, Anastasia Khvorova, Oligonucleotides for MSH3 Modulation.
U.S. Appl. No. 17/331,146 2021/0395739, filed May 26, 2021 Dec. 23, 2021, Anastasia Khvorova, Synthetic Oligonucleotides Having Regions of Block and Cluster Modifications.
U.S. Appl. No. 17/391,475 2022/0090069, filed Aug. 2, 2021 Mar. 24, 2022, Anastasia Khvorova, Oligonucleotides for HTT-1A Modulation.
U.S. Appl. No. 17/377,632 2022/0042015, filed Jul. 16, 2021 Feb. 10, 2022, Anastasia Khvorova, Conjugated Oligonucleotides for Tissue Specific Delivery.
U.S. Appl. No. 17/846,526 2023/0078622, filed Jun. 22, 2022 Mar. 16, 2023, Anastasia Khvorova, Optimized ANTI-FLT1 Oligonucleotides Compounds for Treatment of Preeclampsia and Other Angiogenic Disorders.
Extended European Search Report for European Patent Application No. 20856904.6, mailed Jan. 2, 2024.
Extended European Search Report for European Patent Application No. 21741867.2, mailed Mar. 12, 2024.
Godinho et al., "PK-modifying anchors significantly alter clearance kinetics, tissue distribution, and efficacy of therapeutics siRNAs", Mol Ther Nucleic Acids, Jun. 13, 2022,29: 116-132, ePublished Sep. 13, 2022.
Jo et al., "Small Interfering RNA Nunchucks with a Hydrophobic Linker for Efficient Intracellular Delivery", Macromol Biosci., 2014, 14: 195-201.
Smith et al., "RNA Nanotherapeutics for the Amelioration of Astroglial Reactivity", Mol Ther Nucleic Acids, Mar. 2, 2018, 10: 103-121, ePublished Nov. 24, 2017.
Tai et al., "Current Aspects of siRNA Bioconjugate for in Vitro and in Vivo Delivery", Molecules, Jun. 2019, 24(12): 2211, ePublished Jun. 13, 2019.
Zhou et al., "Functional in Vivo Delivery of Multiplexed Anti-HIV-1 siRNAs via a Chemically Synthesized Aptamer with a Sticky Bridge", Mol Ther., Jan. 2013, 21(1): 192-200.
Bertram et al., "Vinylphosphonate Internucleotide Linkages Inhibit the Activity of PcrA DNA Helicase", Biochemistry, Jun. 18, 2002, 41(24): 7725-7731.
Dua et al., "Modified siRNA Structure With a Single Nucleotide Bulge Overcomes Conventional siRNA-mediated Off-target Silencing", Molecular Therapy, Jun. 2011, 16(9): 1676-1687.
Extended Supplementary European Search Report for European Patent Application No. 20777915.8, mailed Sep. 15, 2023.
Flower et al., MSH3 Modifies Somatic instability and Disease Severity in Huntington's and Myotonic Dystrophy Type 1, Brain, A Journal of Neurology, Jul. 2019, 142(7): 1876-1886.
Ghosh et al., "Comparing 2-nt 3' overhangs against blunt-ended siRNAs: a systems biology based study", BMC Genomics, 2009, 10(Suppl. 1):S17.
Harlow et al., "Antibodies: A Laboratory Manual", Cold Spring Harbor Laboratory Chapter 14, Second Edition, 2013.
International Search Report & Written Opinion Received for PCT Application No. PCT/US2021/028166, mailed on Nov. 26, 2021.
International Search Report & Written Opinion Received for PCT Application No. PCT/US2021/044158, dated Jan. 31, 2022.
International Search Report & Written Opinion Received for PCT Application No. PCT/US2022/039047, dated Mar. 3, 2023.
Khorev et al., Trivalent, Gal//GalNAc-containing ligands designed for the asialoglycoprotein receptor, Bioorgan. & Medicin. Chem., 2008, 16: 5216-5231.
Lee et al., A Novel Approach to Investigate Tissue-specific Trinucleotide Repeat Instability, BMC Systems Biology, Mar. 19, 2010, 4(29): 1-16.
Lee et al., Adeno-associated virus (AAV) vectors: Rational design strategies for capsid engineering, Current Opinion in Biomed. Eng., 2018, 58-63.
Miller et al., Adaptable Synthesis of C-Glycosidic Multivalent Carbohydrates and Succinamide-Linked Derivization, Org. Letter., 2010, 12(22): 5262-5265.
Moss et al., Identification of Genetic Variants Associated with Huntington's Disease Progression: A Genome-wide Association Study, The Lancet, Neurology, Sep. 2017, 16(9): 701-711.

(56) References Cited

OTHER PUBLICATIONS

Namjou et al., "GWAS and enrichment analyses of non-alcoholic fatty liver disease identify new trait-associated genes and pathways across eMERGE Network", BMC Medicine, Jul. 2019, 17: 135, 19 pages.
Noguchi et al., "Allele-specific Gene Silencing of Mutant mRNA Restores Cellular Function in Ullrich Congenital Muscular Dystrophy Fibroblasts", Molecular Therapy—Nucleic Acids, Jun. 2014, 3: e171.
Oishi et al., "Lactosylated Poly(ethylene glycol)-siRNA Conjugate through Acid-Labile B-Thiopropionate Linkage to Construct pH-Sensitive Polyion Complex Micelles Achieving Enhanced Gene Silencing in Hepatoma Cells", J. Am. Chem. Soc., 2005, 127: 1624-1625.
Old et al., "Cloning in Yeast and Microbial Eukaryotes", Principles of Gene Manipulation: An Introduction to Genetic Engineering, Studies in Microbiology, 1989, 2(11): 199-221.
Østergaard et al., "Conjugation of hydrophobic moieties enhances potency of antisense oligonucleotides in the muscle of rodents and non-human primates", Nucleic Acids Research, 2019, 47(12): 6045-6058.
Partial Supplementary European Search Report for European Patent Application No. 20852443.9, mailed Aug. 25, 2023.
Partial Supplementary European Search Report for European Patent Application No. 20856904.6, mailed Sep. 13, 2023.
Schwarz et al., "Designing siRNA that distinguish between genes that differ by a single nucleotide", PLOS Genetics, Sep. 2006, 2(9): e140.
Sibley et al., "Identification of Allele-Specific RNAi Effectors Targeting Genetic Forms of Parkinson's Disease", PLOS One, Oct. 2011, 6(10): e26194.
Supplementary European Search Report for European Patent Application No. 20856904.6, mailed Jan. 2, 2024.
Tome et al., MSH3 Polymorphisms and Protein Levels Affect CAG Repeat Instability in Huntington's Disease Mice, PLOS Genetics, Feb. 28, 2013, 9(2): e1003280, 1-16.
You et al., "Design of LNA probes that improve mismatch discrimination", Nucleic Acids Research, May 2006, 34(8): e60, 11 pages.
Zeng et al., "RNA Interference in human cells is restricted to the cytoplasm", RNA, Jul. 1, 2002, 8(7): 855-860.
U.S. Appl. No. 15/089,319 2016/0355808 U.S. Pat. No. 9,809,817, filed Apr. 1, 2016 Dec. 8, 2016 Nov. 7, 2017, Anastasia Khvorova, Oligonucleotides Compounds for Targeting Huntingtin mRNA.
U.S. Appl. No. 15/697,120 2018/0094263 U.S. Pat. No. 10,435,688, filed Sep. 6, 2017 Apr. 5, 2018 Oct. 8, 2019, Anastasia Khvorova, Oligonucleotides Compounds for Targeting Huntingtin mRNA.
U.S. Appl. No. 16/263,200 2019/0225965 U.S. Pat. No. 10,744,327, filed Jan. 31, 2019 Jul. 25, 2019 Sep. 15, 2020, Anastasia Khvorova, Oligonucleotides Compounds for Targeting Huntingtin mRNA.
U.S. Appl. No. 16/811,580 2020/0308584 U.S. Pat. No. 11,230,713, filed Mar. 6, 2020 Oct. 1, 2020 Jan. 5, 2022, Anastasia Khvorova, Oligonucleotides Compounds for Targeting Huntingtin mRNA.
U.S. Appl. No. 17/536,647 2022/0251554, filed Nov. 29, 2021 Aug. 11, 2022, Anastasia Khvorova, Oligonucleotides Compounds for Targeting Huntingtin mRNA.
U.S. Appl. No. 15/089,437 2016/0355826 U.S. Pat. No. 9,862,952, filed Apr. 1, 2016 Dec. 8, 2016 Jan. 9, 2018, Anastasia Khvorova, Oligonucleotides Compounds for Treatment of Preeclampsia and Other Angiogenic Disorders.
U.S. Appl. No. 15/814,350 2018/0179546 U.S. Pat. No. 10,519,451, filed Nov. 15, 2017 Jun. 28, 2018 Dec. 31, 2019, Anastasia Khvorova, Oligonucleotides Compounds for Treatment of Preeclampsia and Other Angiogenic Disorders.
U.S. Appl. No. 16/675,369 2020/0165618 U.S. Pat. No. 11,345,917, filed Nov. 6, 2019 May 28, 2020 May 11, 2022, Anastasia Khvorova, Oligonucleotides Compounds for Treatment of Preeclampsia and Other Angiogenic Disorders.
U.S. Appl. No. 17/718,918 2022/0364100, filed Apr. 12, 2022 Nov. 17, 2022, Anastasia Khvorova, Oligonucleotides Compounds for Treatment of Preeclampsia and Other Angiogenic Disorders.
U.S. Appl. No. 17/012,787 2021/0085793 U.S. Pat. No. 11,896,669, filed Sep. 4, 2020 Mar. 25, 2021 Feb. 13, 2024, Anastasia Khvorova, Branched Oligonucleotides.
U.S. Appl. No. 18/396,613, filed Dec. 26, 2023, Anastasia Khvorova, Branched Oligonucleotides.
U.S. Appl. No. 16/322,212 2019/0185855 U.S. Pat. No. 11,753,638, filed Jan. 31, 2019 Jun. 20, 2019 Sep. 12, 2023, Anastasia Khvorova, Conjugated Oligonucleotides.
U.S. Appl. No. 18/170,167, filed Feb. 16, 2023, Anastasia Khvorova, Conjugated Oligonucleotides.
U.S. Appl. No. 16/537,374 2020/0123543 U.S. Pat. No. 11,827,882, filed Aug. 9, 2019 Apr. 23, 2020 Nov. 28, 2023, Anastasia Khvorova, Modified Oligonucleotides Targeting SNPs.
U.S. Appl. No. 16/988,391 2021/0071177, filed Aug. 7, 2020 Mar. 11, 2021, Anastasia Khvorova, Modified Oligonucleotides Targeting SNPs.
U.S. Appl. No. 18/446,929, filed Aug. 9, 2023, Anastasia Khvorova, Modified Oligonucleotides Targeting SNPs.
U.S. Appl. No. 18/421,647, filed Jan. 24, 2024, Anastasia Khvorova, Modified Oligonucleotides Targeting SNPs.
U.S. Appl. No. 18/430,581, filed Feb. 1, 2024, Anastasia Khvorova, Oligonucleotides for HTT-1A Modulation.

FIG. 3
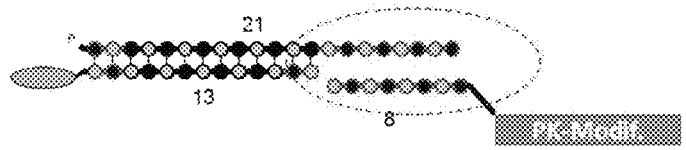
Hydrophilic Polycarbonates
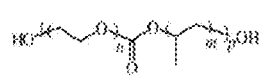
Block co-polymers
    Amphiphilic block-co polymers
    Hydrophilic block-co-polymers
    poloxamers
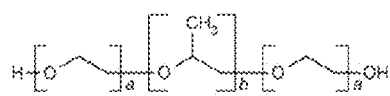
Polyetheylene Glycol
Polysaccharides:
    Dextrins
    Chitosan
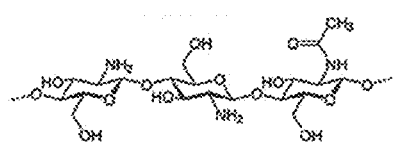

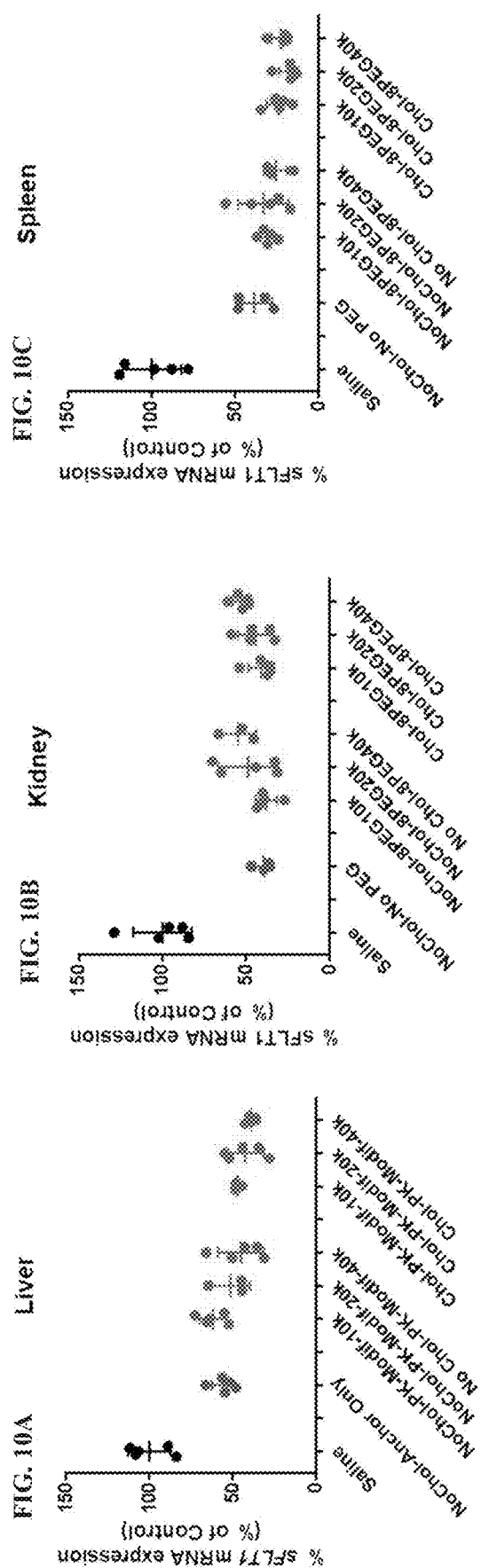

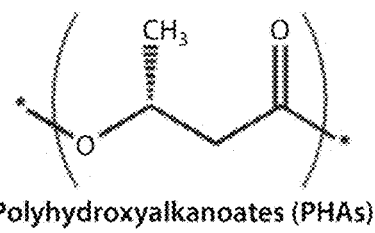 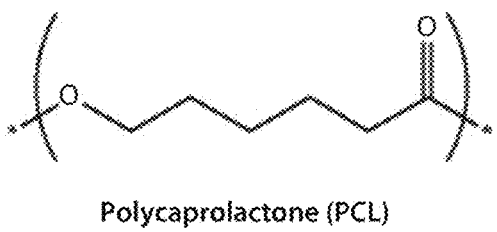
Polyhydroxyalkanoates (PHAs)       Polycaprolactone (PCL)
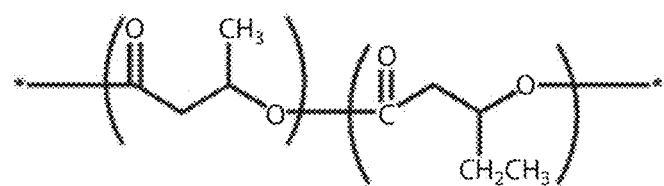 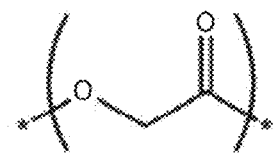
Poly (hydroxybutyrate-hydroxyvalerate)       Poly (glycolic acid) (PGA)
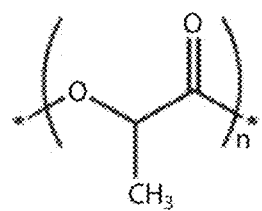
Poly (lactic acid) (PLA)
FIG. 13

Unconjugated Asymmetric siRNA
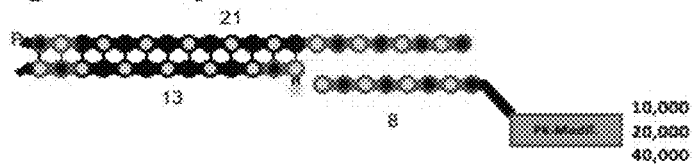
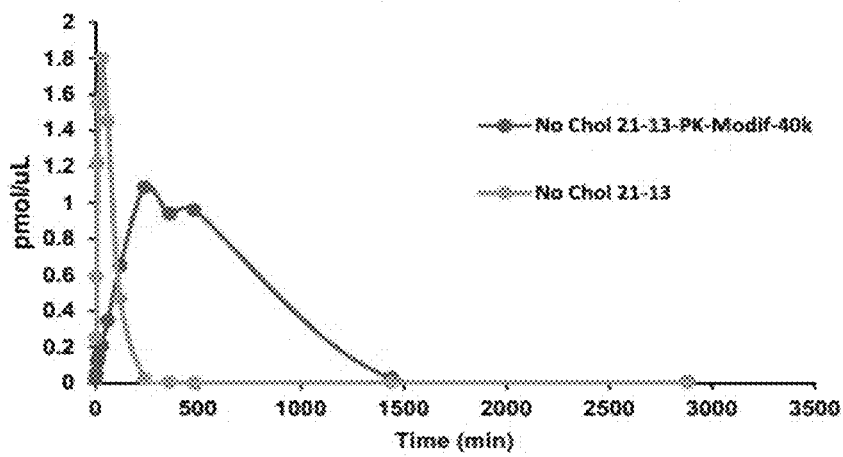
Lipid-conjugated Asymmetric siRNA
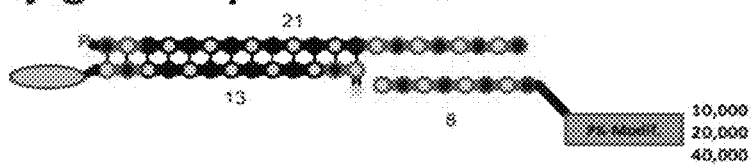
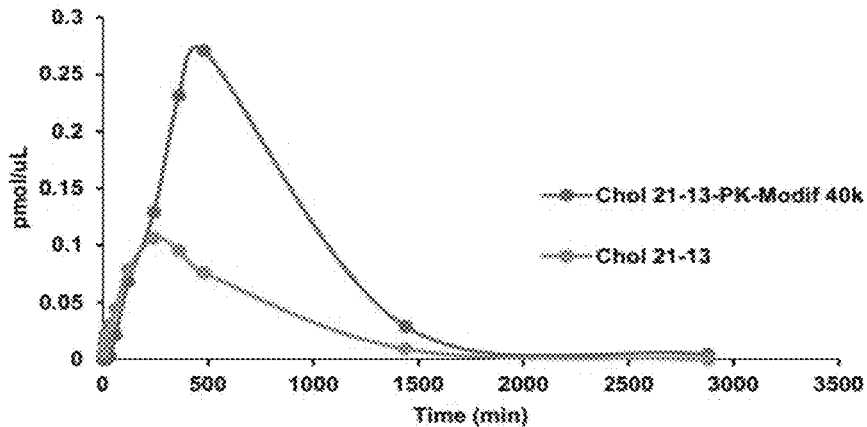
FIG. 28

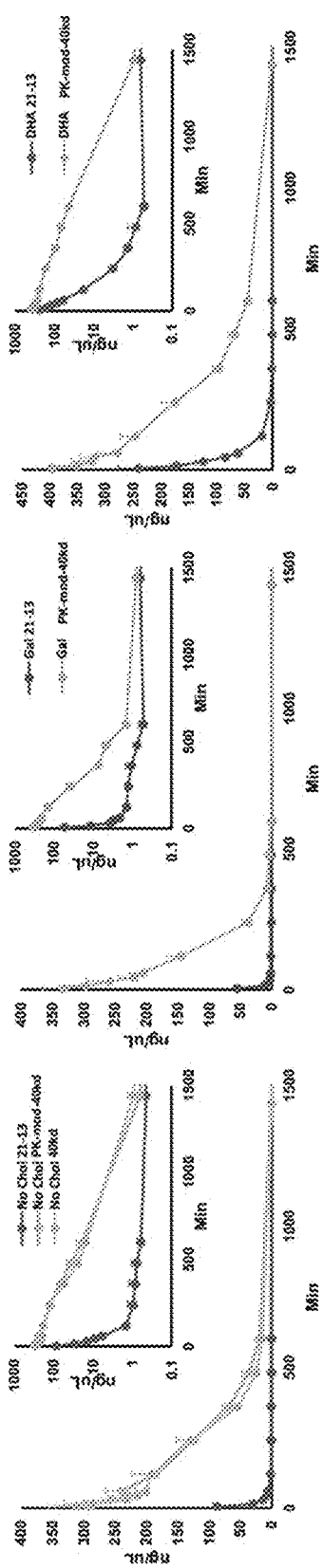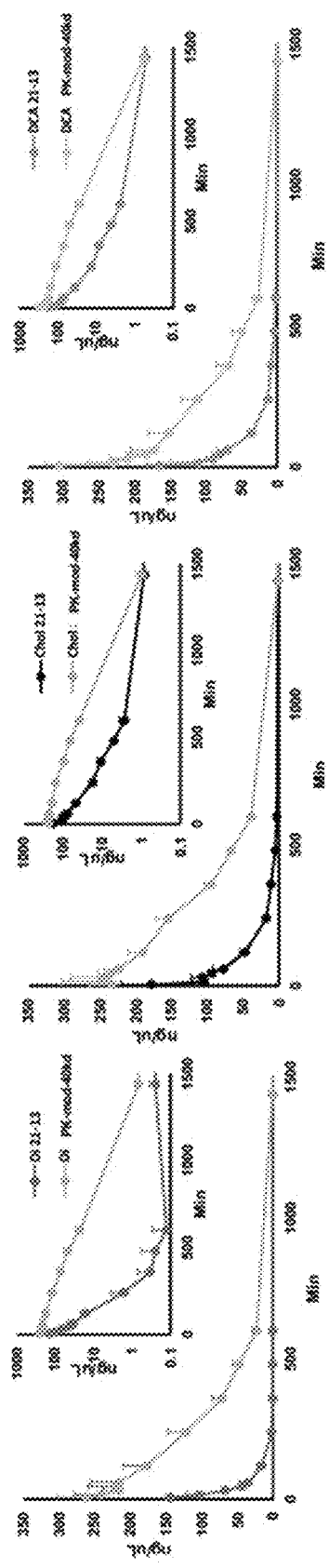
FIG. 32A  FIG. 32B  FIG. 32C
FIG. 32D  FIG. 32E  FIG. 32F

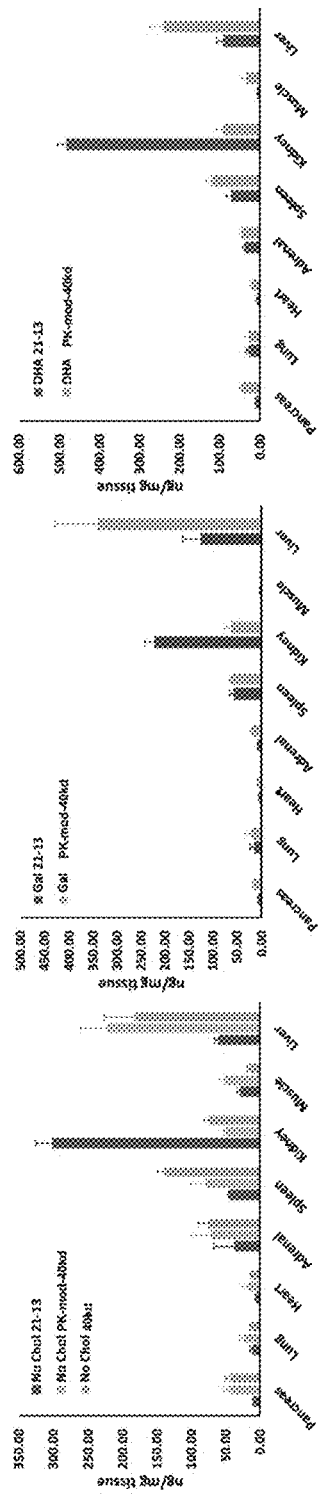
FIG. 33A
FIG. 33B
FIG. 33C
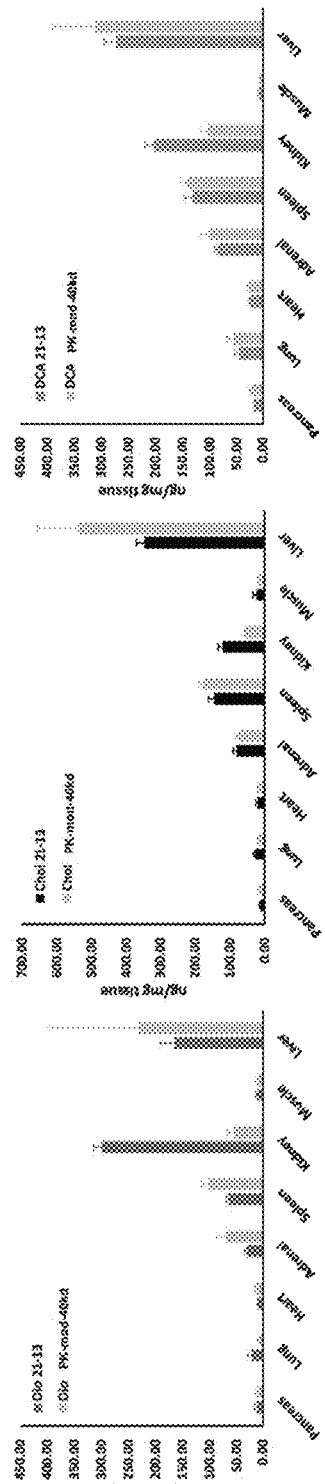
FIG. 33D
FIG. 33E
FIG. 33F

FIG. 40 cont.

DYNAMIC PHARMACOKINETIC-MODIFYING ANCHORS

CROSS-REFERENCE TO RELATED APPLICATION

This application is a divisional of U.S. patent application Ser. No. 16/746,555, filed Jan. 17, 2020, now U.S. Pat. No. 11,492,619, which claims the benefit of U.S. Provisional Application Ser. No. 62/794,123, filed Jan. 18, 2019, the entire disclosures of which are hereby incorporated herein by reference.

STATEMENT REGARDING FEDERALLY FUNDED RESEARCH

This invention was made with government support under grant numbers NS104022, HD086111 and OD020012 awarded by the National Institutes of Health. The Government has certain rights in the invention.

TECHNICAL FIELD

This disclosure relates to compounds comprising novel oligonucleotide-based pharmacokinetic (PK)-modifying anchors with useful applications for RNA interference (RNAi) and other gene therapy technologies. The PK-modifying anchors described herein are patterned to enable efficient modulation of absorption, distribution and clearance kinetics of therapeutic oligonucleotides to enhance their tissue distribution. Efficient modulation of the absorption, distribution and clearance kinetics can be achieved in blood/plasma, cerebrospinal fluid (CSF) and other relevant bodily/biological fluids and tissues.

BACKGROUND

Oligonucleotides are cleared very quickly after cerebrospinal fluid (CSF) injection, with less than 1-2% of the injected dose being retained in the brain and spinal cord. One of the well-understood problems with use of oligonucleotide therapeutics in central nervous system applications is rapid CSF clearance. In rodents, bolus injection is sufficient to support wide oligonucleotide distribution in large brains, and bulk CSF flow is a primary mechanism behind distribution. Rapid CSF clearance limits distribution of oligonucleotides to deep structures of the brain, and is a primary limitation of this platform for the treatment of many neurodegenerative disorders.

Similarly, when administered IV or SC, oligonucleotides are rapidly removed systemically by elimination through the kidney filtration or via the reticuloendothelial system. Retention in secondary tissues beyond liver, kidney, bone marrow and spleen is a real challenge in the field.

There remains a need for self-delivering siRNA that is characterized by efficient RISC entry, minimum immune response and off-target effects, efficient cellular uptake without formulation, improved absorption, distribution and clearance kinetics, and efficient, specific or functional tissue distribution.

SUMMARY

The present invention is based on the discovery of compounds comprising novel platform, dynamic pharmacokinetic ("PK")-modifying anchors, where the anchors enable efficient modulation of the absorption, distribution, and clearance kinetics of component therapeutic oligonucleotides in blood/plasma, CSF, and other bodily/biological fluids and tissues. A panel of block co-polymers (e.g., poloxamer 188 and the like) are provided herein that function as non-immunogenic PK modifiers and which are compatible with oligonucleotide chemistry.

In one aspect, the disclosure provides a compound comprising: a first oligonucleotide, wherein the first oligonucleotide comprises at least 16 contiguous nucleotides, a 5' end, a 3' end; and a pharmacokinetic (PK)-modifying anchor comprising an anchor oligonucleotide, an optional linker and at least one polymer, wherein the anchor oligonucleotide comprises or consists of about 5 to about 15 nucleotides that are complementary to the first oligonucleotide, and wherein the polymer is at least about 2,000 Da.

In certain embodiments, the anchor oligonucleotide is about 5 to about 15 nucleotides in length, or about 5 to about 10 nucleotides in length.

In certain embodiments, the polymer is operably linked to the anchor oligonucleotide via the optional linker.

In certain embodiments, the compound comprises formula (I):

wherein:
O is the first oligonucleotide;
L is a linker, and is present or absent;
$X^c$ is selected from the group consisting of a hydrophobic moiety, a sugar, a peptide, an aptamer and a nucleic acid, and is present or absent; and
Z is the PK-modifying anchor.

In certain embodiments, the first oligonucleotide is selected from the group consisting of an antisense oligonucleotide (ASO), a synthetic miRNA, a synthetic mRNA, a single-stranded siRNA and a modified CRISPR guide strand.

In certain embodiments, the ASO is a splice-switching ASO or an RNase H ASO.

In certain embodiments, the first oligonucleotide comprises complementarity to a target.

In certain embodiments, the first oligonucleotide comprises perfect complementarity to a target.

In certain embodiments, L comprises an ethylene glycol chain, an alkyl chain, a peptide, RNA, DNA, a phosphodiester, a phosphorothioate, a phosphoramidate, an amide, a carbamate, or a combination thereof.

In certain embodiments, $X^c$ is selected from the group consisting of a fatty acid, a steroid, a secosteroid, a lipid, a ganglioside, a nucleoside analog, and an endocannabinoid. In certain embodiments, $X^c$ comprises an N-Acetylgalactosamine (GalNAc) moiety or a derivative thereof. In certain embodiments, $X^c$ has an affinity for one or both of a low-density lipoprotein and an intermediate density lipoprotein. In certain embodiments, $X^c$ is a saturated or unsaturated moiety having fewer than three double bonds. In certain embodiments, $X^c$ has an affinity for high density lipoprotein. In certain embodiments, $X^c$ is a polyunsaturated moiety having three or more double bonds.

In certain embodiments, the at least one polymer is selected from the group consisting of a hydrophobic polycarbonate, a polyester, an amphiphilic block copolymer, a hydrophobic block polymer, a polysaccharide and a polypeptide. In certain embodiments, the hydrophobic polycarbonate is poly(DTR carbonate). In certain embodiments, the polyester is selected from the group consisting of a polyhydroxyalkanoate, a polycaprolactone, a poly(hyroxybuterate-hydroxyvalerate), a polyglycolic acid and a polylactic acid. In certain embodiments, the amphiphilic block copolymer is selected from the group consisting of polyvinylpyrrolidone, poly(2-ethyl-2-oxazoline), acrylonitrile styrene acrylate, N-(2-hydroxypropyl) methacrylamide and polyethylene glycol (PEG). In certain embodiments, the hydrophobic block copolymer is selected from the group consisting of poly(N,N-dimethylacrylamide), poly(N,N-diethylaniline), poly(diphenylamine) and poly(tetrahydrofurfuryl methacrylate). In certain embodiments, the polysaccharide is selected from the group consisting of a soluble polyglucose, a non-soluble polyglucose, cellulose, glycogen and amylopectin. In certain embodiments, the polypeptide is a polylysine, a polyarginine, a polyalanine, a polyisoleucine, a polymethionine, a polyphenylalanine, a polyvaline, a polyproline and a polyglycine and any combinations thereof. In certain embodiments, the PEG has a molecular weight selected from the group consisting of about 10,000 Da, about 20,000 Da, about 40,000 Da, about 60,000 Da, about 80,000 Da and about 100,000 Da.

In certain embodiments, the PK-modifying anchor comprises more than one polymer. In certain embodiments, the PK-modifying anchor comprises 2, 3 or 4 polymers.

In certain embodiments, the first oligonucleotide comprises 21, 22, 23, 24, 25, 26, 27 or 28 nucleotides and the polymer is PEG.

In certain embodiments, the first oligonucleotide comprises one or more chemically-modified nucleotides. In certain embodiments, the first oligonucleotide is fully chemically-modified or partially chemically-modified. In certain embodiments, the first oligonucleotide comprises one or more locked nucleic acids (LNAs) or one or more peptide nucleic acids (PNAs). In certain embodiments, the first oligonucleotide comprises one or more S-constrained-ethyls (cETs). In certain embodiments, the first oligonucleotide comprises about 50% 2'-methoxy-ribonucleotides, about 55% 2'-methoxy-ribonucleotides, about 60% 2'-methoxy-ribonucleotides, about 65% 2'-methoxy-ribonucleotides, about 70% 2'-methoxy-ribonucleotides, about 75% 2'-methoxy-ribonucleotides, about 80% 2'-methoxy-ribonucleotides, about 85% 2'-methoxy-ribonucleotides, about 90% 2'-methoxy-ribonucleotides, about 95% 2'-methoxy-ribonucleotides, about 96% 2'-methoxy-ribonucleotides, about 97% 2'-methoxy-ribonucleotides, about 98% 2'-methoxy-ribonucleotides, about 99% 2'-methoxy-ribonucleotides or about 100% 2'-methoxy-ribonucleotides. In certain embodiments, the first oligonucleotide comprises alternating 2'-methoxy-ribonucleotides and 2'-fluoro-ribonucleotides. In certain embodiments, the nucleotides of the first oligonucleotide are connected via phosphodiester linkages, phosphorothioate linkages or a combination of phosphodiester and phosphorothioate linkages.

In certain embodiments, (1) the first oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide, and the nucleotides at positions 2 and 14 from the 5' end of the first oligonucleotide are not 2'-methoxy-ribonucleotides; and (2) the nucleotides of the first oligonucleotide are connected to adjacent nucleotides via phosphodiester or phosphorothioate linkages, wherein the nucleotides at positions 1-6 from the 3' end, or positions 1-7 from the 3' end are connected to adjacent nucleotides via phosphorothioate linkages.

In certain embodiments, the compound further comprises a second oligonucleotide comprising at least 12 contiguous nucleotides, a 5' end, a 3' end; and wherein a portion of the first oligonucleotide is complementary to a portion of the second oligonucleotide.

In certain embodiments, the second oligonucleotide comprises a conjugate moiety, $X^c$. In certain embodiments, the second oligonucleotide is attached to $X^c$ with a linker, L. In certain embodiments, L comprises an ethylene glycol chain, an alkyl chain, a peptide, RNA, DNA, a phosphodiester, a phosphorothioate, a phosphoramidate, an amide, a carbamate, or a combination thereof. In certain embodiments, $X^c$ is attached at the 5' end, at the 3' end, at an internal position, or a mixture thereof of the second oligonucleotide. In certain embodiments, $X^c$ is attached at the 3' end of the second oligonucleotide. In certain embodiments, $X^c$ is selected from the group consisting of a fatty acid, a steroid, a secosteroid, a lipid, a ganglioside, a nucleoside analog, and an endocannabinoid. In certain embodiments, $X^c$ comprises an N-Acetylgalactosamine (GalNAc) moiety or a derivative thereof. In certain embodiments, $X^c$ has an affinity for one or both of a low-density lipoprotein and an intermediate density lipoprotein.

In certain embodiments, $X^c$ is a saturated or unsaturated moiety having fewer than three double bonds. In certain embodiments, $X^c$ has an affinity for high density lipoprotein. In certain embodiments, $X^c$ is a polyunsaturated moiety having three or more double bonds.

In certain embodiments, the anchor oligonucleotide is perfectly complementary to the first oligonucleotide. In certain embodiments, the anchor oligonucleotide contains one, two, three or four mismatches relative to the first oligonucleotide.

In certain embodiments, anchor oligonucleotide comprises one or more chemically-modified nucleotides. In certain embodiments, the anchor oligonucleotide is fully chemically-modified or partially chemically-modified. In certain embodiments, the anchor oligonucleotide comprises one or more locked nucleic acids (LNAs) or one or more peptide nucleic acids (PNAs). In certain embodiments, the anchor oligonucleotide comprises one or more S-constrained-ethyls (cETs). In certain embodiments, the anchor oligonucleotide comprises alternating 2'-O-methyl ribonucleotides and 2'-fluoro ribonucleotides. In certain embodiments, the anchor oligonucleotide comprises alternating 2'-O-methyl ribonucleotides and 2'-fluoro ribonucleotides and at least two adjacent phosphorothioate internucleotide linkages at a 5' end and a 3' end. In certain embodiments, the anchor oligonucleotide comprises alternating 2'-O-methyl ribonucleotides and 2'-fluoro ribonucleotides and phosphorothioate internucleotide linkages at every nucleotide position. In certain embodiments, the anchor oligonucleotide comprises at least two adjacent 2',4'-constrained 2'O-ethyl bridged nucleic acids at a 5' end and a 3' end. In certain embodiments, the anchor oligonucleotide comprises a 2',4'-constrained 2'O-ethyl bridged nucleic acids at every nucleotide position and phosphorothioate internucleotide linkages between each adjacent nucleotide. In certain embodiments, the anchor oligonucleotide comprises alternating 2'-O-methyl ribonucleotides and 2'-fluoro ribonucleotides and at least two 2',4'-constrained 2'O-ethyl bridged nucleic acids at a 5' end and a 3' end. In certain embodiments, the anchor oligonucleotide comprises a peptide nucleic acid at every nucleotide position.

In certain embodiments, the anchor oligonucleotide is attached to the polymer at a 5' end, at a 3' end, at an internal position, or a mixture thereof.

In certain embodiments, at least two of the oligonucleotides are cross-linked.

In certain embodiments, the compound further comprises a nanoparticle, an intercalating agent, a polycation, or a mixture thereof.

In certain embodiments, a) the first oligonucleotide is between 21 nucleotides to 25 nucleotides in length; b) the second oligonucleotide is between 13 nucleotides and 17 nucleotides in length; and c) the anchor oligonucleotide is between 5 nucleotides and 8 nucleotides in length.

In certain embodiments, a) the first oligonucleotide is 21 nucleotides in length; b) the second oligonucleotide is 13 nucleotides in length; and c) the anchor oligonucleotide is 8 nucleotides in length.

In certain embodiments, a) the first oligonucleotide is 23 nucleotides in length; b) the second oligonucleotide is 15 nucleotides in length; and c) the anchor oligonucleotide is 8 nucleotides in length.

In certain embodiments, a) the first oligonucleotide is 25 nucleotides in length; b) the second oligonucleotide is 17 nucleotides in length; and c) the anchor oligonucleotide is 8 nucleotides in length.

In certain embodiments, the polymer comprises PEG.

In certain embodiments, the PK-modifying anchor influences stability of an oligonucleotide therapeutic agent over time in a body part comprising, a heart, a kidney, a liver, a spleen, an adrenal gland, a pancreas, a lung, blood, plasma, a brain, or a mixture thereof, wherein the effect comprises a change in volume of distribution, area under curve, clearance, half-life maximum concentration, bioavailability, or a mixture thereof.

In certain embodiments, the number of nucleotides in the first oligonucleotide comprises a same number of nucleotides in the second oligonucleotide and anchor oligonucleotide combined. In certain embodiments, the number of nucleotides in the first oligonucleotide comprises a greater number of nucleotides than in the second oligonucleotide and anchor oligonucleotide combined. In certain embodiments, the number of nucleotides in the first oligonucleotide comprises a lesser number of nucleotides than in the second oligonucleotide and anchor oligonucleotide combined.

In one aspect, the disclosure provides a compound comprising: a first oligonucleotide, wherein the first oligonucleotide is 21 nucleotides in length, with a 5' end, a 3' end, and is complementary to a target; a second oligonucleotide, wherein the second oligonucleotide is 13 nucleotides in length, with a 5' end, a 3' end, and is complementary to nucleotides 1-13 of the first oligonucleotide; and an anchor oligonucleotide, wherein the anchor oligonucleotide is 8 nucleotides in length, with a 5' end, a 3' end, and is complementary nucleotides 14-21 of the first oligonucleotide, wherein the second oligonucleotide is attached to a molecule comprising cholesterol, dichloroacetate, docosahexaenoic acid, or N-acetylgalactosamine at a 3' end, wherein the anchor oligonucleotide is attached to a polyethylene glycol polymer comprising a molecular weight of between 10,000 and 40,000 Daltons, and wherein the first oligonucleotide comprises complementarity to both the second oligonucleotide and the anchor oligonucleotide to form the asymmetric duplex.

In certain embodiments, the compound further comprises a pharmaceutically active carrier.

In another aspect, the disclosure provides a pharmaceutical composition comprising the compound described above and a pharmaceutically acceptable carrier.

In another aspect, the disclosure provides a method for treating a disease or disorder in a patient in need thereof, comprising administering to the patient a compound described above.

In one aspect, the disclosure provides a method of treating a patient having a disease or disorder comprising administering an asymmetric oligonucleotide duplex comprising an first oligonucleotide, a second oligonucleotide, and an anchor oligonucleotide wherein the anchor oligonucleotide comprises a pharmacokinetic-modifying moiety and wherein the first oligonucleotide can pair with both the second oligonucleotide and the anchor oligonucleotide to form the asymmetric oligonucleotide duplex.

In one aspect, the disclosure provides a method of delivering a compound to the liver of a subject, comprising administering to the subject a compound comprising: a first oligonucleotide, wherein the first oligonucleotide comprises at least 16 contiguous nucleotides, a 5' end, a 3' end, and comprises complementarity to a target; a second oligonucleotide comprising at least 12 contiguous nucleotides, a 5' end, a 3' end, wherein a portion of the first oligonucleotide is complementary to a portion of the second oligonucleotide, and wherein the second oligonucleotide comprises an N-Acetylgalactosamine (GalNAc) moiety or a derivative thereof; and a pharmacokinetic (PK)-modifying anchor comprising an anchor oligonucleotide, an optional linker and at least one polymer, wherein the anchor oligonucleotide comprises about 5 to about 15 nucleotides that are complementary to the first oligonucleotide, and wherein the polymer is at least about 2,000 Da.

In one aspect, the disclosure provides an asymmetric duplex comprising a first oligonucleotide strand, a second oligonucleotide strand, and an anchor oligonucleotide strand wherein each oligonucleotide strand comprises at least one chemically-modified nucleotide, wherein the anchor oligonucleotide strand comprises a pharmacokinetic-modifying moiety, wherein the second oligonucleotide strand and the anchor oligonucleotide strand each comprise fewer nucleotides than the first oligonucleotide strand, and wherein the first oligonucleotide strand can pair with both the second oligonucleotide strand and the anchor oligonucleotide strand to form the asymmetric duplex.

In certain embodiments, the first oligonucleotide strand comprises 10-50 nucleotides, wherein the second oligonucleotide strand comprises 10-50 nucleotides, and wherein the anchor oligonucleotide comprises 5-15 nucleotides.

In certain embodiments, the first oligonucleotide strand and second oligonucleotide strand form an siRNA or dsRNA having a duplex region. In certain embodiments, the duplex region is about 10 to about 50 base pairs in length. In certain embodiments, the duplex region is about 10 to about 15, about 10 to about 20, about 10 to about 25, or about 10 to about 30 base pairs in length. In certain embodiments, the duplex region is 13, 14, 15, 16, 17, or 18 base pairs.

In certain embodiments, the first oligonucleotide strand is at least 16 nucleotides in length, wherein the second oligonucleotide strand is at least 11 nucleotides in length, and wherein the anchor oligonucleotide is about 5-15 nucleotides in length. In certain embodiments, the first oligonucleotide strand is about 21-23 nucleotides in length, wherein the second oligonucleotide strand is about 13-16 nucleotides in length, and wherein the anchor oligonucleotide is about 5-10 nucleotides in length. In certain embodiments, the first oligonucleotide strand is 21 nucleotides in length, wherein the second oligonucleotide strand is 13 nucleotides in length, and wherein the anchor oligonucleotide is 8 nucleotides in length.

In certain embodiments, the at least one chemically-modified nucleotide comprises a 2'-O-methyl-ribonucleotide, a 2'-fluoro-ribonucleotide, a phosphorothioate internucleotide linkage, a locked nucleic acid, a 2',4'-constrained 2'O-ethyl bridged nucleic acid, a peptide nucleic acid, or a mixture thereof.

In certain embodiments, the second oligonucleotide strand comprises a ligand attached at a 5' end, at a 3' end, at an internal position, or a mixture thereof.

In certain embodiments, the ligand of the second strand comprises a lipid, a lipophile, a terpene, a sugar, a peptide, a protein, an alkyl chain, a lectin, a glycoprotein, a hormone, drug, a carbohydrate, an antibody, an aptamer, a vitamin, a cationic dye, a bioactive conjugate, a porphyrin, a polycyclic aromatic hydrocarbon, a synthetic polymer, or a mixture thereof. In certain embodiments, the ligand of the second strand comprises a fatty acid, a steroid, a secosteroid, a polyamine, a ganglioside, a nucleoside analog, an endocannabinoid, an omega-3 fatty acid, an omega-6 fatty acid, an omega-9 fatty acid, a conjugated linolenic acid, a saturated fatty acid, or a mixture thereof. In certain embodiments, the ligand of the second strand comprises cholesterol, docosahexaenoic acid, conjugated phosphatidylcholine, N-acetylgalactosamine, dichloroacetic acid, epithelial cell adhesion molecule aptamer, cholic acid, adamantane acetic acid, 1-pyrene butyric acid, dihydrotestosterone, 1,3-Bis-O(hexadecyl)glycerol, geranyloxyhexyl group, hexadecylglycerol, borneal, menthol, 1,3-propanediol, heptadecyl group, palmitic acid, myristic acid, 03-(oleoyl)lithocholic acid, 03-(oleoyl)cholenic acid, dimethoxytrityl, phenoxazine, or a mixture thereof.

In certain embodiments, the second strand further comprises a linker attaching the ligand to the second strand.

In one aspect, the disclosure provides an asymmetric duplex comprising a first oligonucleotide strand 21 nucleotides in length, a second oligonucleotide strand 13 nucleotides in length, and an anchor oligonucleotide strand 8 nucleotides in length, wherein each oligonucleotide strand comprises alternating 2'-fluoro-ribonucleotides and 2'-methoxy-ribonucleotides, wherein the first strand comprises two adjacent phosphorothioate internucleotide linkages at a 5' end and eight adjacent phosphorothioate internucleotide linkages at a 3' end, wherein the second oligonucleotide strand comprises two adjacent phosphorothioate internucleotide linkages at a 5' end and two adjacent phosphorothioate internucleotide linkages at a 3' end and a linker attached to a molecule comprising cholesterol, dichloroacetate, docosahexaenoic acid, or N-acetylgalactosamine at a 3' end, wherein the anchor oligonucleotide strand comprises seven adjacent phosphorothioate internucleotide linkages at a 5' end and a linker at a 3' end attached to a pharmacokinetic-modifying moiety comprising a polyethylene glycol polymer comprising a molecular weight of between 10,000 and 40,000 Daltons, and wherein the first oligonucleotide strand can pair with both the second oligonucleotide strand and the anchor oligonucleotide strand to form the asymmetric duplex.

In one aspect, the disclosure provides a method of treating a patient having a disease or disorder comprising administering an asymmetric oligonucleotide duplex comprising an first oligonucleotide strand, a second oligonucleotide strand, and an anchor oligonucleotide strand wherein the anchor oligonucleotide strand comprises a pharmacokinetic-modifying moiety and wherein the first oligonucleotide strand can pair with both the second oligonucleotide strand and the anchor oligonucleotide strand to form the asymmetric oligonucleotide duplex.

In one aspect, the disclosure provides an asymmetric hairpin duplex comprising a hairpin oligonucleotide strand and an anchor oligonucleotide strand wherein the hairpin oligonucleotide strand comprises an overhang and can pair with the anchor oligonucleotide strand to form the asymmetric hairpin duplex and wherein the anchor oligonucleotide strand comprises a pharmacokinetic-modifying moiety.

In one aspect, the disclosure provides a pharmaceutical composition comprising an asymmetric oligonucleotide duplex comprising a first oligonucleotide strand, a second oligonucleotide strand, and an anchor oligonucleotide strand wherein the anchor oligonucleotide strand comprises a pharmacokinetic-modifying moiety and wherein the first oligonucleotide strand can pair with both the second oligonucleotide strand and the anchor oligonucleotide strand to form the asymmetric oligonucleotide duplex.

In one aspect, the disclosure provides a universal anchor oligonucleotide of about 5-8 nucleotides in length and a pharmacokinetic-modifying moiety at a 5' end, wherein at least one nucleotide comprises a chemical modification, wherein the anchor oligonucleotide can bind an asymmetric oligonucleotide duplex comprising a first oligonucleotide strand, a second oligonucleotide strand, and wherein the sequence of the oligonucleotide anchor is complementary to a region at a 3' end of the first oligonucleotide strand.

In certain embodiments, the first strand and the anchor strand comprise a GC content of between about 35 to about 100%.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings.

FIG. 3 schematically depicts exemplary embodiments of PK-modifying moieties including hydrophilic polycarbonates, block co-polymers (e.g., amphiphilic block co-polymers, hydrophilic block co-polymers or poloxamers), polyethylene glycol and polysaccharides (e.g., dextrins or chitosan).

FIG. 7 schematically depicts a cholesterol-conjugated siRNA and a delivery system. A suitable delivery system includes, but is not limited to, a lipid nanoparticle, an exosome, a microvesicle or the like.

FIG. 10A-FIG. 10C depict the effect of PK-modifying anchors on the delivery of hsiRNA compounds after intravenous injection as measured by mRNA expression. mRNA expression was tested in liver (FIG. 10A), kidney (FIG. 10B) and spleen (FIG. 10C). 20 mg/kg tail vein injections were performed in female FVB/N mice (at approximately 9-12 weeks old). Tissues were collected at 48 hours after injection and mRNA expression was quantified using a QuantiGene b-DNA assay.

In FIG. 11A, 4 nmols (or about 250 µg) of hsiRNA was injected in the lateral ventriculum to result in a concentration of about 2 nmol/ventricle. In FIG. 11B, 20 nmol of hsiRNA was injected in the lateral ventriculum to result in a concentration of about 10 nmol/ventricle. The distribution of hsiRNA in mouse brain is shown in FIG. 11A and FIG. 11B. In FIG. 11C, 10 nmol of hsiRNA was injected between L5 and L6 by intrathecal injection. The distribution of hsiRNA in mouse spine is shown in FIG. 11C. Mouse brains and spine tissues were collected 48 hours post-injection and stained with DAPI (nuclei, blue). Brains and tissues were imaged using a Leica DMi8 Fluorescent Microscope.

FIG. 13 depicts polyester polymers according to certain exemplary embodiments.

FIG. 20 depicts kidney distribution after subcutaneous (SC) administration.

FIG. 26 schematically depicts dynamic oligonucleotide anchors for use in the delivery of other classes of nucleotides, e.g., ASOs (shown as compatible, for example, with RNase H or splice switching), microRNAs, mRNAs, CRISPR guide strands and the like.

FIG. 28A-FIG. 28B graphically depict that PK modifying anchors dynamically improved blood/plasma circulating times of parent hsiRNA compounds. PK modifying anchors enhanced areas under the curve of (FIG. 28A) unconjugated and (FIG. 28B) cholesterol-conjugated hsiRNAs after subcutaneous injections. PK modifying anchors delayed time to peak and efficiently slow the clearance kinetics of parent hsiRNA compounds. 20 mg/kg tail vein injections were performed in female FVB/N mice (~9-12 weeks old). The antisense strand was quantified by peptide nucleic acid (PNA) hybridization assay as previously described in Godinho et al. (2017) Nucleic Acids Therapeutics. Briefly this assay uses a cy3-labelled PNA probe that hybridizes to the antisense strand, with subsequent quantification by HPLC. AUC was calculated using the model-independent trapezoidal method with GastroPlus, Simulations Plus. Polyethylene glycol (PEG) was used as a model PK modifying moiety, and a fully phosphorothioated 8-mer was used as a model anchor to modulate circulating times of the respective parent as21-s13 compound. Both PK modifying moiety and length and chemistry of the anchor may be adjusted according to the delivery aim/goal.

FIG. 32A-FIG. 32F depict the blood concentration profile of PK-modifying anchors paired with a panel asymmetric siRNA duplex structures, as depicted in FIG. 31. Polyethylene glycol (PEG) was used as the PK-modifying polymer. The siRNA asymmetric duplex contained a 21-mer oligonucleotide antisense strand and a 13-mer oligonucleotide sense strand. A fully phosphorothioated 8-mer oligonucleotide anchor was used. 20 mg/kg tail vein injections performed in female FVB/N mice (at approximately 9-12 weeks old). The antisense strand was quantified using a peptide nucleic acid hybridization assay after 48 hours. Blood concentration levels of siRNAs are shown for unconjugated siRNAs (FIG. 32A), GalNAc-conjugated siRNAs (FIG. 32B), DHA-conjugated siRNAs (FIG. 32C), Di-branched siRNAs (FIG. 32D), cholesterol-conjugated siRNAs (FIG. 32E), and DCA-conjugated siRNAs (FIG. 32F).

FIG. 33A-FIG. 33F depict the tissue distribution profile of PK-modifying anchors paired with a panel asymmetric siRNA duplex structures, as depicted in FIG. 31. Polyethylene glycol (PEG) was used as the PK-modifying polymer. The siRNA asymmetric duplex contained a 21-mer oligonucleotide antisense strand and a 13-mer oligonucleotide sense strand. A fully phosphorothioated 8-mer oligonucleotide anchor was used. 20 mg/kg tail vein injections performed in female FVB/N mice (at approximately 9-12 weeks old). The antisense strand was quantified using a peptide nucleic acid hybridization assay after 48 hours. Blood concentration levels of siRNAs are shown for unconjugated siRNAs (FIG. 33A), GalNAc-conjugated siRNAs (FIG. 33B), DHA-conjugated siRNAs (FIG. 33C), Di-branched siRNAs (FIG. 33D), cholesterol-conjugated siRNAs (FIG. 33E), and DCA-conjugated siRNAs (FIG. 33F).

FIG. 38A depicts liver distribution, FIG. 38B depicts spleen distribution, and FIG. 38C depicts kidney distribution.

DETAILED DESCRIPTION

Figure 1:
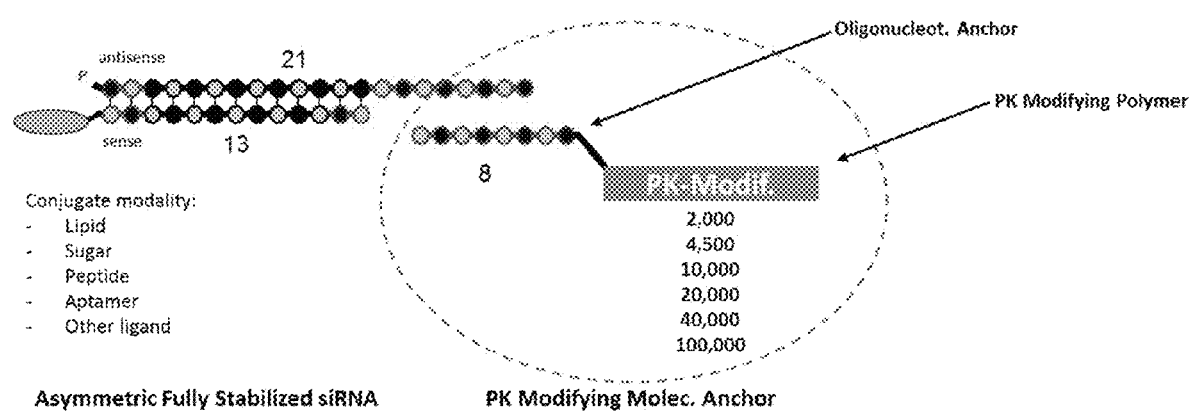
FIG. 1 schematically depicts the chemical structure of an asymmetric siRNA according to certain exemplary embodiments. In a non-limiting example, the hydrophobically modified siRNA (hsiRNA) depicted here consists of an asymmetric duplex formed by a 21 oligonucleotide (21-mer) antisense strand and a 13-mer sense strand comprising a hydrophobic cholesterol moiety. The asymmetric hsiRNA further comprises a complementary oligonucleotide anchor (e.g., 8-mer) having a pharmacokinetic (PK)-modifying polymer attached thereto. The complementary oligonucleotide anchor (e.g., 8-mer) hybridizes with the complementary antisense strand. 2'-O-methyl is depicted in black, 2'-fluoro is depicted in grey, and phosphorothioate bonds are depicted with a red dash.

The present disclosure relates to therapeutic oligonucleotides (e.g., therapeutic siRNAs) that comprise pharmacokinetic (PK)-modifying anchors. Therapeutic oligonucleotides comprising PK-modified anchors as provided herein efficiently modulate the absorption, distribution and clearance kinetics in relevant bodily/biological fluids (e.g. cerebrospinal fluid and plasma) and other tissues. PK modifying anchors enable functional delivery to a range of tissues, such as, e.g., heart, kidney, liver, spleen, adrenal, pancreatic, lung, blood (e.g., plasma) and brain tissues.

Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting. As used herein, unless otherwise stated, the singular forms "a," "an," and "the" include plural reference. Thus, for example, a reference to "a protein" includes a plurality of protein molecules.

Generally, nomenclatures used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

As used herein, the term "pharmacokinetic-modifying" or "PK-modifying" refers to a compound that can be used to modify the concentration of a therapeutic agent (e.g., an RNAi agent) over time. In certain embodiments, a PK-modifying agent effects stability of a therapeutic agent in one or more locations (e.g., in the heart, kidney, liver, spleen, adrenal, pancreatic, lung, blood (e.g., plasma) and/or brain tissue) in a subject. Altered PK parameters include, but are not limited to, volume of distribution ($V_d$), area under the curve (AUC), clearance (CL), half-life ($t_{1/2}$), maximum concentration ($C_{max}$), bioavailability (F) and the like.

As used herein, the term "pharmacokinetic-modifying anchor," "PK-modifying anchor" or "Z" refers to a construct comprising an oligonucleotide anchor attached to a polymer via an optional linker. The oligonucleotide anchor of Z can be complementary to an oligonucleotide, e.g., an overhang of a double-stranded nucleic acid sequence or a portion of a single-stranded nucleic acid sequence. The polymer can be attached to an oligonucleotide, e.g., an overhang of a double-stranded nucleic acid sequence or a portion of a single-stranded oligonucleotide, via hybridization of the oligonucleotide anchor. The polymer portion of Z can comprise a PK-modifying moiety.

In certain embodiments, a polymer described herein (e.g., a PK modifying polymer) is directly attached to an oligonucleotide anchor (e.g., without a separate linker).

In certain embodiments, an oligonucleotide anchor is attached to a polymer via a linker that provides a functional group whereby the polymer is attached to the oligonucleotide anchor. In certain embodiments, the linker can be an alkyl chain, e.g., from about one carbon up to about 25 carbons, or a well-defined propylene or ethylene glycol chain, e.g., from about 1 to about 25 units. Exemplary linkers are:

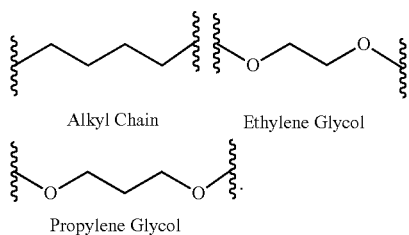

Alkyl Chain    Ethylene Glycol

Propylene Glycol

In certain embodiments, the oligonucleotide anchor of Z has a GC content of between about 35% and about 100% when hybridized to a target oligonucleotide. In certain embodiments, the oligonucleotide anchor of Z has a GC content about 35%, about 40%, about 45%, about 50%, about 55%, about 60%, about 65%, about 70%, about 75%, about 80%, about 85%, about 95%, about 96%, about 97%, about 98%, about 99% or about 100% when hybridized to a target oligonucleotide.

In certain embodiments, a target oligonucleotide comprises a fixed or conserved region at its 3' end that is complementary to a fixed or conserved region of an oligonucleotide anchor. In certain embodiments, the fixed or conserved region of a target oligonucleotide is fully complementary to, partially complementary to, or not complementary to a target mRNA.

In certain exemplary embodiments, Z comprises more than one polymer. In certain exemplary embodiments, Z comprises 1, 2, 3, 4, 5, 6, 7, 8, 9, or 10 polymers. In certain exemplary embodiments, Z comprises 2, 3, 4, or more polymers.

In certain exemplary embodiments, Z contains a polymer moiety that varies in molecular weight from about 2,000 Daltons (Da) to about 100,000 Da, including all values in between. In certain exemplary embodiments, the molecular weight of a polymer is about 2,000 Da, about 2,500 Da, about 3,000 Da, about 3,500 Da, about 4,000 Da, about 4,500 Da, about 5,000 Da, about 5,500 Da, about 6,000 Da, about 6,500 Da, about 7,000 Da, about 7,500 Da, about 8,000 Da, about 8,500 Da, about 9,000 Da, about 9,500 Da or about 10,000 Da, including all values in between. In certain exemplary embodiments, the molecular weight of the polymer is about 10,000 Da, about 15,000 Da, about 20,000 Da, about 25,000 Da, about 30,000 Da, about 35,000 Da, about 40,000 Da, about 45,000 Da, about 50,000 Da, about 55,000 Da, about 60,000 Da, about 65,000 Da, about 70,000 Da, about 75,000 Da, about 80,000 Da, about 85,000 Da, about 90,000 Da, about 95,000 Da, or about 100,000 Da, including all values in between. In certain exemplary embodiments, the molecular weight of the polymer is about 2,000 Da, about 4,500 Da, about 10,000 Da, about 20,000 Da, about 40,000 Da, or about 100,000 Da.

In certain exemplary embodiments, a suitable polymer can comprise one or any combination of a hydrophilic polycarbonate, a polyethylene glycol (PEG), a block co-polymer (including, e.g., an amphiphilic or a hydrophilic block co-polymer), a poloxamer, a polysaccharide (including, e.g., a dextrin or a chitosan), and a poly(lactic-co-glycolic acid) (PLGA). Exemplary embodiments of suitable PK-modifying moieties are shown at FIG. 3.

In certain exemplary embodiments, a PK-modifying polymer is a hybrid polymer containing multiple types of polymer subunits. An exemplary hybrid polymer is a PEG-PolyPEPTIDE. (De Marre A, et al.: Synthesis, characterization, and in vitro biodegradation of poly(ethylene glycol) modified poly[5N-(2-hydroxyethyl-L-glutamine]. J Bioact Compat Polym 1996, 11:85-99. 76. Chen C, Wang Z, Li Z: Thermoresponsive polypeptides from pegylated poly-L-glutamates. Biomacromolecules 2011, 12:2859-2863.)

In certain exemplary embodiments, a polymer used in Z comprises PEG, e.g., one or any combination of PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, PEG-350, PEG-400, PEG-500, PEG-600, PEG-800, PEG-1000, PEG-1500, PEG-2000, PEG-4000, PEG-5000, PEG-6000, PEG-7000, PEG-8000, PEG-9000, PEG-14,000 PEG-20,000, PEG-23,000, PEG-25,000, PEG-45,000, PEG-65,000, PEG-90,000 and the like.

In certain exemplary embodiments, a polymer used in Z comprises a poloxamer. Suitable poloxamers include, but are not limited to, poloxamer 118, poloxamer 188, poloxamer 288, poloxamer 338, poloxamer 407, poloxamine 1107, or poloxamine 1307. The commercially available poloxamers Synperonics (Croda Healthcare), Pluronics (BASF), and Kolliphor (BASF) are also suitable.

Figure 12:
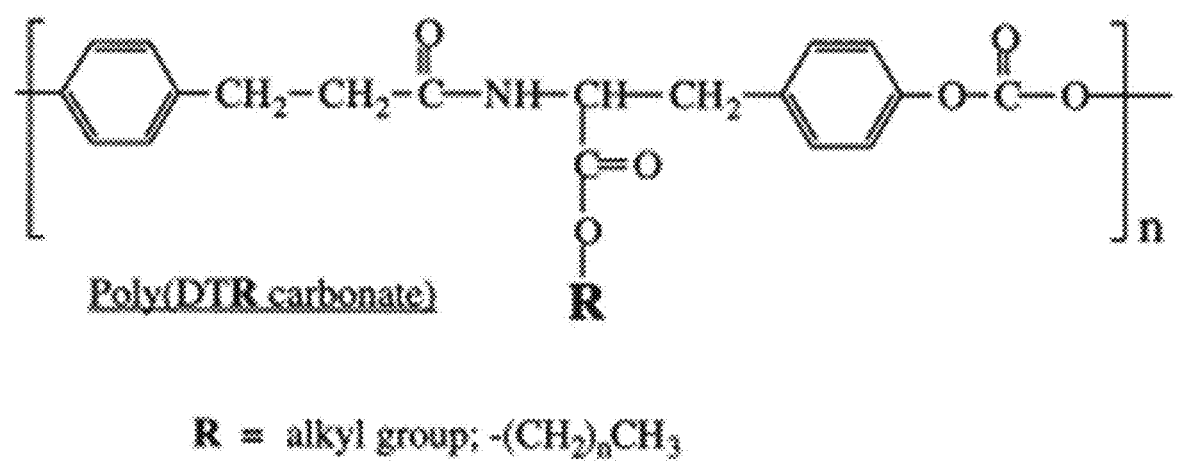
FIG. 12 depicts a hydrophobic polycarbonate polymer according to certain exemplary embodiments.

In certain exemplary embodiments, a polymer used in Z comprises a hydrophobic polycarbonate such as, e.g., a tyrosine-derived polycarbonate or the like (FIG. 12).

In certain exemplary embodiments, a polymer used in Z comprises a polyester such as, e.g., a polyhydroxyalkanoate (PHA), apolycaprolactone (PCL), a poly(hyroxybuterate-hydroxyvalerate), a poly glycolic acid (PGA), a poly lactic acid (PLA) or the like (FIG. 13).

Figure 14:
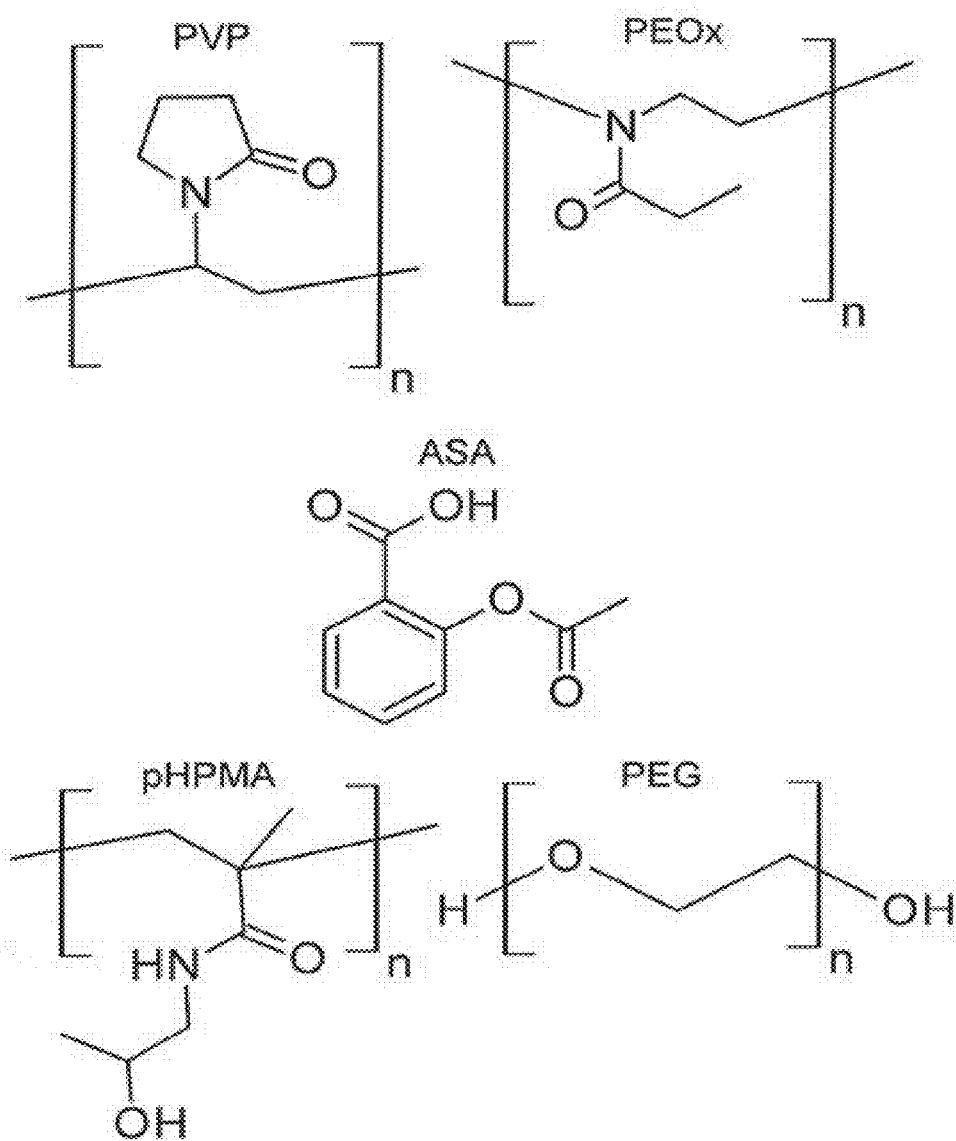
FIG. 14 depicts amphiphilic block copolymers according to certain exemplary embodiments.
Figure 15:
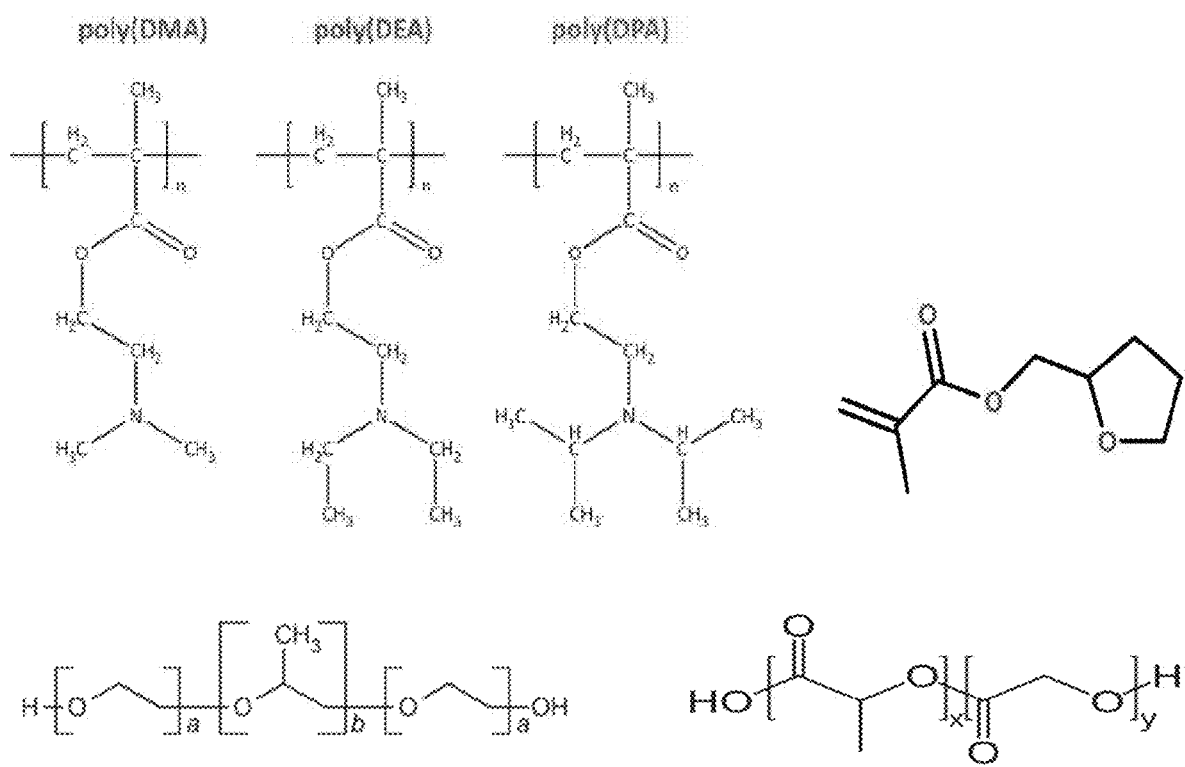
FIG. 15 depicts hydrophilic block copolymers according to certain exemplary embodiments.

In certain exemplary embodiments, a polymer used in Z comprises a block copolymer such as an amphiphilic block copolymer (e.g., poly(2-ethyl-2-oxazoline) (i.e., Aquazol), polyvinylpyrrolidone, acrylonitrile styrene acrylate, N-(2-hydroxypropyl) methacrylamide, polyethylene glycol or the like) (FIG. 14) or a hydrophilic block copolymer (e.g., poly(DMA), poly(DEA), poly(DPA), tetrahydrofurfuryl methacrylate, a poloxamer (e.g., poloxamer 188, poloxamer 407, poloxamer 338) or the like (FIG. 15).

Figure 16:
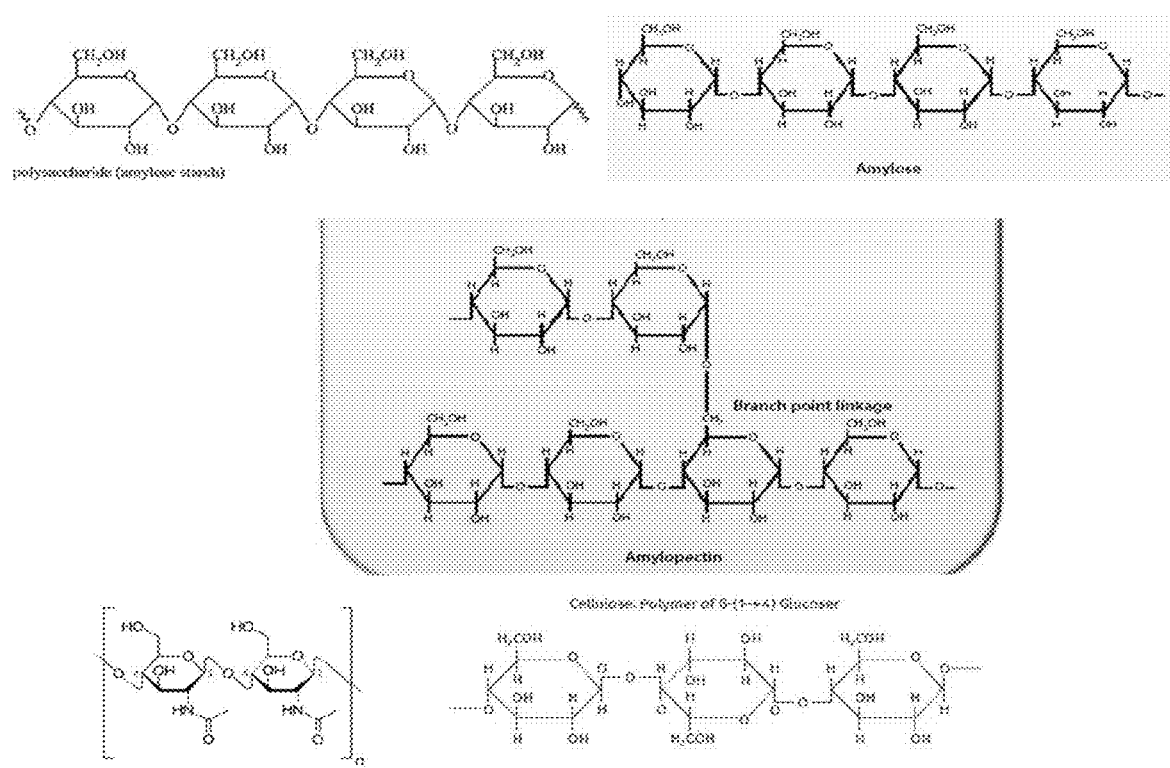
FIG. 16 depicts polysaccharide polymers according to certain exemplary embodiments.

In certain exemplary embodiments, a polymer used in Z comprises a polysaccharide, e.g., a polyglucose (e.g., a soluble starch, a non-soluble starch), a small cellulose, chitin, glycogen, amylose, amylopectin or the like (FIG. 16).

In certain exemplary embodiments, a polymer used in Z comprises a polypeptide, e.g., polylysine, polyarginine, or other positively charged or hydrophobic amino acids (e.g., a polyalanine, a polyisoleucine, a polymethionine, a polyphenylalanine, a polyvaline, a pol-proline, a polyglycine and the like, and any combinations thereof).

In certain exemplary embodiments, the melting point (Tm) of a nucleotide anchor is optimized to decrease clearance rate of an associated oligonucleotide. In certain exemplary embodiments, the Tm of the anchor is between about 37° C. to about 70° C., including all values in between. In certain exemplary embodiments, the Tm is about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 67° C., about 68° C. or about 70° C., including all values in between. In certain exemplary embodiments, the Tm is between about 37° C. and about 40° C., including all values in between. In certain exemplary embodiments, the Tm is between about 40° C. and about 45° C., including all values in between. In certain exemplary embodiments, the Tm is between about 45° C. and about 50° C., including all values in between. In certain exemplary embodiments, the Tm is between about 50° C. and about 55° C., including all values in between. In certain exemplary embodiments, the Tm is between about 55° C. and about 60° C., including all values in between.

Figure 5:
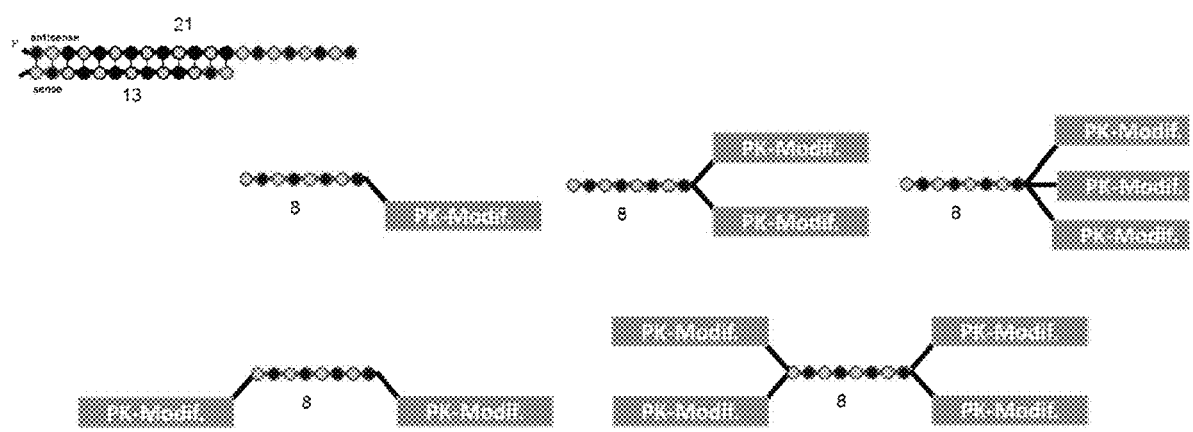
FIG. 5 schematically depicts exemplary configurations for attaching PK-modifying moieties to oligonucleotides. Branching patterns allow for the attachment of multiple PK-modifying polymers to each oligonucleotide anchor. siRNAs with 1, 2, 3 or 4 PK-modifying polymers are shown here.
Figure 6:
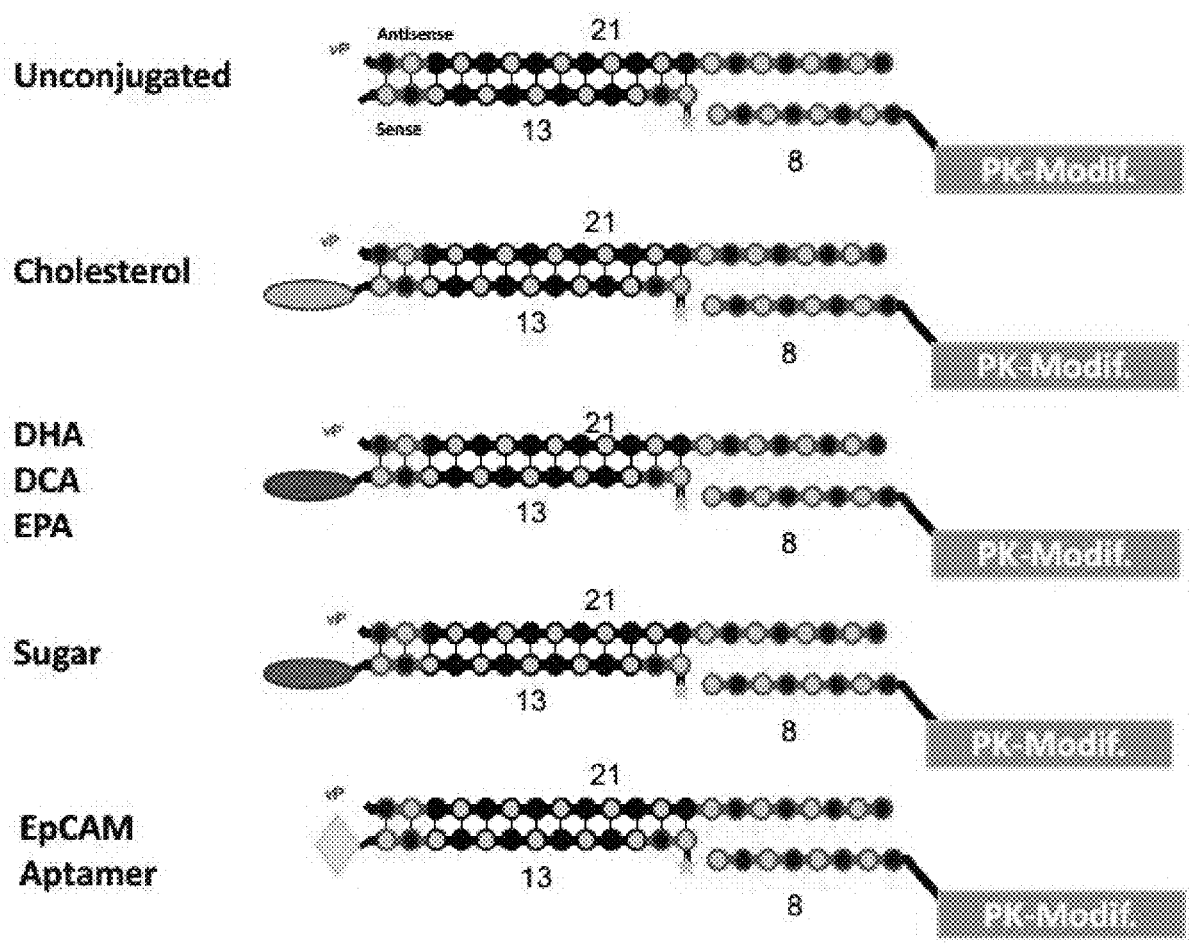
FIG. 6 schematically depicts asymmetric siRNAs that are either unconjugated or conjugated to a lipid. Exemplary lipids include, but are not limited to, cholesterol, docosahexaenoic acid conjugated phosphatidylcholine (PC-DHA), dichloroacetic acid (DCA), or epithelial cell adhesion molecule (EpCAM) aptamer.
Figure 7:
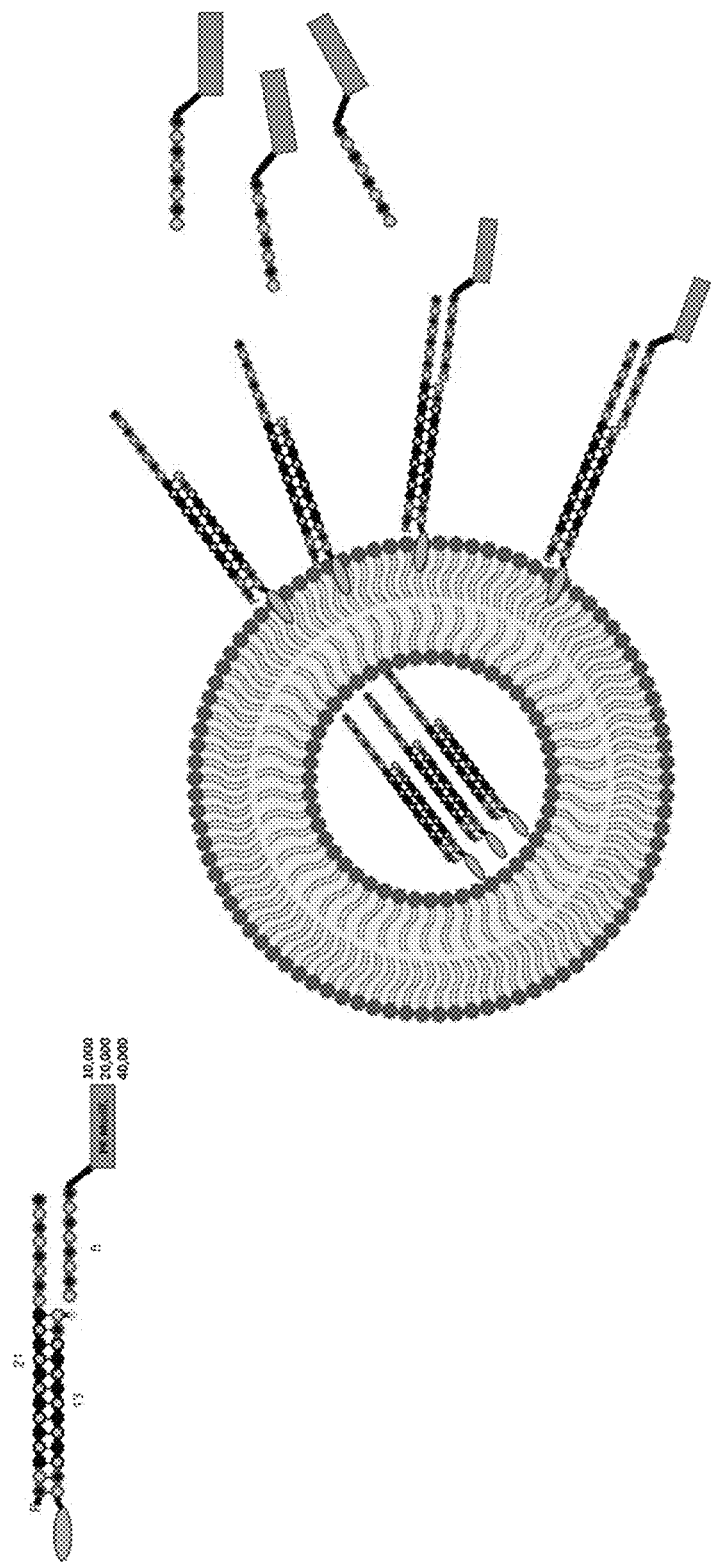

In certain exemplary embodiments, multiple PK-modifying polymers can be attached to a single-stranded oligonucleotide, a partially double-stranded oligonucleotide, or a fully double-stranded nucleic acid duplex. Exemplary embodiments are shown at FIG. 5, which depicts a variety of configurations that are useful for attaching PK-modifying polymers to an oligonucleotide anchor. In certain exemplary embodiments, PK-modifying polymers can be attached to both the 5' and the 3' ends of an oligonucleotide anchor. In certain exemplary embodiments, both the 3' and the 5' ends of an oligonucleotide anchor comprise multiple PK-modifying polymers. Certain exemplary embodiments include 1, 2 or 3 PK-modifying polymers attached to the 3' end, the 5' end, or both the 3' and the 5' ends of an oligonucleotide anchor.

In certain exemplary embodiments, Z modulates delivery of a branched oligonucleotide in which two or more double-stranded oligonucleotides are linked together. In certain embodiments, a PK-modifying polymer is attached to an oligonucleotide anchor of a double-stranded oligonucleotide. In such configurations, two or more PK-modifying anchors can be attached to the linked double-stranded oligonucleotides.

As used herein, the term "L" refers to a linker. L can be selected from the group consisting of an ethylene glycol chain, an alkyl chain, a peptide, RNA, DNA, a phosphodiester, a phosphorothioate, a phosphoramidate, an amide, and a carbamate, and any combinations thereof. In certain embodiments, L is attached to O via a second oligonucleotide. In certain embodiments, L is a divalent linker. In certain embodiments, L is a trivalent linker.

In a particular embodiment, L is the trivalent linker L1, also referred to herein as C7:

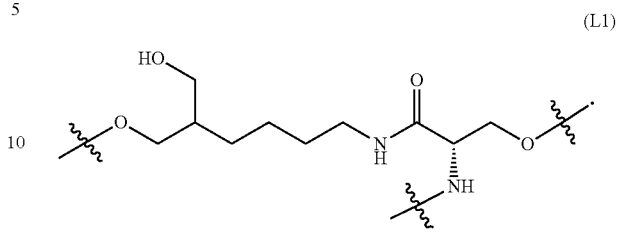

(L1)

In another particular embodiment, L is the divalent linker L2:

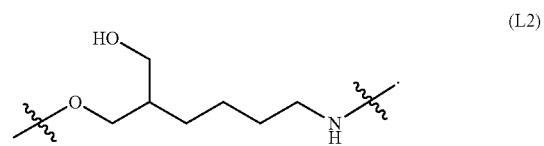

(L2)

In another particular embodiment, L is a trivalent or bivalent linker selected from the group consisting of:

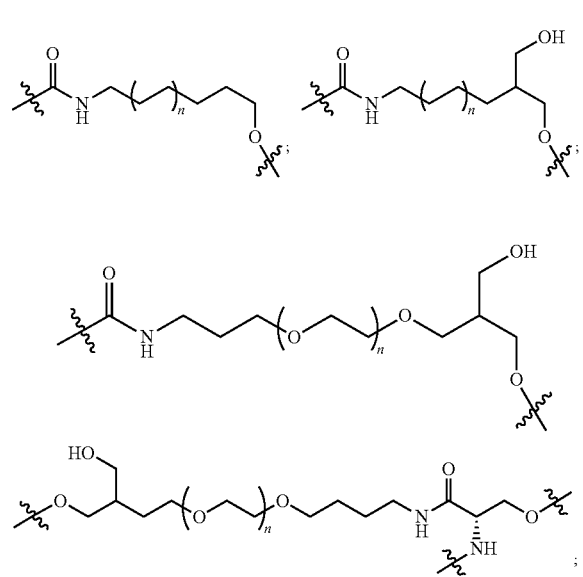

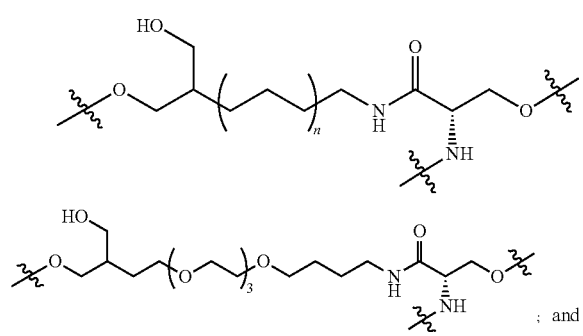

; and

-continued

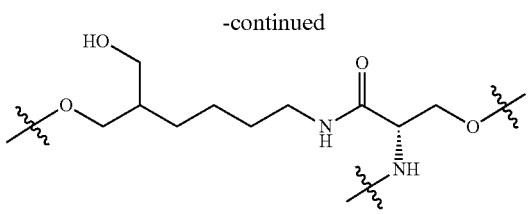

As used herein, the term "$X^c$" refers to a moiety that has an affinity for low density lipoprotein and/or intermediate density lipoprotein. In certain embodiments, $X^c$ is a saturated or unsaturated moiety having fewer than three double bonds. In certain embodiments, the term "$X^c$" may refer to a tethered ligand as described below in the "Tethered Ligands" section of the disclosure. In certain exemplary embodiments, $X^c$ comprises an N-Acetylgalactosamine (GalNAc) moiety or a derivative thereof In certain exemplary embodiments, $X^c$ has an affinity for high density lipoprotein. In a related embodiment, $X^c$ is a polyunsaturated moiety having at three or more double bonds (e.g., having three, four, five, six, seven, eight, nine or ten double bonds). In a particular embodiment, $X^c$ is a polyunsaturated moiety having three double bonds. In a particular embodiment, $X^c$ is a polyunsaturated moiety having four double bonds. In a particular embodiment, $X^c$ is a polyunsaturated moiety having five double bonds. In a particular embodiment, $X^c$ is a polyunsaturated moiety having six double bonds.

In certain exemplary embodiments, $X^c$ is selected from the group consisting of fatty acids, steroids, secosteroids, lipids, gangliosides and nucleoside analogs, and endocannabinoids.

In certain exemplary embodiments, $X^c$ is a neuromodulatory lipid, e.g., an endocannabinoid. Non-limiting examples of endocannabinoids include, but are not limited to, anandamide, arachidonoylethanolamine, 2-arachidonyl glyceryl ether (noladin ether), 2-arachidonyl glyceryl ether (noladin ether), 2-arachidonoylglycerol, and N-arachidonoyl dopamine.

In certain exemplary embodiments, $X^c$ is an omega-3 fatty acid. Non-limiting examples of omega-3 fatty acids include, but are not limited to, hexadecatrienoic acid (HTA), alpha-linolenic acid (ALA), searidonic acid (SDA), eicosatrienoic acid (ETE), eicosatetraenoic acid (ETA), eicosapentaenoic acid (EPA, timnodonic acid), heneicosapentaenoic acid (HPA), docosapentaenoic acid (DPA, clupanodonic acid), docosahexaenoic acid (DHA, cervonic acid), tetracosapentaenoic acid, and tetracosahexaenoic acid (nisinic acid).

In another embodiment, $X^c$ is an omega-6 fatty acid. Non-limiting examples of omega-6 fatty acids include, but are not limited to, linoleic acid, gamma-linolenic acid (GLA), eicosadienoic acid, dihomo-gamma-linolenic acid (DGLA), arachidonic acid (AA), docosadienoic acid, adrenic acid, docosapentaenoic acid (Osbond acid), tetracosatetraenoic acid, and tetracosapentaenoic acid.

In another embodiment, $X^c$ is an omega-9 fatty acid. Non-limiting examples of omega-9 fatty acids include, but are not limited to, oleic acid, eicosenoic acid, mead acid, erucic acid, and nervonic acid.

In another embodiment, $X^c$ is a conjugated linolenic acid. Non-limiting examples of conjugated linolenic acids include, but are not limited to, α-calendic acid, β-calendic acid, Jacaric acid, α-eleostearic acid, β-eleostearic acid, catalpic acid, and punicic acid.

In another embodiment, $X^c$ is a saturated fatty acid. Non-limiting examples of saturated fatty acids include, but are not limited to, caprylic acid, capric acid, docosanoic acid, lauric acid, myristic acid, palmitic acid, stearic acid, arachidic acid, behenic acid, lignoceric acid, and cerotic acid.

In another embodiment, $X^c$ is an acid selected from the group consisting of rumelenic acid, α-parinaric acid, β-parinaric acid, bosseopentaenoic acid, pinolenic acid and podocarpic acid.

In another embodiment, $X^c$ is selected from the group consisting of docosanoic acid (DCA), docosahexaenoic acid (DHA) and eicosapentaenoic acid (EPA). In a particular embodiment, $X^c$ is docosanoic acid (DCA). In another particular embodiment, $X^c$ is DHA. In another particular embodiment, $X^c$ is EPA.

In another embodiment, $X^c$ is a secosteroid. In a particular embodiment, $X^c$ is calciferol. In another embodiment, $X^c$ is a steroid other than cholesterol.

In another embodiment, $X^c$ is selected from the group consisting of an alkyl chain, a vitamin, a peptide, and a bioactive conjugate (including but not limited to: glycosphingolipids, polyunsaturated fatty acids, secosteroids, steroid hormones and sterol lipids).

In another embodiment of the oligonucleotide, $X^c$ is characterized by a cLogP value in a range selected from: −10 to −9, −9 to −8, −8 to −7, −7 to −6, −6 to −5, −5 to −4, −4 to −3, −3 to −2, −2 to −1, −1 to 0, 0 to 1, 1 to 2, 2 to 3, 3 to 4, 4 to 5, 5 to 6, 6 to 7, 7 to 8, 8 to 9, and 9 to 10.

As used herein, the term "O" refers to an oligonucleotide of at least 16 contiguous nucleotides, said oligonucleotide having a 5' end, a 3' end and complementarity to a target. In one embodiment, the oligonucleotide has sufficient complementarity to the target to hybridize. In certain embodiments, the complementarity is >95%, >90%, >85%, >80%, >75%, >70%, >65%, >60%, >55% or >50%. In one embodiment, the oligonucleotide has perfect complementarity to the target. In another embodiment, the oligonucleotide has one, two, three, four or more mismatches with the target.

In one embodiment, O comprises one or more chemically-modified nucleotides. In a particular embodiment, the oligonucleotide comprises alternating 2'-methoxy-nucleotides and 2'-fluoro-nucleotides. In another particular embodiment, the nucleotides at positions 1 and 2 from the 3' end of the oligonucleotide are connected to adjacent nucleotides via phosphorothioate linkages. In yet another particular embodiment, the nucleotides at positions 1 and 2 from the 3' end of the oligonucleotide and the nucleotides at positions 1 and 2 from the 5' end of the oligonucleotide are connected to adjacent nucleotides via phosphorothioate linkages. In yet another particular embodiment, the oligonucleotide comprises a 2'-fluoro modification at the nucleotide at each of positions 2 and 14 from the 5' end, and a 2'-methoxy modification at each other nucleotide position.

In one embodiment, O has complete homology with the target. In a particular embodiment, the target is mammalian or viral mRNA. In another particular embodiment, the target is an intronic region of said mRNA.

Figure 2:
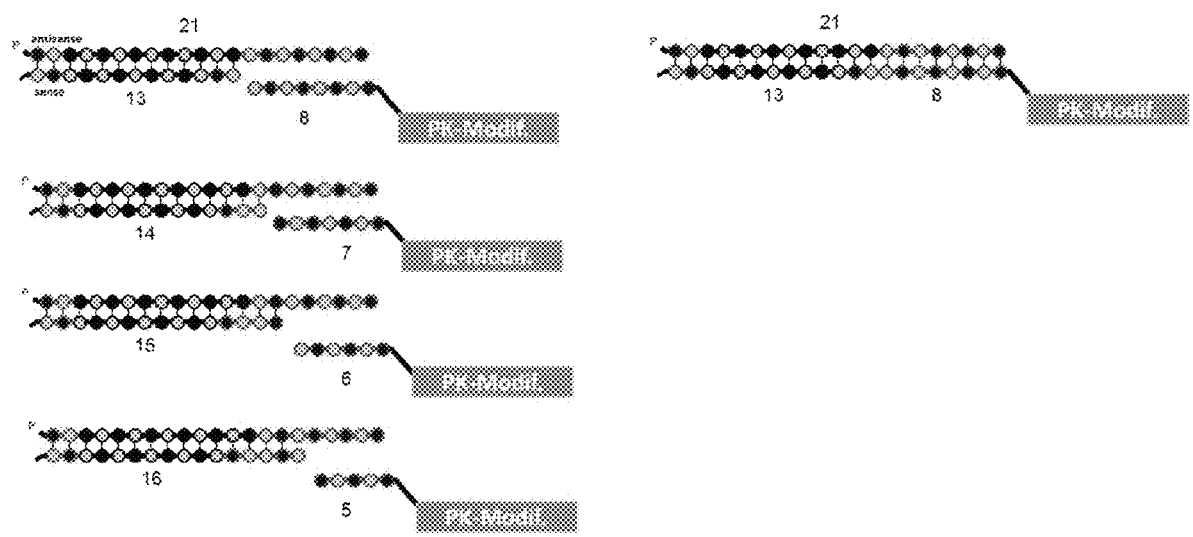
FIG. 2 schematically depicts exemplary configurations of asymmetric siRNAs and complementary oligonucleotide-containing anchors. The antisense strand comprises an overhang that can pair with an oligonucleotide anchor. In a non-limiting example, shown here is a 21-mer antisense strand that can hybridize to: a 13-mer sense strand and an 8-mer oligonucleotide anchor; a 14-mer sense strand and a 7-mer anchor; a 15-mer sense strand and a 6-mer anchor; or a 16-mer sense strand and a 5-mer anchor. In certain embodiments, the hybridized oligomers can contain one, two, three or more mismatches. See (FIG. 24.)
Figure 24:
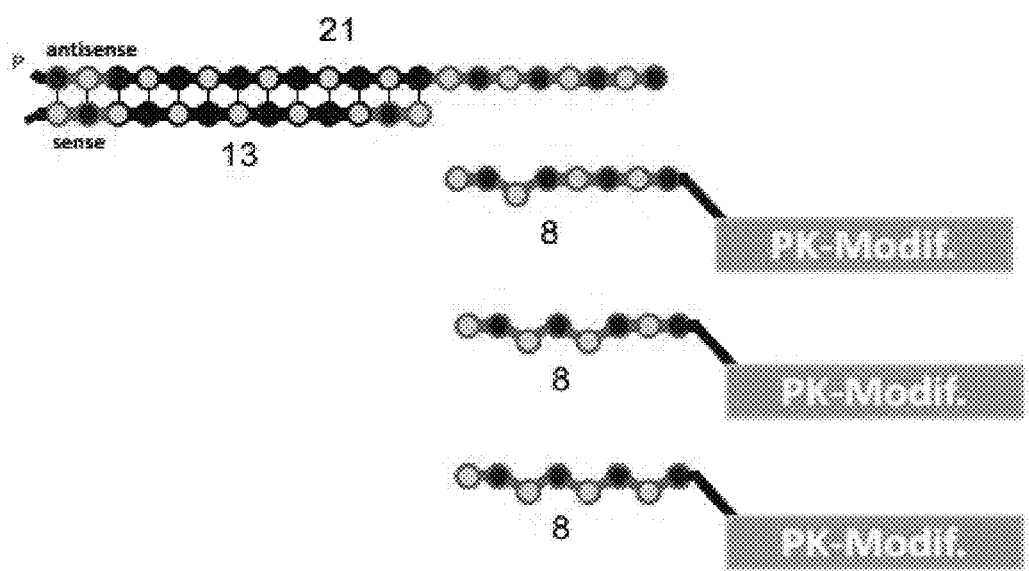
FIG. 24 schematically depicts exemplary configurations of asymmetric siRNAs and complementary oligonucleotide-containing anchors having mismatches for Tm optimization.

In one embodiment, O comprises an asymmetric duplex. The length of the sense strand and antisense strand of the asymmetric duplex can vary. In certain exemplary embodiments, the asymmetric duplex contains at least 16 contiguous nucleotides in the antisense strand and at least 12 contiguous nucleotides in the sense strand. In some embodiments, the asymmetric duplex contains a 21-mer oligonucleotide antisense strand and a 13-mer, 14-mer, 15-mer, or a 16-mer oligonucleotide sense strand. In some embodiments, the asymmetric duplex contains a 22-mer oligonucleotide antisense strand and a 13-mer, 14-mer, 15-mer, or a 16-mer oligonucleotide sense strand. In some embodiments, the asymmetric duplex contains a 23-mer oligonucleotide antisense strand and a 13-mer, 14-mer, 15-mer, or a 16-mer oligonucleotide sense strand. The length of the oligonucleotide anchor can vary with respect to the length of the oligonucleotide sense strand. In some embodiments, the sense strand is a 13-mer, 14-mer, 15-mer, or a 16-mer oligonucleotide and the oligonucleotide anchor is an 8-mer, 7-mer, 6-mer, or a 5-mer oligonucleotide (as shown in FIG. 2). In certain embodiments, the hybridized oligomers can contain one, two, three or more mismatches (as shown in FIG. 24).

In some embodiments, the asymmetric duplex contains a 23-mer oligonucleotide antisense strand and a 13-mer, 14-mer, 15-mer, or a 16-mer oligonucleotide sense strand. The length of the oligonucleotide anchor can vary with respect to the length of the oligonucleotide sense strand. In some embodiments, the sense strand is a 13-mer, 14-mer, 15-mer, or a 16-mer oligonucleotide and the oligonucleotide anchor is a 10-mer, 9-mer, 8-mer, 7-mer, 6-mer, or a 5-mer oligonucleotide.

In certain embodiments, O is a therapeutic RNA, e.g., an ASO, a ssRNA or the like, and the oligonucleotide anchor is a 15-mer, 14-mer, 13-mer, 12-mer, 11-mer, 10-mer, 10-mer, 9-mer, 8-mer, 7-mer, 6-mer, or a 5-mer oligonucleotide.

As used herein in the context of oligonucleotide sequences, "A" represents a nucleoside comprising the base adenine (e.g., adenosine or a chemically-modified derivative thereof), "G" represents a nucleoside comprising the base guanine (e.g., guanosine or a chemically-modified derivative thereof), "U" represents a nucleoside comprising the base uracil (e.g., uridine or a chemically-modified derivative thereof), and "C" represents a nucleoside comprising the base cytosine (e.g., cytidine or a chemically-modified derivative thereof).

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example, the 2' OH-group may be replaced by a group selected from H, OR, R, F, Cl, Br, I, SH, SR, $NH_2$, NHR, $NR_2$, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

The term "complementary" refers to the relationship between nucleotides exhibiting Watson-Crick base pairing, or to oligonucleotides that hybridize via Watson-Crick base pairing to form a double-stranded nucleic acid. The term "complementarity" refers to the state of an oligonucleotide (e.g., a sense strand or an antisense strand) that is partially or completely complementary to another oligonucleotide. Oligonucleotides described herein as having complementarity to a second oligonucleotide may be 100%, >95%, >90%, >85%, >80%, >75%, >70%, >65%, >60%, >55% or >50% complementary to the second oligonucleotide.

As used herein in the context of oligonucleotide sequences, "A" represents a nucleoside comprising the base adenine (e.g., adenosine or a chemically-modified derivative thereof), "G" represents a nucleoside comprising the base guanine (e.g., guanosine or a chemically-modified derivative thereof), "U" represents a nucleoside comprising the base uracil (e.g., uridine or a chemically-modified derivative thereof), and "C" represents a nucleoside comprising the base cytosine (e.g., cytidine or a chemically-modified derivative thereof).

As used herein, the term "3' end" refers to the end of a nucleic acid that contains an unmodified hydroxyl group at the 3' carbon of its ribose ring.

As used herein, the term "5' end" refers to the end of a nucleic acid that contains a phosphate group attached to the 5' carbon of its ribose ring.

As used herein, the term "nucleoside" refers to a molecule made up of a heterocyclic base and its sugar.

As used herein, the term "nucleotide" refers to a nucleoside having a phosphate group on its 3' or 5' sugar hydroxyl group.

An RNAi agent, e.g., an siRNA, having a strand which is "sequence sufficiently complementary to a target mRNA sequence to direct target-specific RNA interference (RNAi)" means that the strand has a sequence sufficient to trigger the destruction of the target mRNA by RNAi.

As used herein, the term "isolated RNA" (e.g., "isolated siRNA," or "isolated siRNA precursor") refers to an RNA molecule that is substantially free of other cellular material, or culture medium when produced by recombinant techniques, or substantially free of chemical precursors or other chemicals when chemically synthesized.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence, e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g., promoter or enhancer elements) of a target gene. In other embodiments, the target polynucleotide sequence is a target mRNA encoded by a target gene.

As used herein, the term "siRNA" refers to small interfering RNAs that induce the RNA interference (RNAi) pathway. siRNA molecules can vary in length (generally between 18-30 base pairs) and contain varying degrees of complementarity to their target mRNA. The term "siRNA" includes duplexes of two separate strands, as well as single strands that can form hairpin structures comprising a duplex region.

As used herein, the term "antisense strand" refers to the strand of an siRNA duplex that contains some degree of complementarity to a target gene or mRNA and contains complementarity to the sense strand of the siRNA duplex.

As used herein, the term "sense strand" refers to the strand of an siRNA duplex that contains complementarity to the antisense strand of the siRNA duplex.

As used herein, the term "overhang" or "tail" refers to 3, 4, 5, 6, 7, 8, 9, 10, 11, 12, 13, 14, 15, 16, 17, 18, 19, 20 or more sequential nucleotides at the 3' end of one or both of the sense strand and the antisense strand that are single-stranded, i.e., are not base paired to (i.e., do not form a duplex with) the other strand of the siRNA duplex.

As used herein, the term "antisense oligonucleotide" or "ASO" refers to a nucleic acid (e.g., an RNA), having sufficient sequence complementarity to a target an RNA (e.g., a SNP-containing mRNA or a SNP-containing pre-mRNA) in order to block a region of a target RNA in an effective manner, e.g., in a manner effective to inhibit translation of a target mRNA and/or splicing of a target pre-mRNA. An antisense oligonucleotide having a "sequence sufficiently complementary to a target RNA" means that the antisense agent has a sequence sufficient to mask a binding site for a protein that would otherwise modulate splicing and/or that the antisense agent has a sequence sufficient to mask a binding site for a ribosome and/or that the antisense agent has a sequence sufficient to alter the three-dimensional structure of the targeted RNA to prevent splicing and/or translation.

In certain exemplary embodiments, an siRNA of the invention is asymmetric. In certain exemplary embodiments, an siRNA of the invention is symmetric.

In certain exemplary embodiments, an siRNA of the invention comprises a duplex region of between about 8-20 nucleotides or nucleotide analogs in length, between about 10-18 nucleotides or nucleotide analogs in length, between about 12-16 nucleotides or nucleotide analogs in length, or between about 13-15 nucleotides or nucleotide analogs in length (e.g., a duplex region of about 8, 9, 10, 11, 12, 13, 14, 15, 16, 17, 18, 19 or 20 base pairs).

In certain exemplary embodiments, an siRNA of the invention comprises one or two overhangs. In certain embodiments, each overhang of the siRNA comprises at least about 3, about 4, about 5, about 6, about 7, about 8, about 9, or about 10 sequential nucleotides. In certain embodiments, each overhang of the siRNA of the invention is about 4, about 5, about 6 or about 7 nucleotides in length. In certain embodiments, the sense strand overhang is the same number of nucleotides in length as the antisense strand overhang. In other embodiments, the sense strand overhang has fewer nucleotides than the antisense strand overhang. In other embodiments, the antisense strand overhang has fewer nucleotides than the sense strand overhang.

In certain exemplary embodiments, an siRNA of the invention comprises a sense strand and/or an antisense strand each having a length of about 10, about 15, about 20, about 25 or about 30 nucleotides. In particular embodiments, an siRNA of the invention comprises a sense strand and/or an antisense strand each having a length of between about 15 and about 25 nucleotides. In particular embodiments, an siRNA of the invention comprises a sense strand and an antisense strand that are each about 20 nucleotides in length. In certain embodiments, the sense strand and the antisense strand of an siRNA are the same length. In other embodiments, the sense strand and the antisense strand of an siRNA are different lengths.

In certain exemplary embodiments, an siRNA of the invention has a total length (from the 3' end of the antisense strand to the 3' end of the sense strand) of about 20, about 25, about 30, about 35, about 40, about 45, about 50 or about 75 nucleotides. In certain exemplary embodiments, an siRNA of the invention has a total length of between about 15 and about 35 nucleotide. In other exemplary embodiments, the siRNA of the invention has a total length of between about 20 and about 30 nucleotides. In other exemplary embodiments, the siRNA of the invention has a total length of between about 22 and about 28 nucleotides. In particular embodiments, an siRNA of the invention has a total length of about 20, about 21, about 22, about 23, about 24, about 25, about 26, about 27, about 28, about 29 or about 30 nucleotides.

Figure 25:
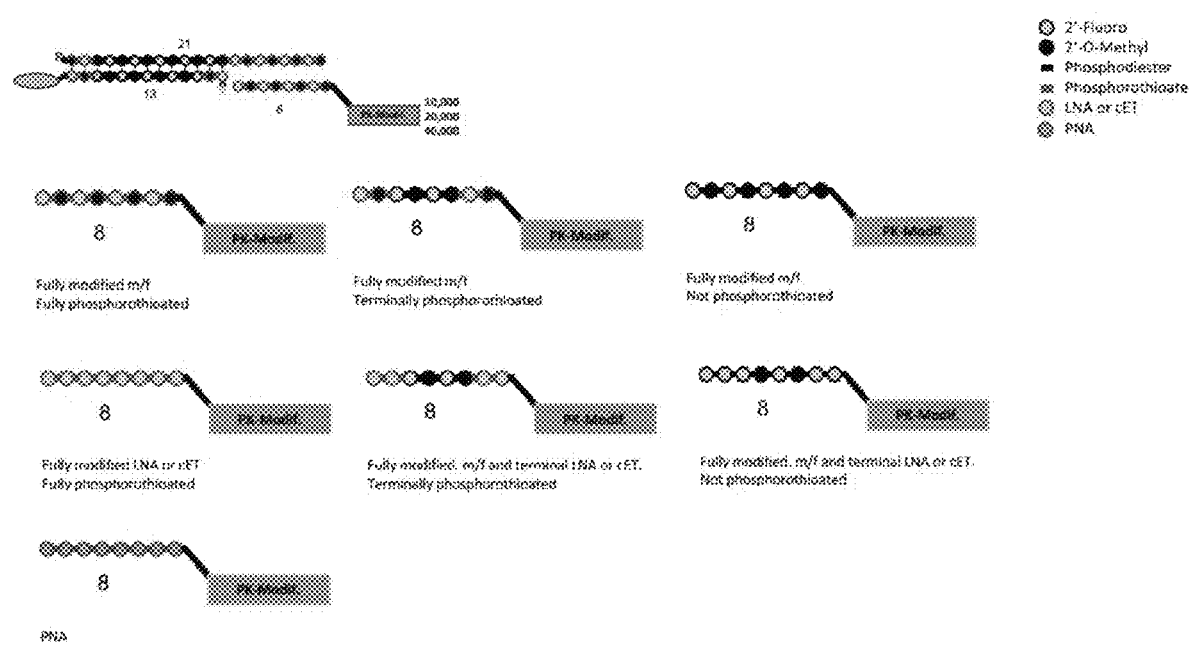
FIG. 25 schematically depicts exemplary configurations of asymmetric siRNAs comprising a variety of chemical modifications.
Figure 26:
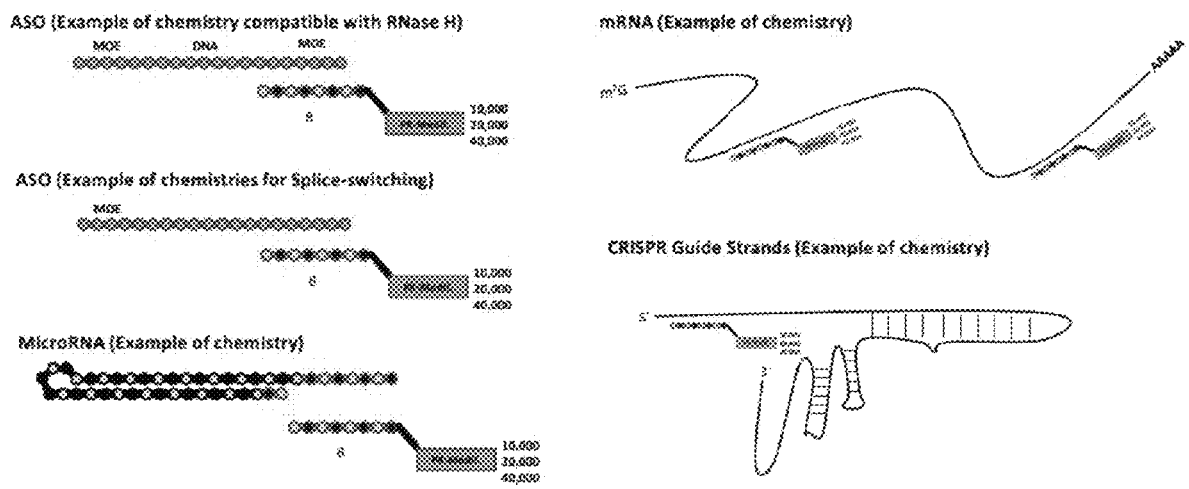
Figure 27:
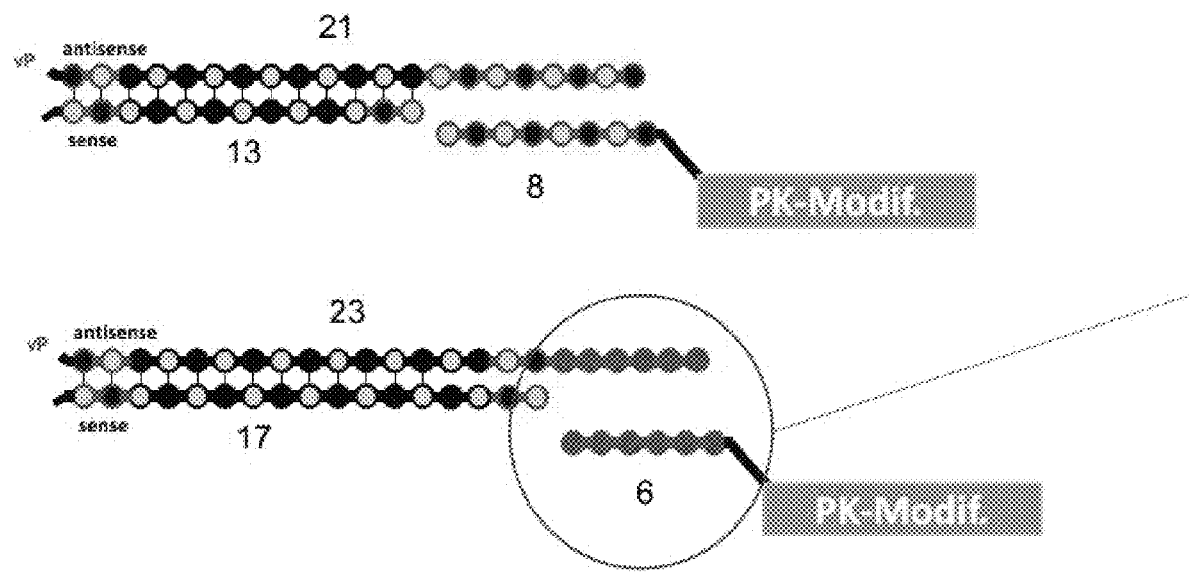
FIG. 27 schematically depicts exemplary configurations of asymmetric siRNAs and complementary oligonucleotide-containing anchors. The circle represents a fixed sequence of a plurality of dynamic oligonucleotide anchors that can be used in siRNA constructs that target a variety of different mRNAs. In certain embodiments, the antisense strand is increased in length up to 23 nucleotides total. In certain embodiments, the nucleotides from position 18 through 23 does not hybridize with an mRNA target. In certain embodiments, a fixed/conserved oligonucleotide anchor region, that can be used with various siRNAs targeting different mRNA targets, is provided. In certain embodiments, the 3'-end of the antisense strand may, or may not, be fully complementary with the mRNA target. In certain embodiments, a 5-mer to 10-mer anchor is used.

As used herein, the terms "chemically modified nucleotide" or "nucleotide analog" or "altered nucleotide" or "modified nucleotide" refer to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310. Exemplary chemical modifications are depicted at FIG. 25.

Nucleotide analogs may also comprise modifications to the sugar portion of the nucleotides. For example, the 2' OH-group may be replaced by a group selected from H, OR, R, F, Cl, Br, I, SH, SR, $NH_2$, NHR, $NR_2$, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

As used herein, the term "metabolically stabilized" refers to RNA molecules that contain 2'-ribose modifications to replace native 2'-hydroxyl groups with 2'-O-methyl groups or 2'-fluoro groups. In particular embodiments, the duplex region of an siRNA comprises one or two 2'-fluoro modifications and/or at least about 86%, at least about 87%, at least about 88%, at least about 89%, at least about 90%, at least about 91%, at least about 92%, at least about 93% or at least about 94% 2'-methoxy modifications. In certain exemplary embodiments, the antisense strand comprises two 2'-fluoro modifications and at least about 90%, at least about 91%, at least about 92%, at least about 93% or at least about 94% 2'-methoxy modifications. In certain exemplary embodiments, the sense strand comprises at least about 91%, at least about 92%, at least about 93%, at least about 94%, at least about 95%, at least about 96%, at least about 97%, at least about 98%, at least about 99% or about 100% 2'-methoxy modifications. In certain exemplary embodiments, the sense strand comprises no 2'-fluoro modifications and at least about 91%, at least about 92%, at least about 93%, at least about 94%, at least about 95%, at least about 96%, at least about 97%, at least about 98%, at least about 99% or about 100% 2'-methoxy modifications. In certain exemplary embodiments, a single-stranded RNA is provided that comprises two 2'-fluoro modifications and at least about 90%, at least about 91%, at least about 92%, at least about 93% or at least about 94% 2'-methoxy modifications. In certain exemplary embodiments, a single-stranded RNA is provided that comprises no 2'-fluoro modifications and at least about 91%, at least about 92%, at least about 93%, at least about 94%, at least about 95%, at least about 96%, at least about 97%, at least about 98%, at least about 99% or about 100% 2'-methoxy modifications.

As used herein, the term "phosphorothioate" refers to the phosphate group of a nucleotide that is modified by substituting one or more of the oxygens of the phosphate group with sulfur. A phosphorothioate further comprises a cationic counter-ion (e.g., sodium, potassium, calcium, magnesium or the like). The term "phosphorothioated nucleotide" refers to a nucleotide having one or two phosphorothioate linkages to another nucleotide. In certain embodiments, the single-stranded tails of the siRNAs of the invention comprise or consist of phosphorothioated nucleotides.

In some embodiments, the compounds, oligonucleotides and nucleic acids described herein may be modified to comprise one or more internucleotide linkages provided in FIG. 3. In particular embodiments, the compounds, oligonucleotides and nucleic acids described herein comprise one or more internucleotide linkages selected from phosphodiester and phosphorothioate.

It is understood that certain internucleotide linkages provided herein, including, e.g., phosphodiester and phosphorothioate, comprise a formal charge of −1 at physiological pH, and that said formal charge will be balanced by a cationic moiety, e.g., an alkali metal such as sodium or potassium, an alkali earth metal such as calcium or magnesium, or an ammonium or guanidinium ion.

As used herein, the term "lipid formulation" may refer to liposomal formulations, e.g., wherein liposomes are used to form nanoparticles with nucleic acids in order to promote internalization of the nucleic acids into a cell. Without being bound by theory, liposomes suitable for use are those that readily merge with the phospholipid bilayer of the cell membrane, thereby allowing the nucleic acids to penetrate the cell. In one embodiment, the compound comprises a nanoparticle, an intercalating agent, a polycation, or a mixture thereof.

In certain embodiments, the compound of the disclosure is represented by formula (I):

$$X^c\text{—}L\text{—}O\text{—}Z,\qquad(I)$$

wherein the line "—" represents a means of interaction between "$X^c$", "L", "O", and "Z". In certain embodiments, the interaction is through base pair complementarity, such as the base pair complementarity between the oligonucleotide O and the anchor oligonucleotide of the PK-modifying anchor Z. In certain embodiments, the interaction is through a covalent bond, such as the bond between $X^c$ and L, or between L and O.

Pharmaceutical Compositions and Methods of Administration

In one aspect, provided herein is a pharmaceutical composition comprising a therapeutically effective amount of one or more compound, oligonucleotide, or nucleic acid as described herein, and a pharmaceutically acceptable carrier. In one embodiment, the pharmaceutical composition comprises one or more double-stranded, chemically-modified nucleic acid comprising a pharmacokinetic-modifying anchor as described herein, and a pharmaceutically acceptable carrier. In a particular embodiment, the pharmaceutical composition comprises one double-stranded, chemically-modified nucleic acid comprising a pharmacokinetic-modifying anchor as described herein, and a pharmaceutically acceptable carrier. In another particular embodiment, the pharmaceutical composition comprises two double-stranded, chemically-modified nucleic acids comprising a pharmacokinetic-modifying anchor as described herein, and a pharmaceutically acceptable carrier.

The invention pertains to uses of the above-described agents for therapeutic treatments as described Infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), intravitreal, intra-articular, intranasal, intravaginal, rectal, sublingual and transmucosal administration. In certain exemplary embodiments, a pharmaceutical composition of the invention is delivered to the cerebrospinal fluid (CSF) by a route of administration that includes, but is not limited to, intrastriatal (IS) administration, intracerebroventricular (ICV) administration and intrathecal (IT) administration (e.g., via a pump, an infusion or the like). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be suitable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the exemplary methods of preparation are vacuum drying and freeze-drying which yields a powder of the active ingredient plus any additional desired ingredient from a previously sterile-filtered solution thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are particularly suitable. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. In particular embodiments, the dosage of such compounds lies within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. A dose may also be formulated by ascertaining tissue concentrations of oligonucleotide vs. gene silencing effects in an animal model. Such information can be used to more accurately determine useful doses in humans. Levels in plasma may be measured, for example, by high performance liquid chromatography.

Methods of Treatment

"Treatment" or "treating," as used herein, is defined as the application or administration of a therapeutic agent (e.g., an RNAi agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, a method for preventing in a subject, a disease or disorder as described above, by administering to the subject a therapeutic agent (e.g., an RNAi agent or vector or transgene encoding same) is provided. Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Design of siRNA Molecules

In some embodiments, an siRNA molecule of the invention is a duplex consisting of a sense strand and complementary antisense strand, the antisense strand having sufficient complementary to a target mRNA to mediate RNAi. In particularly exemplary embodiments, the siRNA molecule has a length from about 10-50 or more nucleotides, i.e., each strand comprises 10-50 nucleotides (or nucleotide analogs). In particularly exemplary embodiments, the siRNA molecule has a length from about 16-30, e.g., about 16, about 17, about 18, about 19, about 20, about 21, about 22, about 23, about 24, about 25, about 26, about 27, about 28, about 29 or about 30 nucleotides in each strand, wherein one of the strands is sufficiently complementary to a target region. The strands can be aligned such that there are at least about 1, about 2 or about 3 bases at the end of the strands which do not align (i.e., for which no complementary bases occur in the opposing strand) such that an overhang of about 1, about 2 or about 3 residues occurs at one or both ends of the duplex when strands are annealed. The strands can be aligned such that there are about 5, about 6, about 7 or about 8 bases at the end of the strands which do not align and form an overhang. The siRNA molecule can have a length from about 10-50 or more nucleotides, i.e., each strand comprises about 10 to about 50 nucleotides (or nucleotide analogs). In particularly exemplary embodiments, the siRNA molecule has a length from about 16 to about 30, e.g., about 16, about 17, about 18, about 19, about 20, about 21, about 22, about 23, about 24, about 25, about 26, about 27, about 28, about 29 or about 30 nucleotides in each strand, wherein one of the strands is substantially complementary to a target sequence, and the other strand is identical or substantially identical to the first strand.

Generally, siRNAs can be designed by using any method known in the art, for instance, by using the following protocol:

1. The siRNA should be specific for a target sequence. The first strand should be complementary to the target sequence, and the other strand is substantially complementary to the first strand. In another embodiment, the target sequence is outside a coding region of the target gene. Exemplary target sequences are selected from the 5' untranslated region (5'-UTR) or an intronic region of a target gene. Cleavage of mRNA at these sites should eliminate translation of corresponding protein. Target sequences from other regions of a target gene are also suitable for targeting. A sense strand is designed based on the target sequence. Further, siRNAs with lower G/C content (35-55%) may be more active than those with G/C content higher than 55%. Thus, in one embodiment, the invention includes nucleic acid molecules having 35-55% G/C content.

2. The sense strand of the siRNA is designed based on the sequence of the selected target site. In particularly exemplary embodiments, the sense strand includes about 10 to about 20 nucleotides, e.g., about 10, about 11, about 12, about 13, about 14, about 15, about 16, about 17, about 18, about 19 or about 20 nucleotides. In particularly exemplary embodiments, the sense strand includes about 13, about 14, about 15 or about 16 nucleotides. The skilled artisan will appreciate, however, that siRNAs having a length of less than about 10 nucleotides or greater than about 20 nucleotides can also function to mediate RNAi. Accordingly, siRNAs of such length are also within the scope of the instant invention provided that they retain the ability to mediate RNAi. Longer RNA silencing agents have been demonstrated to elicit an interferon or Protein Kinase R (PKR) response in certain mammalian cells which may be undesirable. In particular embodiments, the RNA silencing agents of the invention do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the invention have sufficient complementarity with the target sequence such that the siRNA can mediate RNAi. In general, siRNA containing nucleotide sequences are provided that are sufficiently identical to a target sequence portion of the target gene to effect RISC-mediated cleavage of the target gene. Accordingly, in particular exemplary embodiments, the sense strand of the siRNA is designed to have a sequence sufficiently identical to a portion of the target. For example, the sense strand may have 100% identity to the target site. However, 100% identity is not required. Greater than about 80% identity, e.g., about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or even 100% identity, between the sense strand and the target RNA sequence is achieved. The invention has the advantage of being able to tolerate certain sequence variations to enhance efficiency and specificity of RNAi. In one embodiment, the sense strand has about 4, about 3, about 2, about 1 or about 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/ total number of positions ×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely a different length than the sense strand and includes complementary nucleotides. In one embodiment, the strands of the siRNA can be paired in such a way as to have a 3' overhang of about 5, about 6, about 7, about 8, about 9 or about 10 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. The overhanging nucleotides may be either RNA or DNA. As noted above, it is desirable to choose a target region wherein the mutant:wild type mismatch is a purine: purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional exemplary hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+ 0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs, the siRNA may be incubated with target cDNA in a Drosophila-based in vitro mRNA expression system. Radiolabeled with $^{32}P$, newly synthesized target mRNAs are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

Sites of siRNA-mRNA complementation are selected which result in optimal mRNA specificity and maximal mRNA cleavage.

siRNA-Like Molecules siRNA-like molecules of the invention have a sequence (i.e., have a strand having a sequence) that is "sufficiently complementary" to a target sequence of a target mRNA to direct gene silencing either by RNAi or translational repression. siRNA-like molecules are designed in the same way as siRNA molecules, but the degree of sequence identity between the sense strand and target RNA approximates that observed between a miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further embodiment, the "bulge" is centered at nucleotide positions 12 and 13 from the 5' end of the miRNA molecule (e.g., the antisense strand).

Modified RNA Silencing Agents

In certain aspects of the invention, an RNA silencing agent (or any portion thereof) of the invention as described supra may be modified such that the activity of the agent is further improved. For example, the RNA silencing agents described supra may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In particular embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide can be used because it has relatively minor effect on the stability of the RNA duplex or the duplex formed by the guide strand of the RNA silencing agent and the target mRNA. Exemplary universal nucleotides include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particular embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destabilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In particular embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. In particular embodiments, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the invention may be enhanced such that there are fewer G:C base pairs between the 5' end of the antisense strand and the 3' end of the sense strand portion than between the 3' end of antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. In particular embodiments, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). In particular embodiments, the base pair is selected from the group consisting of an I:A, I:U and I:C. In yet another embodiment, the asymmetry of an RNA silencing agent of the invention may be enhanced such that there is at least one base pair comprising a modified nucleotide.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a particular aspect, the invention features RNA silencing agents that can include first, second and third strands, wherein any of the first, second and third strands can be modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a particular embodiment, the RNA silencing agents (e.g., any combination of a first oligonucleotide, a second oligonucleotide and a third oligonucleotide) may optionally contain at least one modified nucleotide analogue. The nucleotide analogues may be located at positions where the target-specific silencing activity, e.g., the RNAi mediating activity or translational repression activity is not substantially affected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone in any of a first oligonucleotide, a second oligonucleotide and/or a third oligonucleotide). For example, the phosphodiester linkages of natural RNA may be modified to include at least one of a nitrogen or sulfur heteroatom. In exemplary backbone-modified ribonucleotides, the phosphodiester group connecting to adjacent ribonucleotides is replaced by a modified group, e.g., of phosphorothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particular exemplary modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moieties of the instant invention. Additional modified residues include, deoxy-abasic, inosine, N3-methyl-uridine, N6,N6-dimethyl-adenosine, pseudouridine, purine ribonucleoside and ribavirin. In a particular exemplary embodiment, the 2' moiety is a methyl group such that the linking moiety is a 2'-O-methyl oligonucleotide.

In an exemplary embodiment, the RNA silencing agent of the invention (e.g., any combination of a first oligonucleotide, a second oligonucleotide and a third oligonucleotide) comprises locked nucleic acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-O,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the invention (e.g., any combination of a first oligonucleotide, a second oligonucleotide and a third oligonucleotide) comprises peptide nucleic acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

In another exemplary embodiment, the RNA silencing agent of the invention (e.g., any combination of a first oligonucleotide, a second oligonucleotide and a third oligonucleotide) comprises phosphorodiamidate morpholino oligomers (PMOs). PMOs comprise modified nucleotides that have standard nucleic acid bases that are bound to methylenemorpholine rings linked through phosphorodiamidate groups instead of phosphates (Summerton et al. (1997) Antisense & Nucleic Acid Drug Development. 7 (3): 187-95).

Also provided are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at the 3' terminus) to another moiety (e.g., to a non-nucleic acid moiety such as a peptide), an organic compound (e.g., a dye), or the like. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an O with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents (e.g., any combination of a first strand oligonucleotide, a second oligonucleotide and a third oligonucleotide) may be modified with chemical moieties, for example, to enhance cellular uptake by target cells (e.g., neuronal cells). Thus, the invention includes RNA silencing agents which are conjugated or unconjugated (e.g., at the 3' end of the sense strand) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are typically located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a polyarginine peptide, peptoid or peptidomimetic, which can enhance the cellular uptake of an oligonucleotide agent.

Exemplary ligands are coupled, e.g., covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, transferrin mimetic peptides, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases, lipophilic molecules, e.g., cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. In particular embodiments, such a lipid or lipid-based molecule binds a serum protein, e.g., human serum albumin (HSA). An HSA-binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid-based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a particular embodiment, the lipid-based ligand binds HSA. A lipid-based ligand can bind HSA with a sufficient affinity such that the conjugate will be distributed to a non-kidney tissue. However, in particular embodiments, the affinity is not so strong that the HSA-ligand binding cannot be reversed. In another particular embodiment, the lipid-based ligand binds HSA weakly or not at all, such that the conjugate will be distributed to the kidney. Other moieties that target to kidney cells can also be used in place of or in addition to the lipid-based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low-density lipoprotein (LDL).

In another aspect, the ligand is a cell-permeation agent, e.g., a helical cell-permeation agent. The agent can be amphipathic. An exemplary agent is a peptide such as tat or antennopedia. If the agent is a peptide, it can be modified, including a peptidyl mimetic, invertomers, non-peptide or pseudo-peptide linkages, and use of D-amino acids. In particular embodiments, the helical agent is an alpha-helical agent, which optionally has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery.

EXAMPLE

Example 1. Oligonucleotides Comprising Dynamic Pharmacokinetic (PK)-Modifying Anchors for Cerebrospinal Fluid and Systemic Delivery 1.1 PK-Modifying Anchors A major challenge in the therapeutic oligonucleotide field is that non-serum binding oligonucleotides are cleared from the cerebrospinal fluid (CSF) and blood/plasma within minutes of injection. This quick clearance is a primary limiting factor for oligonucleotide delivery to tissue beyond the liver and the kidneys. In the central nervous system, the primary mechanism behind oligonucleotide distribution though the brain is bulk CSF flow. Oligonucleotides are cleared from the central nervous system quickly, which limits distribution in organisms with large and complex brains (including humans). The PK-modifying molecular anchors disclosed herein are patterned to enable efficient modulation of absorption, distribution and clearance kinetics of therapeutic oligonucleotides to enhance their tissue distribution. Efficient modulation of the absorption, distribution and clearance kinetics can be achieved in blood/plasma, cerebrospinal fluid (CSF) and other relevant bodily/biological fluids and tissues. The PK-modifying molecular anchors disclosed herein modulate CSF clearance kinetics and enhance the efficacy of therapeutic oligonucleotides in all brain regions, independent of the site of administration.

The PK-modifying anchors described dynamically modulate the size of therapeutic oligonucleotides, leading to the modulation of clearance kinetics versus tissue uptake and distribution. The dynamic nature of this concept is achieved through optimization of anchor size and chemical composition. PK-modifying anchors are described here that have an optimal size for modulating CSF clearance rates and modulation of systemic clearance. Additionally, a panel of non-immunogenic polymers (including poloxamer 188) and block-polymers are described here that serve as pharmacokinetic-modifying moieties.

Figures 8A, 8B:
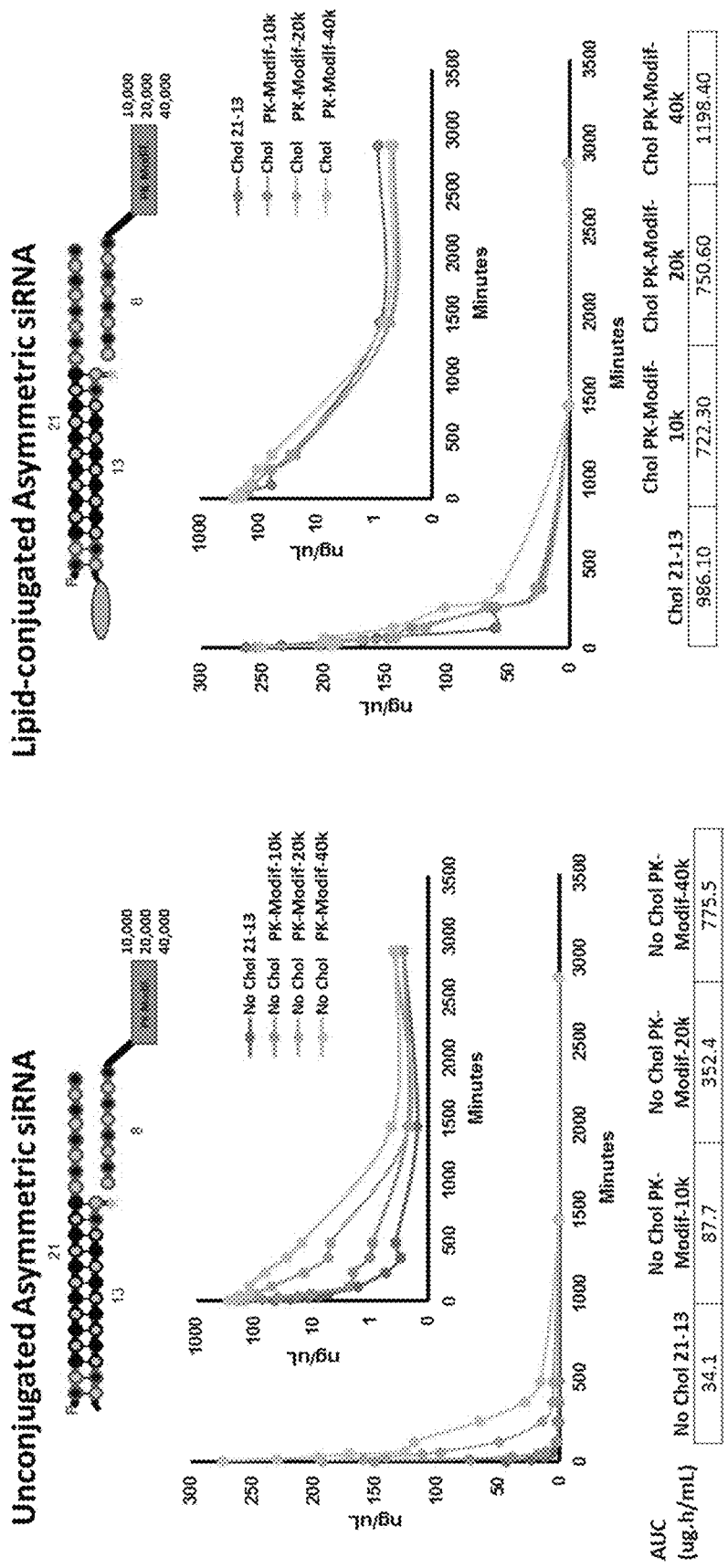
FIG. 8A-FIG. 8B depict blood/plasma circulating times and areas under the curve of unconjugated (FIG. 8A) and cholesterol-conjugated (FIG. 8B) hsiRNAs after intravenous injections. 20 mg/kg tail vein injections were performed in female FVB/N mice (at approximately 9-12 weeks old).
Figure 9A:
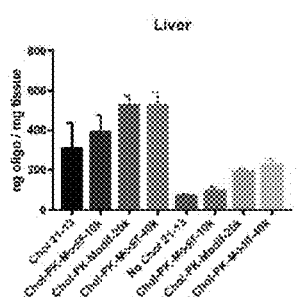
FIG. 9A-FIG. 9G depict the effects of PK-modifying anchors on in vivo biodistribution. Polyethylene glycol (PEG) was used as the PK-modifying polymer. The siRNA asymmetric duplex contained a 21-mer oligonucleotide antisense strand and a 13-mer oligonucleotide sense strand. A fully phosphorothioated 8-mer oligonucleotide anchor was used. 20 mg/kg tail vein injections performed in female FVB/N mice (at approximately 9-12 weeks old). The antisense strand was quantified using a peptide nucleic acid hybridization assay after 48 hours. Biodistribution of hsiRNAs is shown for liver (FIG. 9A), spleen (FIG. 9B), kidney (FIG. 9C), adrenals (FIG. 9D), heart (FIG. 9E), pancreas (FIG. 9F) and lung (FIG. 9G).
Figure 9B:
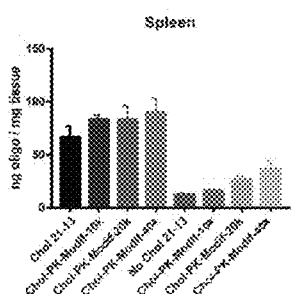
Figure 9C:
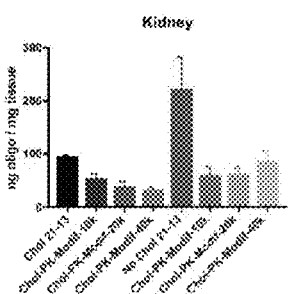
Figure 9D:
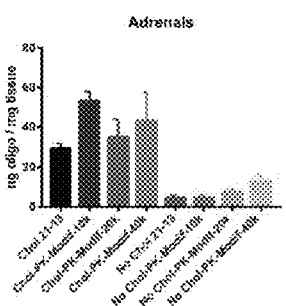
Figure 9E:
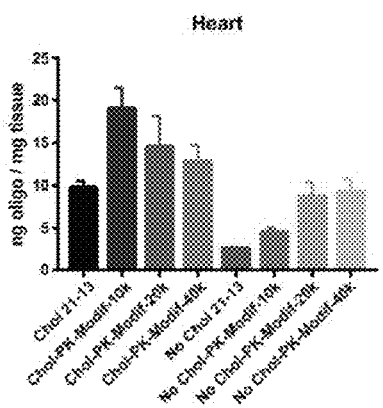
Figure 9F:
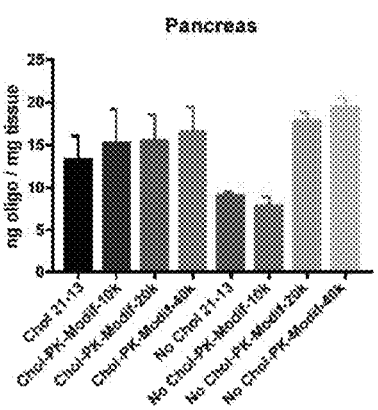
Figure 9G:
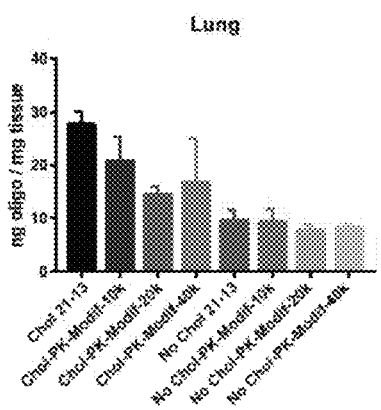

1.2 PK-Modifying Anchors Dynamically Improved Blood/Plasma Circulating Times of hsiRNA Compounds As shown at FIG. 8, the effect of PK-modifying anchors on the blood/plasma circulating times of hydrophobically modified siRNA (hsiRNA) was tested. It was determined that PK-modifying molecular anchors enhanced circulating times and areas under the curve of unconjugated (FIG. 8A) and cholesterol-conjugated (FIG. 8B) siRNAs after intravenous injections. Polyethylene glycol (PEG) was used as a model PK-modifying polymer. An 8-mer oligonucleotide with a phosphorothioated backbone was used as a model oligonucleotide anchor. The PK-modifying anchor hybridized to an asymmetric hsiRNA duplex containing a 21-mer oligonucleotide antisense strand and a 13-mer oligonucleotide sense strand. Increasing the length of the PEG moiety markedly improved circulating times of the hsiRNA compound.

20 mg/kg tail vein injections were performed in female FVB/N mice (approximately 9-12 weeks old). The antisense strand was quantified by peptide nucleic acid (PNA) hybridization assay as previously described in Godinho et al. 2017 (Nucleic Acids Therapeutics). Briefly, this assay used a cy3-labelled PNA probe that hybridizes to the antisense strand, with subsequent quantification by HPLC. The area under the curve (AUC) was calculated using the model-independent trapezoidal method with GastroPlus, Simulations Plus.

1.3 PK-Modifying Anchors Modulated Systemic In Vivo Biodistribution of hsiRNA Compounds As shown at FIG. 9, the effect of PK-modifying anchors on biodistribution of hsiRNAs was tested. Localization of hsiRNAs was tested with respect to liver (FIG. 9A), spleen (FIG. 9B), kidney (FIG. 9C), adrenals (FIG. 9D), heart (FIG. 9E), pancreas (FIG. 9F), and lung (FIG. 9G). PEG was used as a model PK-modifying polymer. An 8-mer oligonucleotide with a phosphorothioated backbone was used as a model oligonucleotide anchor. The PK-modifying anchor was hybridized to an asymmetric hsiRNA duplex containing a 21-mer oligonucleotide antisense strand and a 13-mer oligonucleotide sense strand.

Many embodiments of the pharmacokinetic-modifying anchor and oligonucleotide anchor are possible. The length and chemistry of the anchor can be adjusted according to the delivery aim or goal. As shown at FIG. 9, pharmacokinetic-modifying anchors significantly affected the biodistribution of unconjugated and cholesterol-conjugated hsiRNAs after intravenous injections. FIG. 9 shows a positive correlation between increasing the length of the PEG moiety and improved delivery of unconjugated oligonucleotides to most organs.

20 mg/kg tail vein injections were performed in female FVB/N mice (approximately 9-12 weeks old). The antisense strand was quantified by PNA Hybridization assay after 48 hours.

Figure 17:
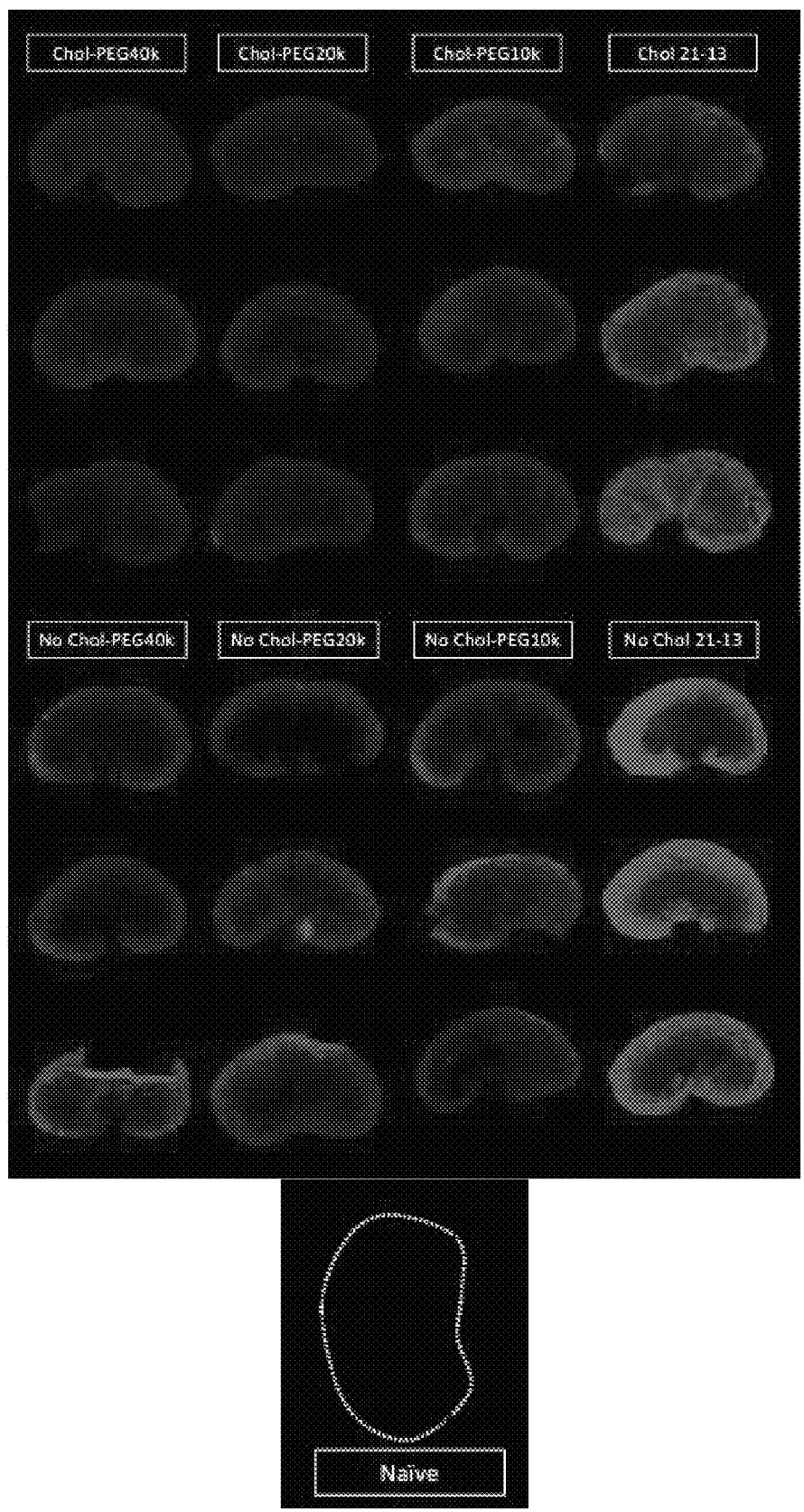
FIG. 17 depicts kidney distribution after IV administration.
Figure 18:
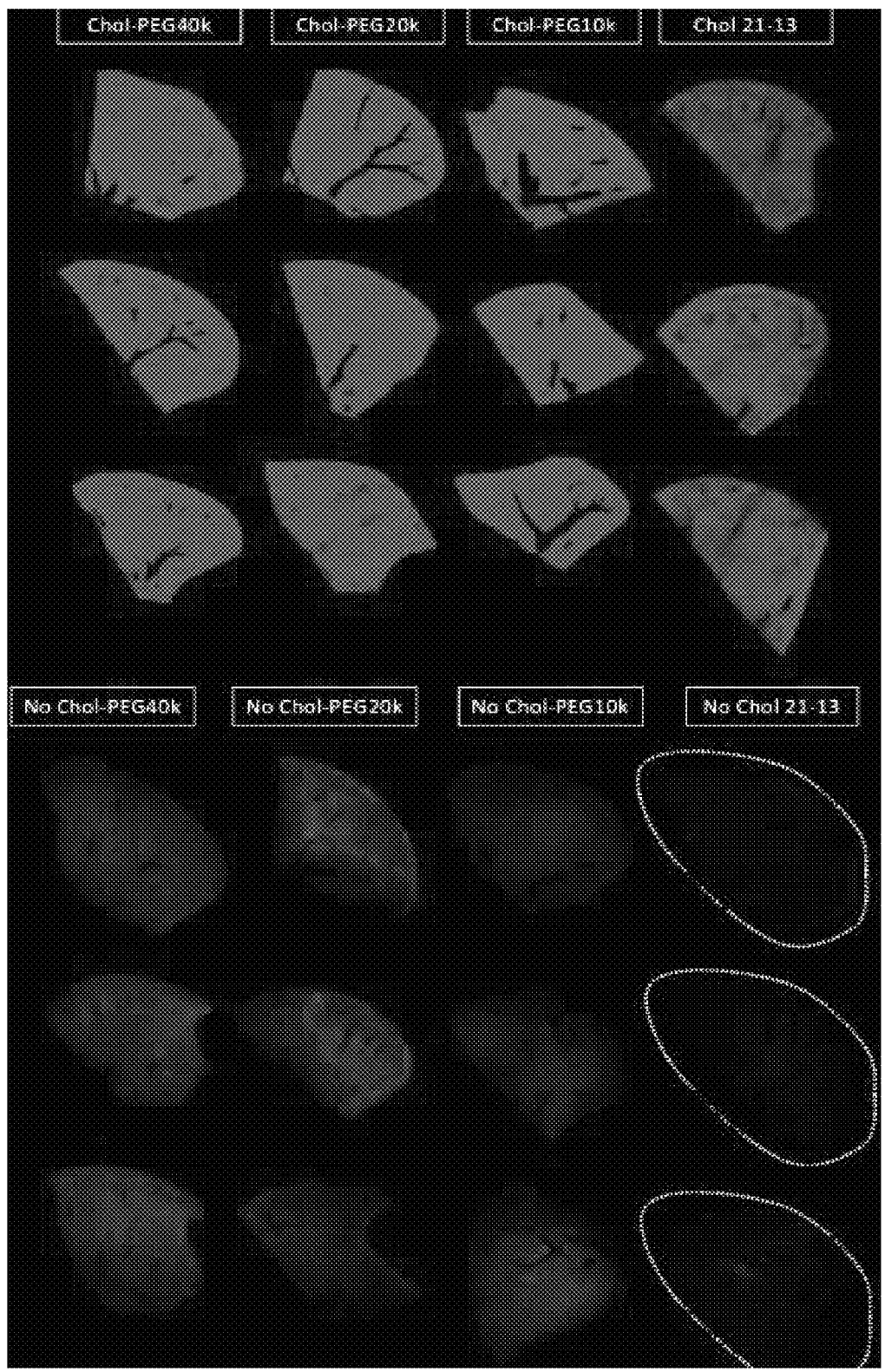
FIG. 18 depicts liver distribution after IV administration.
Figure 19:
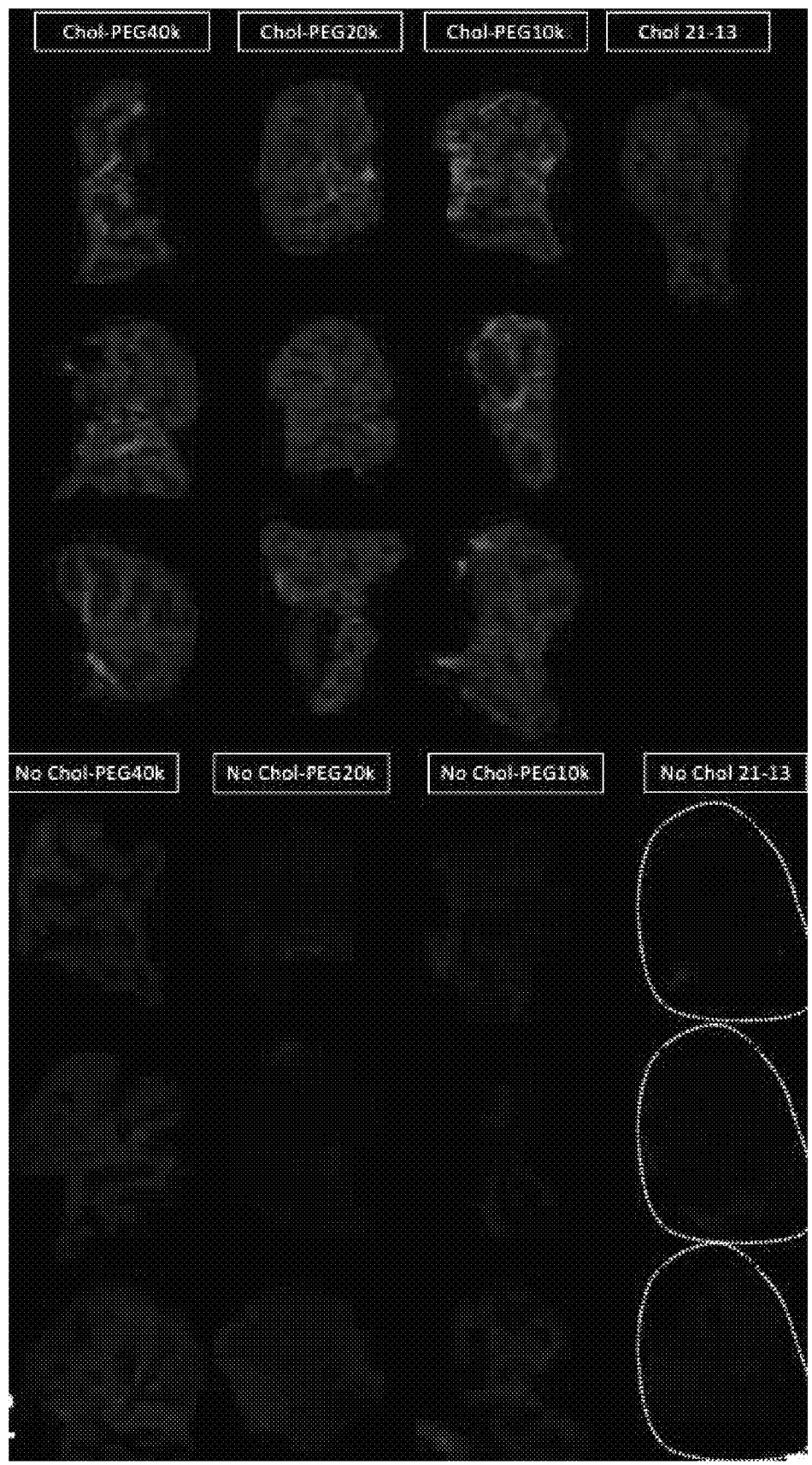
FIG. 19 depicts spleen distribution after IV administration.

1.4 PK-Modifying Anchors Enabled Efficient and Potent Gene Silencing after Systemic Administration The ability of PK-modifying anchors to deliver hsiRNA compounds to the liver (FIG. 10A, FIG. 18), the kidney (FIG. 10B, FIG. 17), and the spleen (FIG. 10C, FIG. 19) after intravenous administration and subsequent gene silencing was tested. PK-modifying anchors enhanced delivery of hsiRNA compounds after intravenous administration. Productive gene silencing was observed after 48 hours. The addition of larger PEG moieties did not interfere with gene silencing, indicating (without being bound by scientific theory) that RNA-induced silencing complex (RISC) loading and activity is comparable to that with the hsiRNA alone.

20 mg/kg tail vein injections were performed in female FVB/N mice (approximately 9-12 weeks old). Tissues were collected at 48 hours after injection and mRNA was quantified by QuantiGene b-DNA assay as described in Coles et al. 2015.

Figure 21:
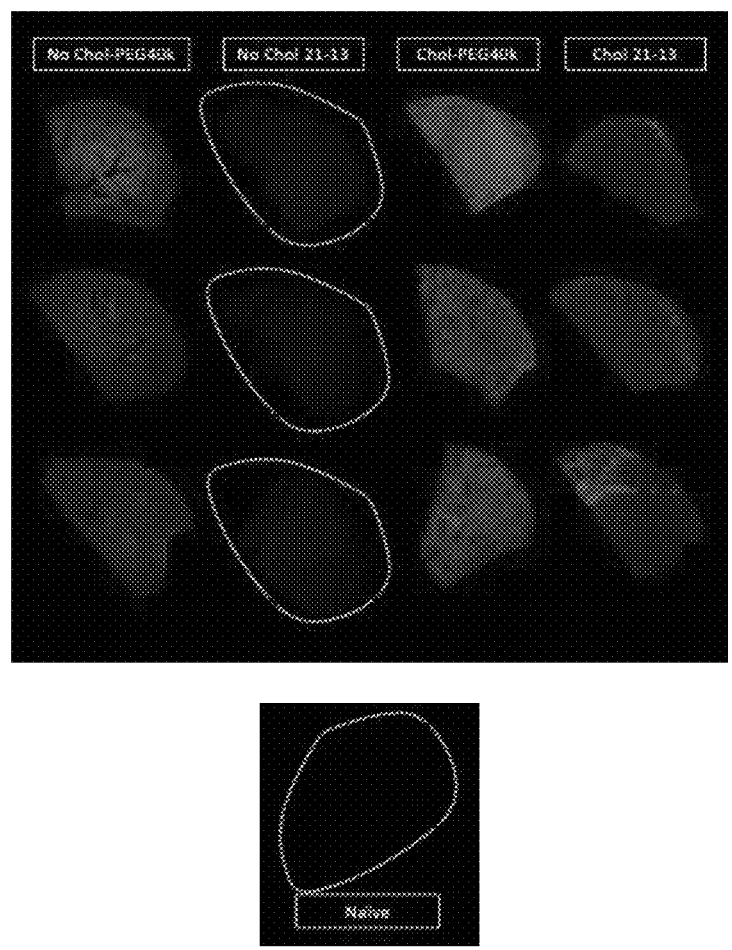
FIG. 21 depicts liver distribution after SC administration.
Figure 22:
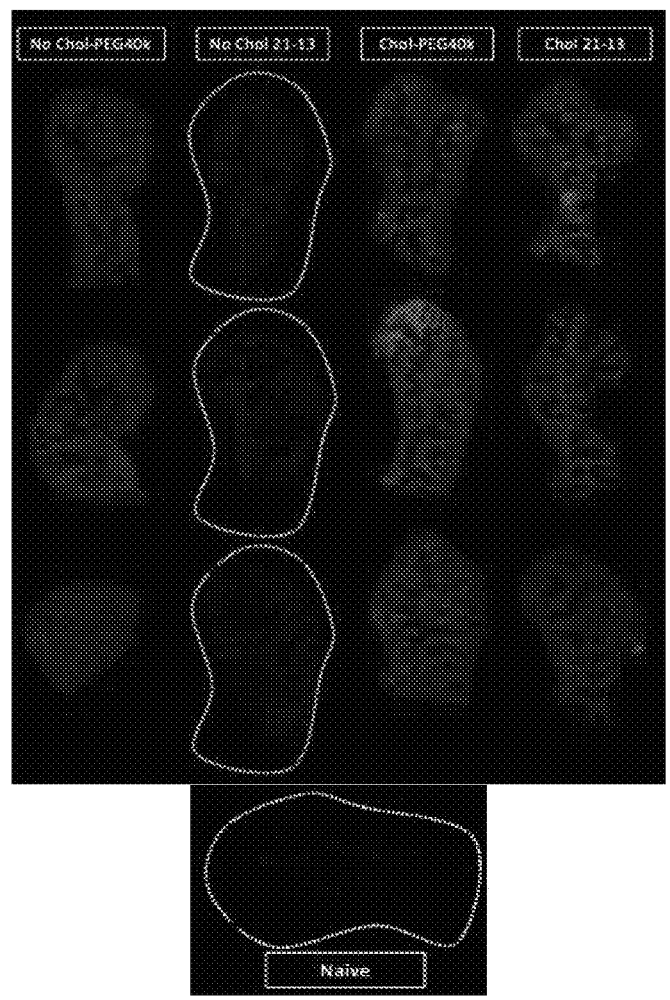
FIG. 22 depicts spleen distribution after SC administration.
Figure 23:
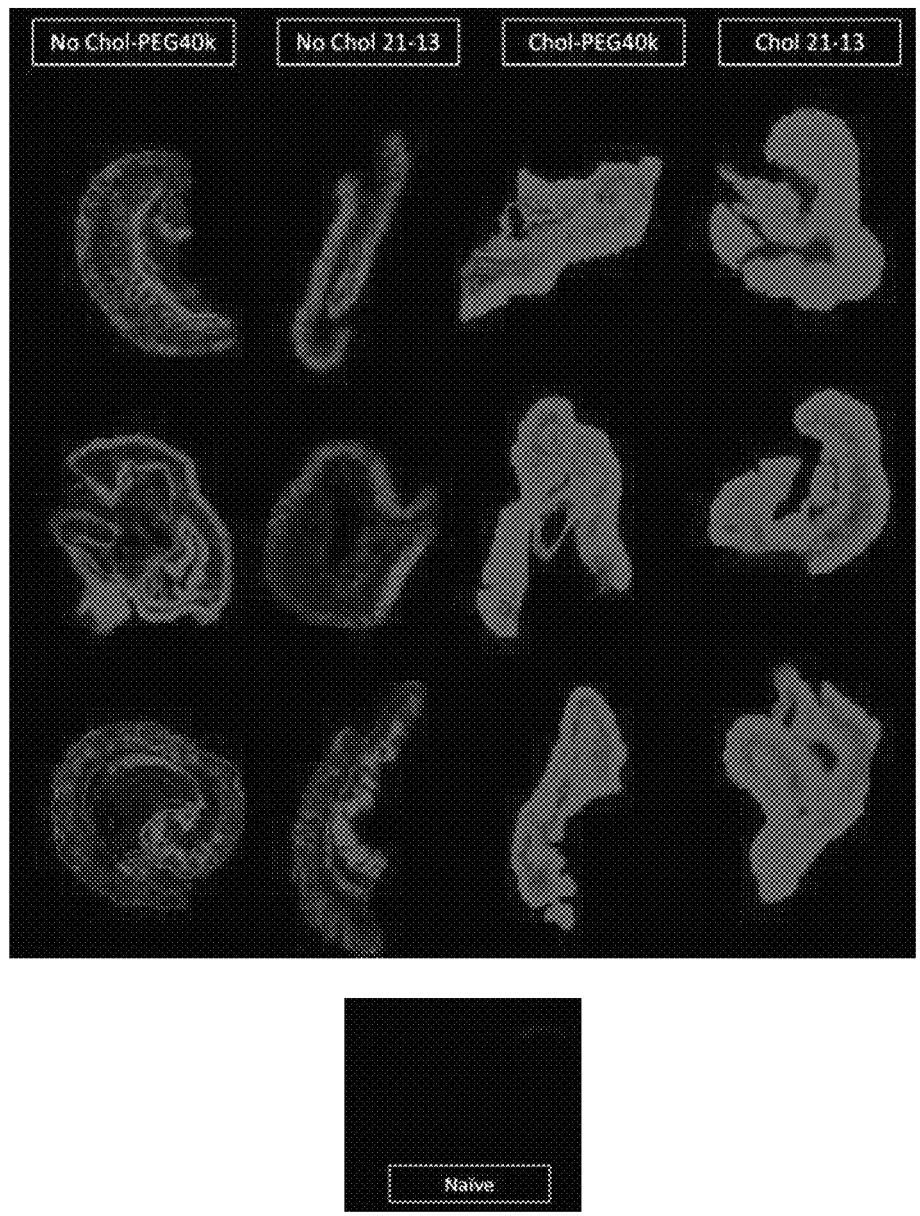
FIG. 23 depicts skin distribution after SC administration.

PK-modifying anchors also delivered hsiRNA compounds to the kidney (FIG. 20), the liver (FIG. 21), the spleen (FIG. 22) and the skin (FIG. 23) after subcutaneous administration.

Figure 4:
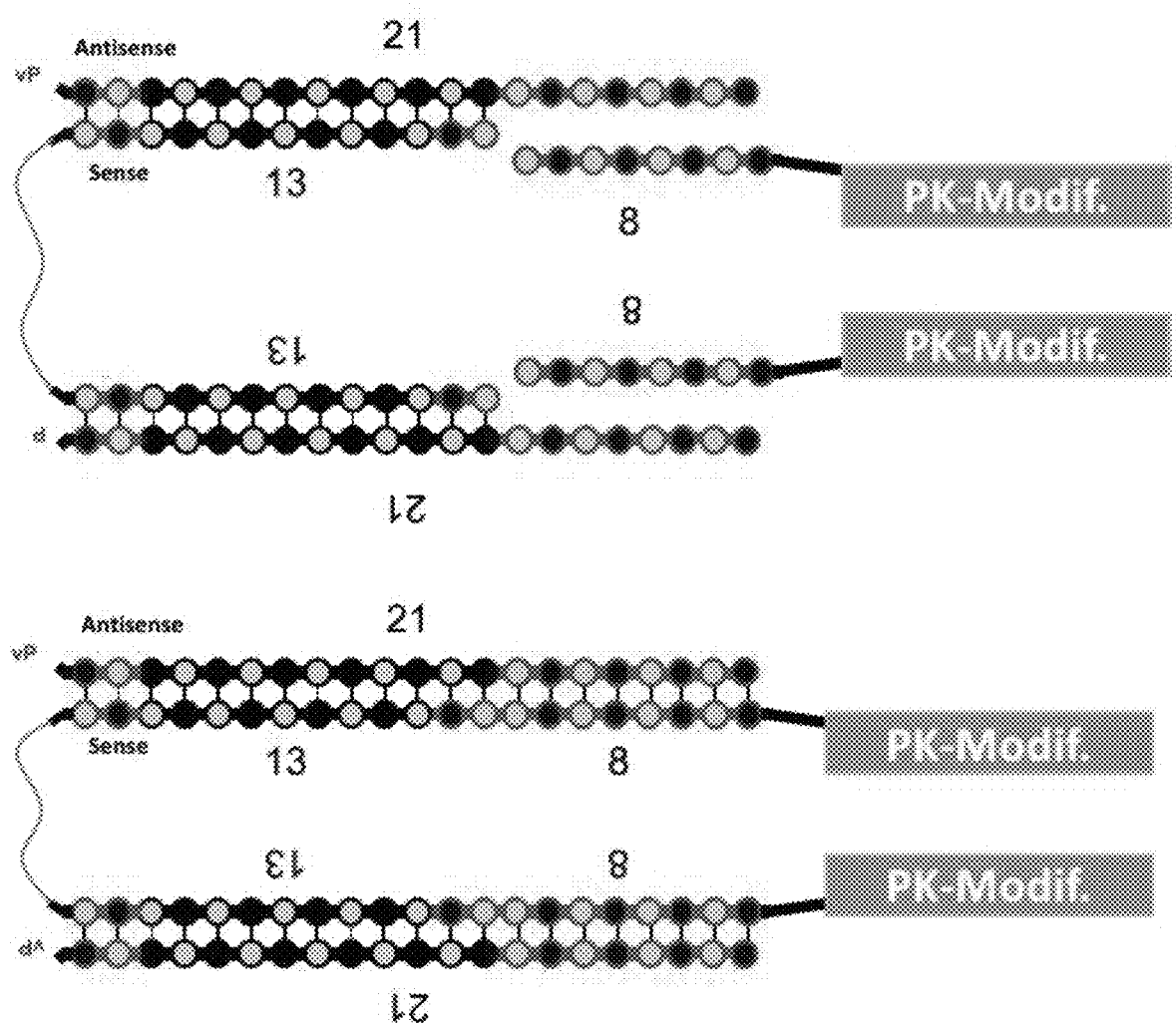
FIG. 4 schematically depicts two asymmetric siRNA duplexes linked together according to certain exemplary embodiments described further herein. As depicted, a PK-modifying moiety is attached to each oligonucleotide anchor such that, when the oligonucleotide anchors are bound to the siRNA duplexes, the siRNA construct comprises two PK-modifying moieties. In this embodiment, the top scaffold represents uses a dynamic PK modifying anchor and the bottom scaffold consists of a stably-attached PK modifier. Given the dynamic nature of the top scaffold, without intending to be limited by scientific theory, it is expected that this will allow for improved distribution and retention in vivo.
Figure 11A:
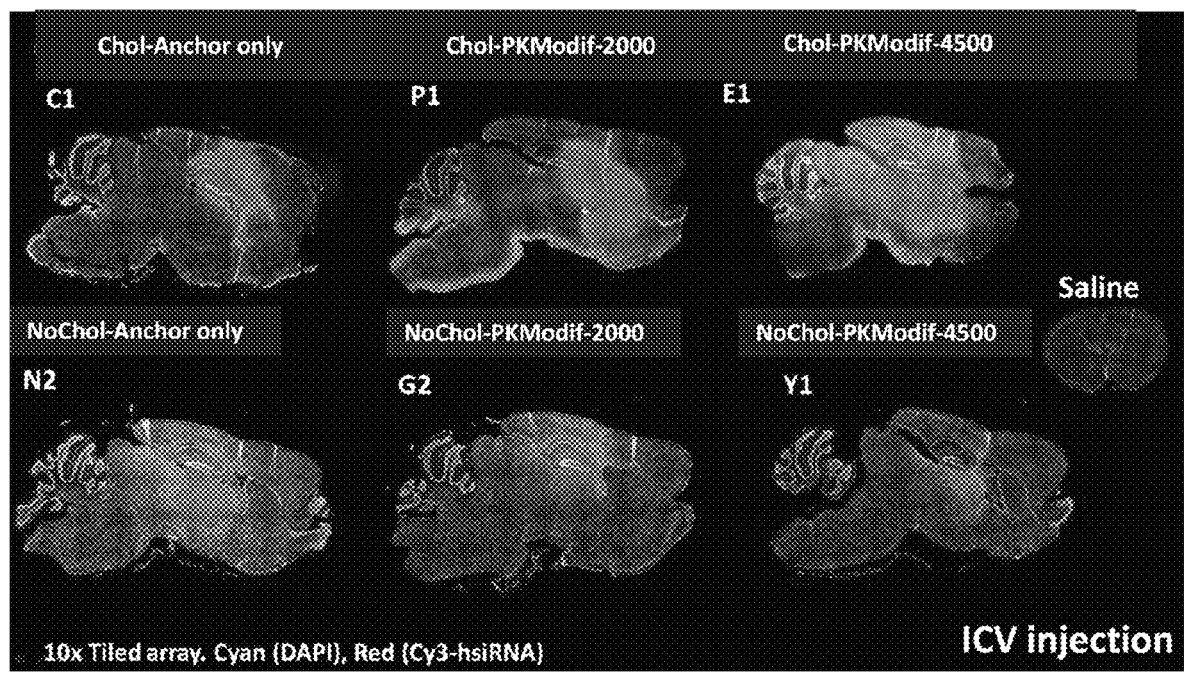
FIG. 11A-FIG. 11C depict the effect of PK-modifying anchors on in vivo biodistribution of hsiRNA compounds in the central nervous system after intracerebroventricular (FIG. 11A and FIG. 11B) and intrathecal injections (FIG. 11C).
Figure 11B:
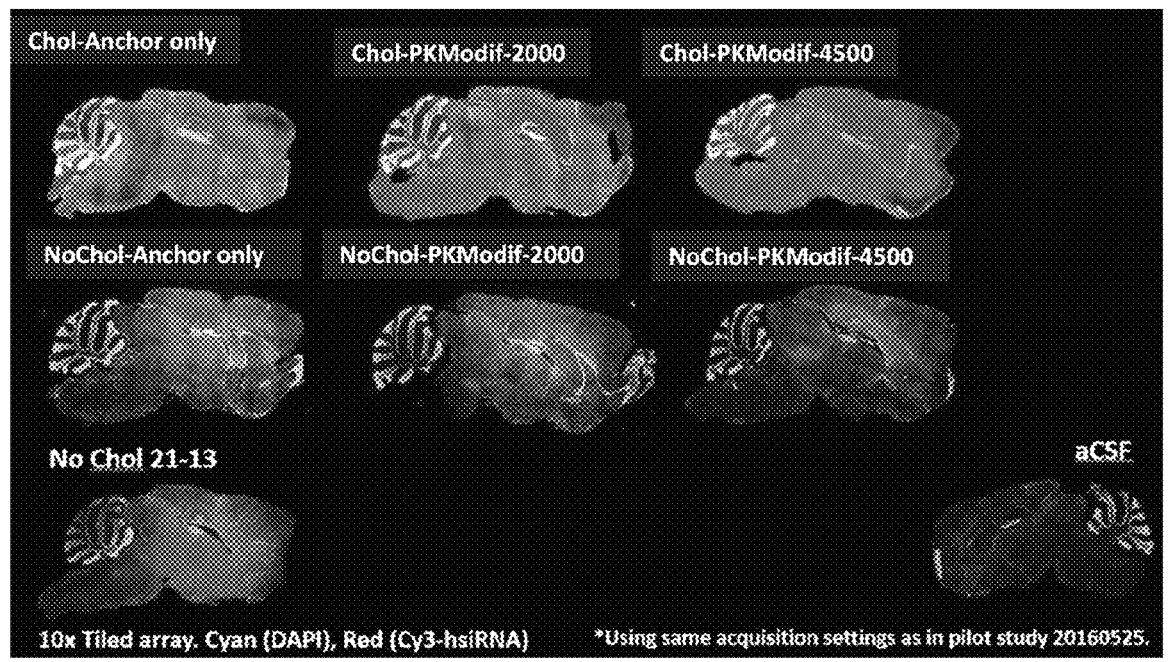
Figure 11C:
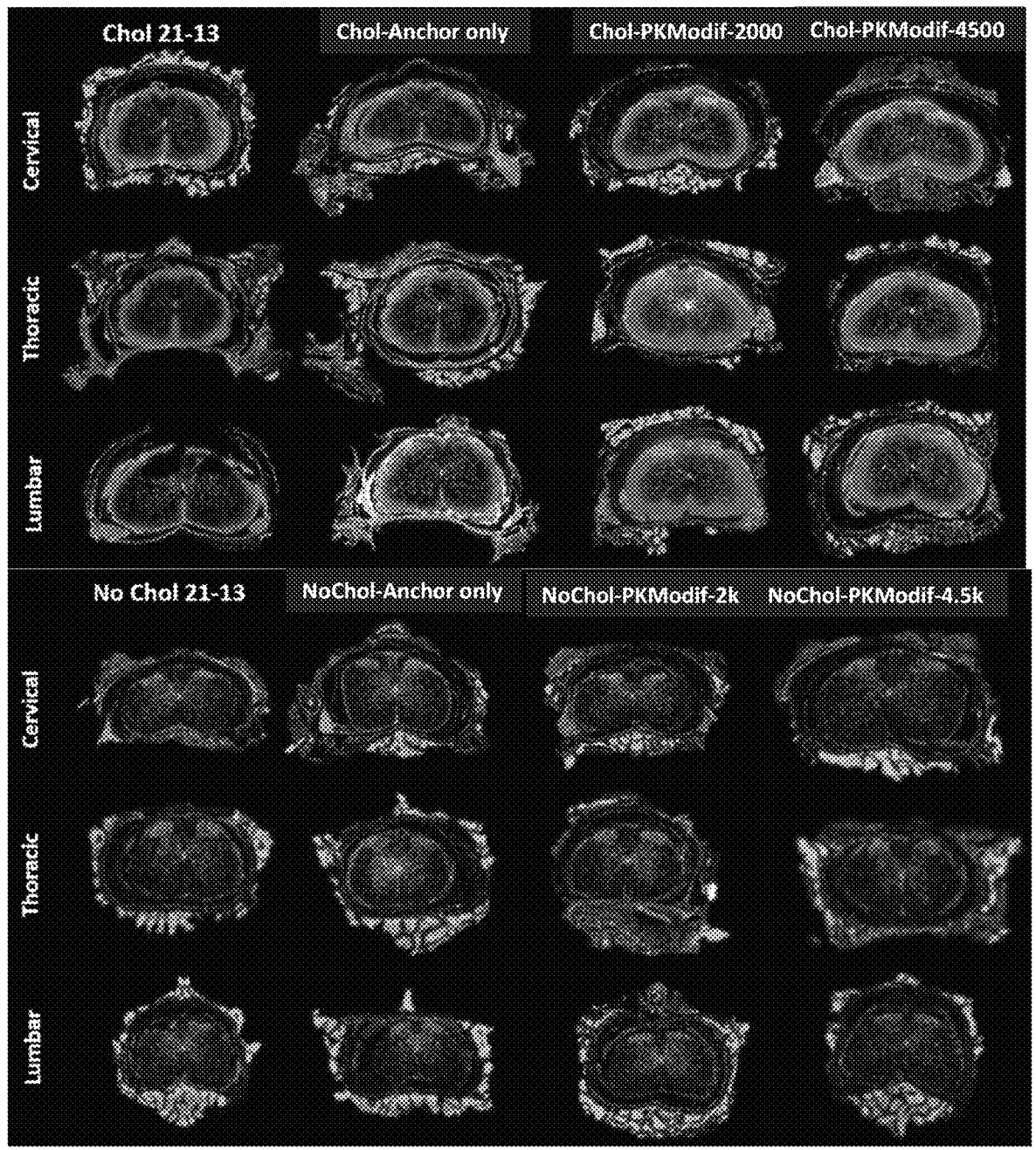
Figure 20:
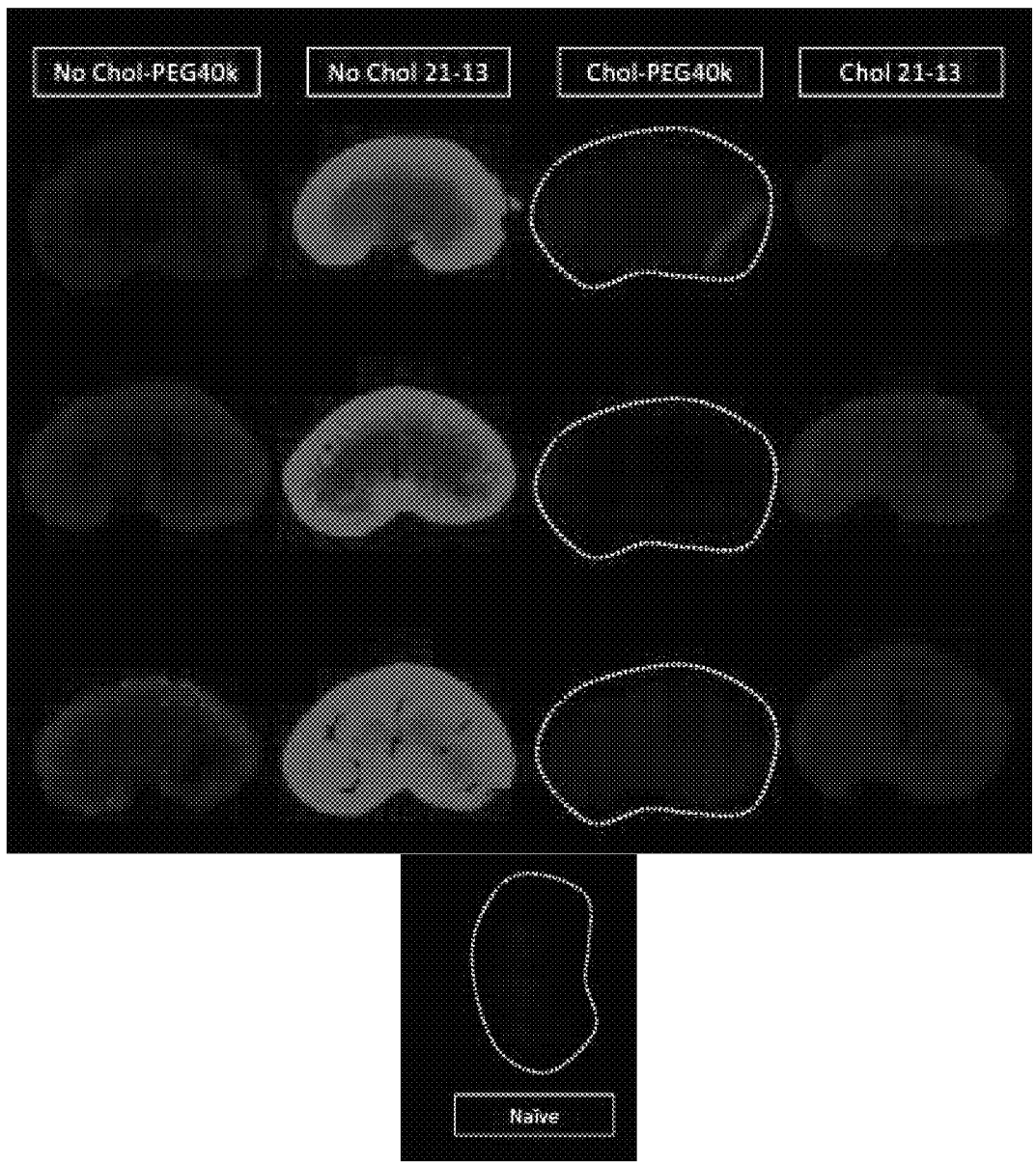

1.5 PK-Modifying Anchors Modulated In Vivo Biodistribution of hsiRNA Compounds within the Central Nervous System after Intracerebroventricular and Intrathecal Injections The effect of various hsiRNA constructs on in vivo biodistribution was tested following intracerebroventricular injection (FIG. 11A and FIG. 11B) or following intrathecal injection (FIG. 11C) in mice. In FIG. 11A, 4 nmols (or about 250 µg) of hsiRNAs were injected in the lateral venticulum to result in a concentration of about 2 nmol/ventricle. In FIG. 11B, 20 nmol of hsiRNAs were injected in the lateral venticulum to result in a concentration of about 10 nmol/ ventricle. The distribution of hsiRNA in mouse brain is shown in FIG. 11A and FIG. 11B. In FIG. 11C, 10 nmol of hsiRNAs were injected between L5 and L6 by intrathecal injection. The distribution of hsiRNA in mouse spine is shown in FIG. 11C.

hsiRNA constructs were made starting with a 21-mer oligonucleotide antisense strand and 13-mer oligonucleotide sense strand. The various attachments tested included: cholesterol only, cholesterol-anchor only, cholesterol-2000 Da PK-modifying anchor, cholesterol-4500 Da PK-modifying anchor, anchor only without cholesterol, 2000 Da PK-modifying anchor without cholesterol, 4500 Da PK-modifying anchor without cholesterol, and hsiRNA only without cholesterol. Mouse brains and spine tissues were collected 48 hours after injection and stained with DAPI (nuclei, blue). Brains and tissues were imaged using a Leica DMi8 fluorescent microscope.

PK-modifying anchors enabled unique spread and retention of highly lipophilic conjugates in the mouse brain after intracerebroventricular injections (FIG. 11A). Anchoring larger PEG moieties to hsiRNA cholesterol-conjugated compounds improved penetration in the brain parenchyma. PK-modifying anchors enable unique spread and retention of highly lipophilic conjugates in the mouse spine after intrathecal administrations (FIG. 11B). As observed for brain tissues, anchoring larger PEG moieties to hsiRNA cholesterol-conjugated compounds improved penetration in the parenchyma of the spinal cord.

Figure 29:
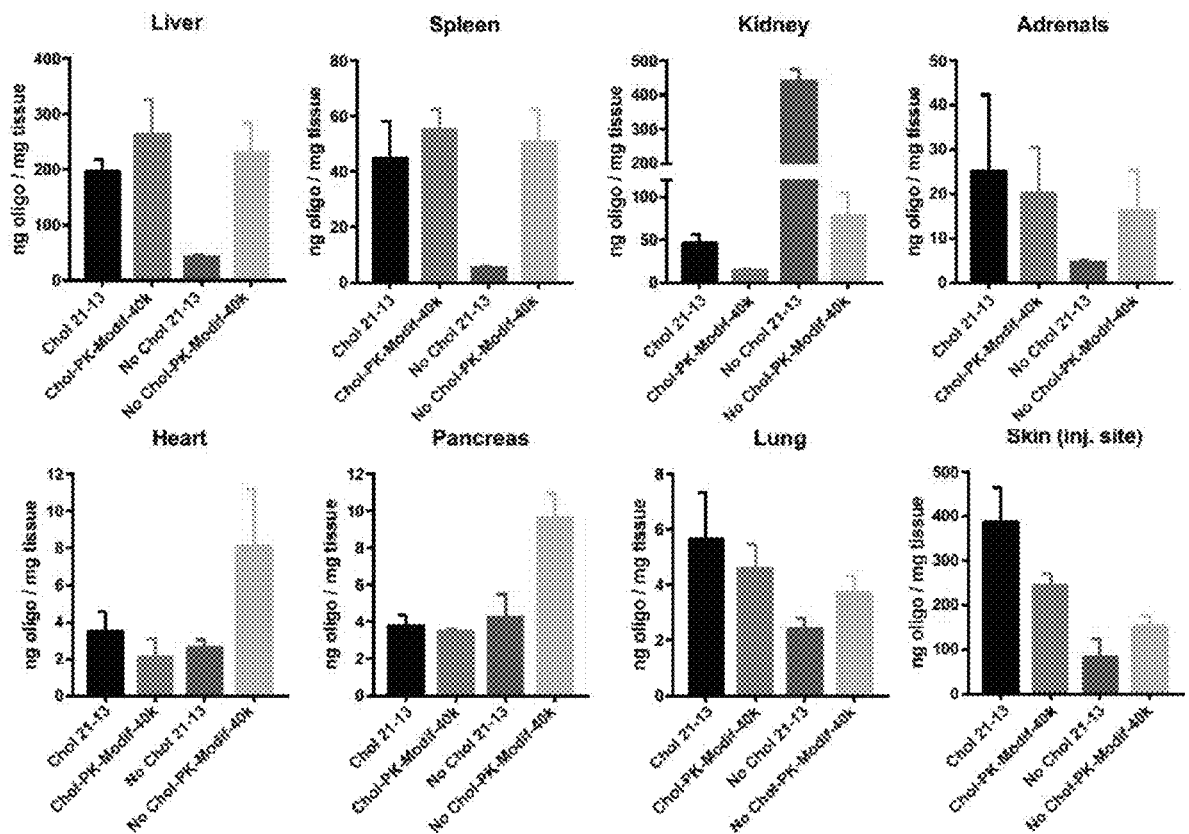
FIG. 29 graphically depicts that PK modifying anchors modulated systemic in vivo biodistribution of parent hsiRNA compounds. PK modifying anchors significantly affected biodistribution of unconjugated (red tones) and cholesterol-conjugated (black tones) hsiRNAs after subcutaneous injections. Broadly, PK modifying moiety improved delivery of unconjugated oligo to most organs. 20 mg/kg subcutaneous injections performed between shoulder blades in female FVB/N mice (approximately 9-12 weeks old). The antisense strand was quantified by PNA Hybridization assay after 48 hours. Polyethylene glycol (PEG) was used as a model PK modifying moiety, and a fully phosphorothioated 8-mer was used as a model anchor to modulate circulating times of the respective parent as21-s13 compound. Both PK modifying moiety and length and chemistry of the anchor may be adjusted according to the delivery aim/goal.
Figure 30:
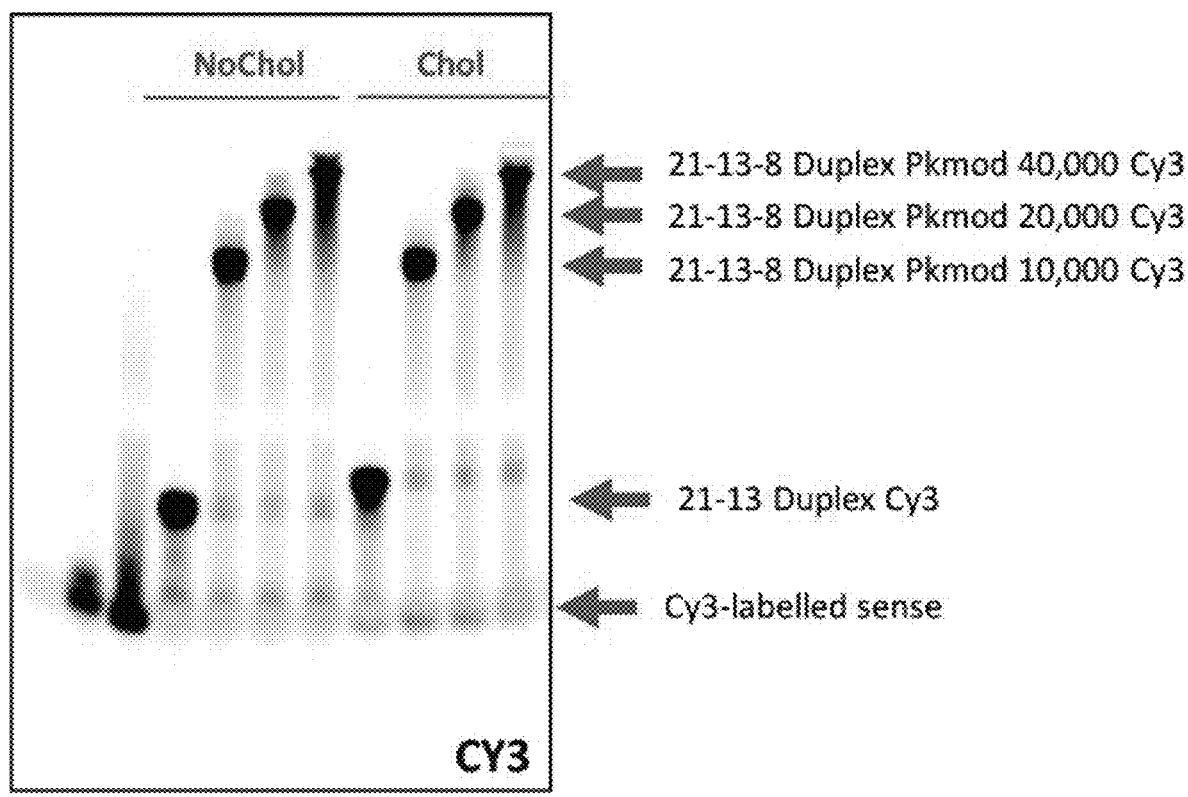
FIG. 30 depicts the results of a gel shift assay with PK-modifying anchors of 10 kDa, 20 kDa, and 40 kDa. Binding of the anchor was performed on asymmetric siRNA duplexes with and without a cholesterol conjugate. The asymmetric siRNA duplex antisense strand was 21 nucleotides in length, the sense strand was 13 nucleotides in length, and the anchor with complementarity to the antisense strand tail was 8 nucleotides in length. The asymmetric siRNA duplexes were Cy3 labeled at the sense strand 5' end.

1.6 PK-Modifying Anchors Dramatically Improved Blood/Plasma Circulating Times and Modulated Systemic in vivo Biodistribution After Subcutaneous Injection PK modifying anchors enhanced areas under the curve of (FIG. 28A) unconjugated and (FIG. 28B) cholesterol-conjugated hsiRNAs after subcutaneous injections. PK modifying anchors significantly affect biodistribution of unconjugated (red tones) and cholesterol-conjugated (black tones) hsiRNAs after subcutaneous injections (FIG. 29).

Figure 31:
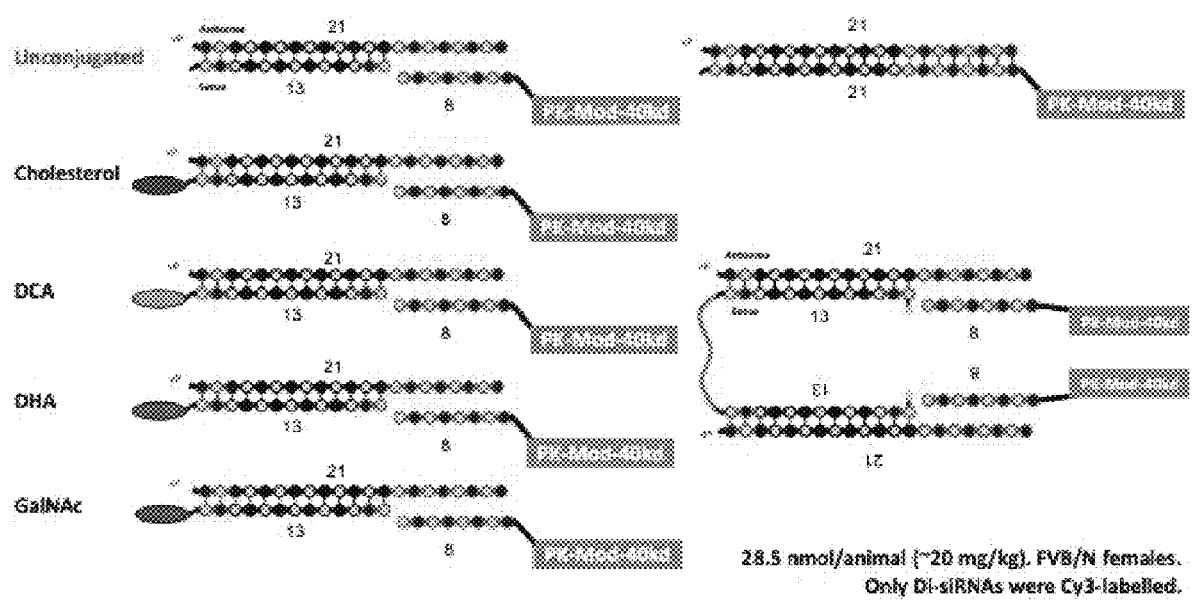
FIG. 31 depicts representative siRNA structures used for measuring the blood concentration profile and tissue distribution profile when administered systemically via intravenous and subcutaneous administration.

Example 2. Conjugated Oligonucleotides Comprising Dynamic Pharmacokinetic (PK)-Modifying Anchors 2.1 PK-Modifying Anchors PK-modifying anchors were paired with a panel of different conjugated asymmetric siRNAs, as depicted in FIG. 31. Specifically, siRNAs with 21-nucleotide antisense strands and 13-nucleotide sense strands were conjugate with one of cholesterol, DCA, DHA, or GalNAc. A Di-branch siRNA compound, where a linker joins two siRNAs at the 3' end of the sense strands, was also tested. Each conjugated asymmetric siRNA was paired with a PK-modifying anchor comprising a 40 kDa PEG moiety, wherein all internucleotide linkages are phosphorothioates.

2.2 PK-Modifying Anchors Dynamically Improved Blood/Plasma Circulating Times of siRNA Compounds Administered Intravenously As shown at FIG. 32, the effect of PK-modifying anchors on the blood/plasma circulating times of conjugated siRNAs was tested. It was determined that PK-modifying molecular anchors enhanced circulating times and areas under the curve of unconjugated siRNAs (FIG. 32A), GalNAc-conjugated siRNAs (FIG. 32B), DHA-conjugated siRNAs (FIG. 32C), Di-siRNAs (FIG. 32D), cholesterol-conjugated siRNAs (FIG. 32E), and DCA-conjugated siRNAs (FIG. 32F), after intravenous injections.

20 mg/kg tail vein injections were performed in female FVB/N mice (approximately 9-12 weeks old). The antisense strand was quantified by peptide nucleic acid (PNA) hybridization assay as previously described in Godinho et al. 2017 (Nucleic Acids Therapeutics). Briefly, this assay used a cy3-labelled PNA probe that hybridizes to the antisense strand, with subsequent quantification by HPLC.

2.3 PK-Modifying Anchors Modulated Systemic In Vivo Biodistribution of siRNA Compounds Administered Intravenously As shown at FIG. 33, the effect of PK-modifying anchors on biodistribution of the conjugated siRNAs of Example 2.2 were tested. Localization of siRNAs was tested with respect to pancreas, lung, heart, adrenal gland, spleen, kidney, muscle, and liver. As with Example 2.2, of unconjugated siRNAs (FIG. 33A), GalNAc-conjugated siRNAs (FIG. 33B), DHA-conjugated siRNAs (FIG. 33C), Di-siRNAs (FIG. 33D), cholesterol-conjugated siRNAs (FIG. 33E), and DCA-conjugated siRNAs (FIG. 33F), were tested. The results demonstrate that the PK-modifying anchors enhance biodistribution of the conjugated siRNAs across numerous tissues. The PK-modifying anchors also reduce kidney accumulation of the conjugated siRNAs. The kidney is a clearance tissue and avoidance of the kidney may increase the serum half-life and biodistribution of the conjugated siRNAs.

These results also demonstrate the unexpected enhancement of liver delivery that the PK-modifying anchors confer on a GalNAc-conjugated siRNA. As shown in FIG. 33B, the amount of GalNAc-conjugated siRNA with the PK-modifying anchor is more than doubled compared to the GalNAc-conjugated siRNA without the PK-modifying anchor. The GalNAc conjugate is known to promote liver delivery for siRNAs, however, the addition of the PK-modifying anchors promoted a higher degree of liver delivery beyond the GalNAc conjugate and may be useful to enhance the therapeutic efficacy of GalNAc-conjugated siRNAs.

Figures 34A, 34B:
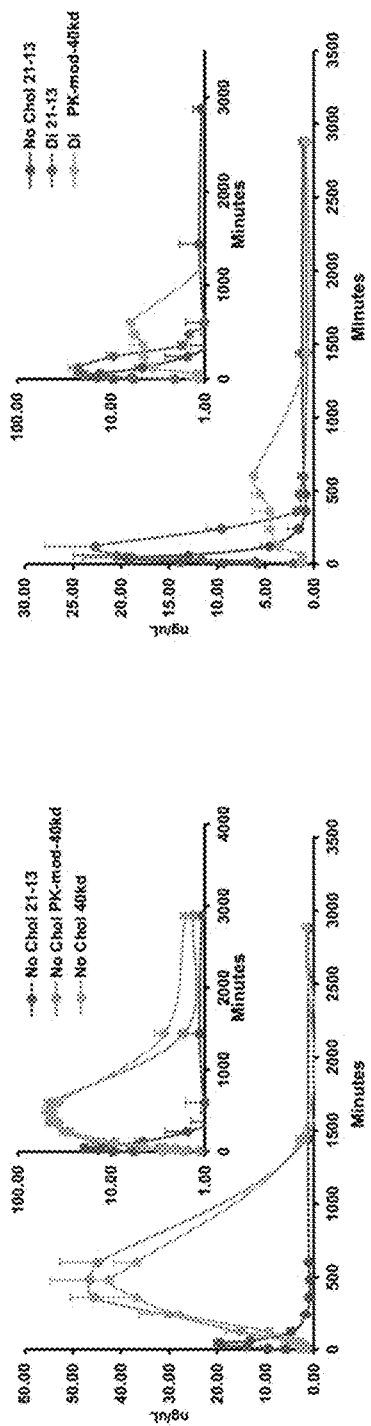
FIG. 34A-FIG. 34B depict the blood concentration profile of PK-modifying anchors paired with an unconjugated siRNA (FIG. 34A) or a Di-branched siRNA (FIG. 34B), as depicted in FIG. 31. Polyethylene glycol (PEG) was used as the PK-modifying polymer. The siRNA asymmetric duplex contained a 21-mer oligonucleotide antisense strand and a 13-mer oligonucleotide sense strand. A fully phosphorothioated 8-mer oligonucleotide anchor was used. 20 mg/kg subcutaneous injections were performed in female FVB/N mice (at approximately 9-12 weeks old). The antisense strand was quantified using a peptide nucleic acid hybridization assay after 48 hours.

2.4 PK-Modifying Anchors Dynamically Improved Blood/Plasma Circulating Times of siRNA Compounds Administered Subcutaneously As shown at FIG. 34, the effect of PK-modifying anchors on the blood/plasma circulating times of unconjugated siRNAs (FIG. 34A) and Di-siRNAs (FIG. 34B) was determined, after subcutaneous injection.

20 mg/kg subcutaneous injections were performed in female FVB/N mice (approximately 9-12 weeks old). The antisense strand was quantified by peptide nucleic acid (PNA) hybridization assay as previously described in Godinho et al. 2017 (Nucleic Acids Therapeutics).

Figures 35A, 35B:
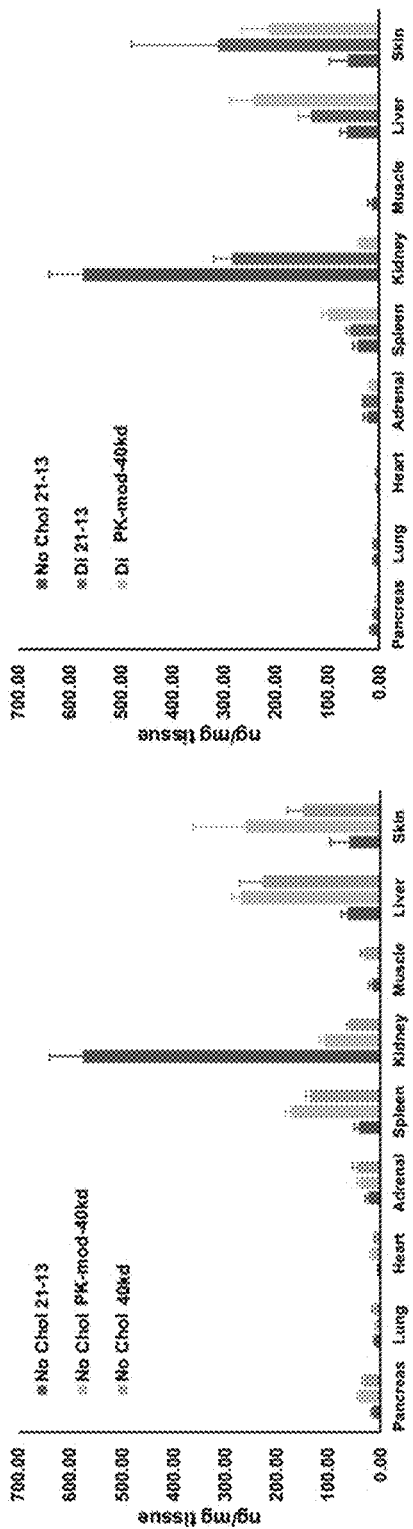
FIG. 35A-FIG. 35B depict the tissue distribution profile of PK-modifying anchors paired with an unconjugated siRNA (FIG. 35A) or a Di-branched siRNA (FIG. 35B), as depicted in FIG. 31. Polyethylene glycol (PEG) was used as the PK-modifying polymer. The siRNA asymmetric duplex contained a 21-mer oligonucleotide antisense strand and a 13-mer oligonucleotide sense strand. A fully phosphorothioated 8-mer oligonucleotide anchor was used. 20 mg/kg subcutaneous injections were performed in female FVB/N mice (at approximately 9-12 weeks old). The antisense strand was quantified using a peptide nucleic acid hybridization assay after 48 hours.

2.5 PK-Modifying Anchors Modulated Systemic In Vivo Biodistribution of siRNA Compounds Administered Subcutaneously As shown at FIG. 35, the effect of PK-modifying anchors on biodistribution of the siRNAs of Example 2.4 were tested. Localization of siRNAs was tested with respect to pancreas, lung, heart, adrenal gland, spleen, kidney, muscle, and liver. As with Example 2.4, of unconjugated siRNAs (FIG. 35A) and Di-siRNAs (FIG. 35B), were tested.

Figure 36:
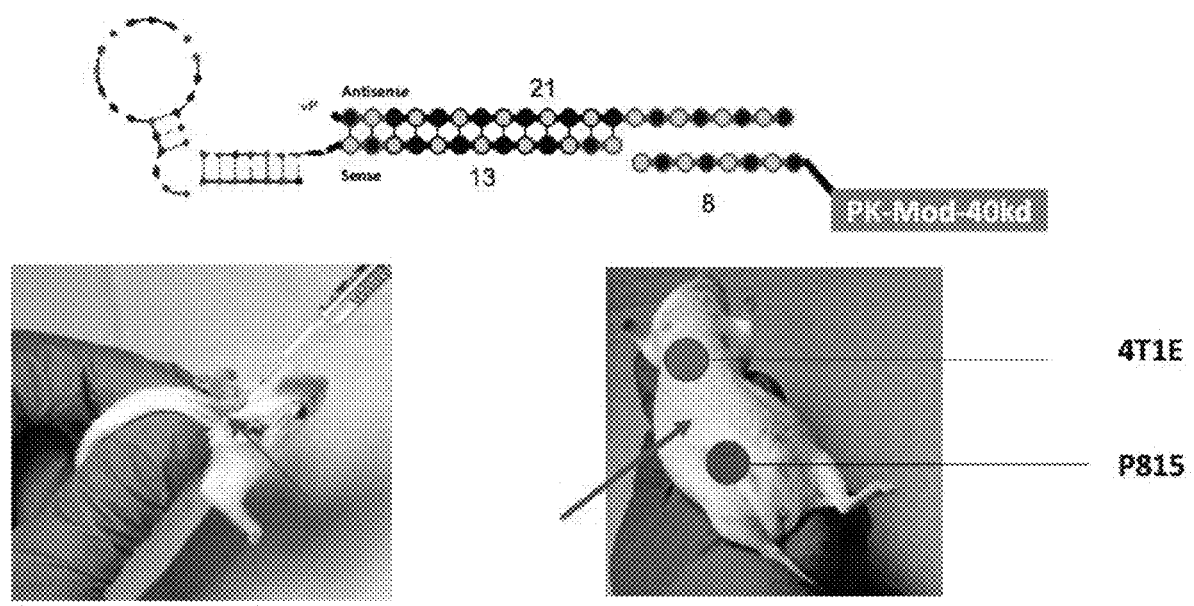
FIG. 36 depicts the delivery scheme for an aptamer-siRNA chimera with a PK-modifying anchor. 20 mg/kg subcutaneous injections were performed in tumor bearing Balb-c mice. The mice had the 4T1E breast cancer cell line tumor and the P815 mastocytoma tumor.
Figures 37A, 37B:
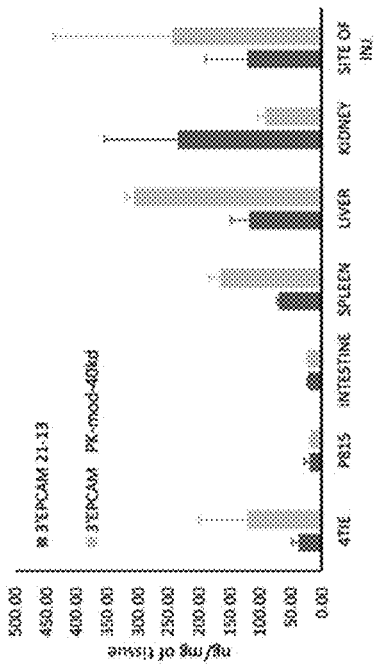
FIG. 37A-FIG. 37B depict the blood concentration profile (FIG. 37A) and tissue distribution profile (FIG. 37B) of PK-modifying anchors paired with an aptamer-siRNA chimera, as depicted in FIG. 36. The aptamer binds to the EPCAM receptor for delivery to the 4T1E tumor. Polyethylene glycol (PEG) was used as the PK-modifying polymer. The siRNA asymmetric duplex contained a 21-mer oligonucleotide antisense strand and a 13-mer oligonucleotide sense strand. A fully phosphorothioated 8-mer oligonucleotide anchor was used. The aptamer was conjugated to the sense strand 3' end. 20 mg/kg subcutaneous injections were performed in female FVB/N mice (at approximately 9-12 weeks old). The antisense strand was quantified using a peptide nucleic acid hybridization assay after 48 hours.

2.6 PK-Modifying Anchors Modulated Blood/Plasma Circulating Times And Systemic In Vivo Biodistribution of Aptamer-siRNA Chimeric Compounds Administered Subcutaneously As shown at FIG. 36 and FIG. 37, the effect of a PK-modifying anchor on the blood/plasma circulating times (FIG. 37A) and biodistribution (FIG. 37B) of aptamer-siRNA chimeras were tested. An aptamer that binds the EPCAM receptor was conjugated to the 3' end of an siRNA sense strand.

20 mg/kg subcutaneous injections were performed in tumor-bearing Balb-c mice. The mice contained both the 4T1E cell-derived tumor and the P815 cell-derived tumor. The sense strand was quantified by peptide nucleic acid (PNA) hybridization assay as previously described in Godinho et al. 2017 (Nucleic Acids Therapeutics). Tissue was collected for the assay 48-hours after injection. In this assay, the EPCAM-binding aptamer-siRNA conjugate was taken up by the 4T1E tumor, which expresses the EPCAM receptor, while the P815 tumor was used as a negative control. As demonstrated by FIG. 37A and FIG. 37B, the PK-modifying anchors enhanced circulating times and improved delivery to target tumors by two to four-fold compared to aptamer-siRNA conjugates without a PK-modifying anchor.

Figure 38A:
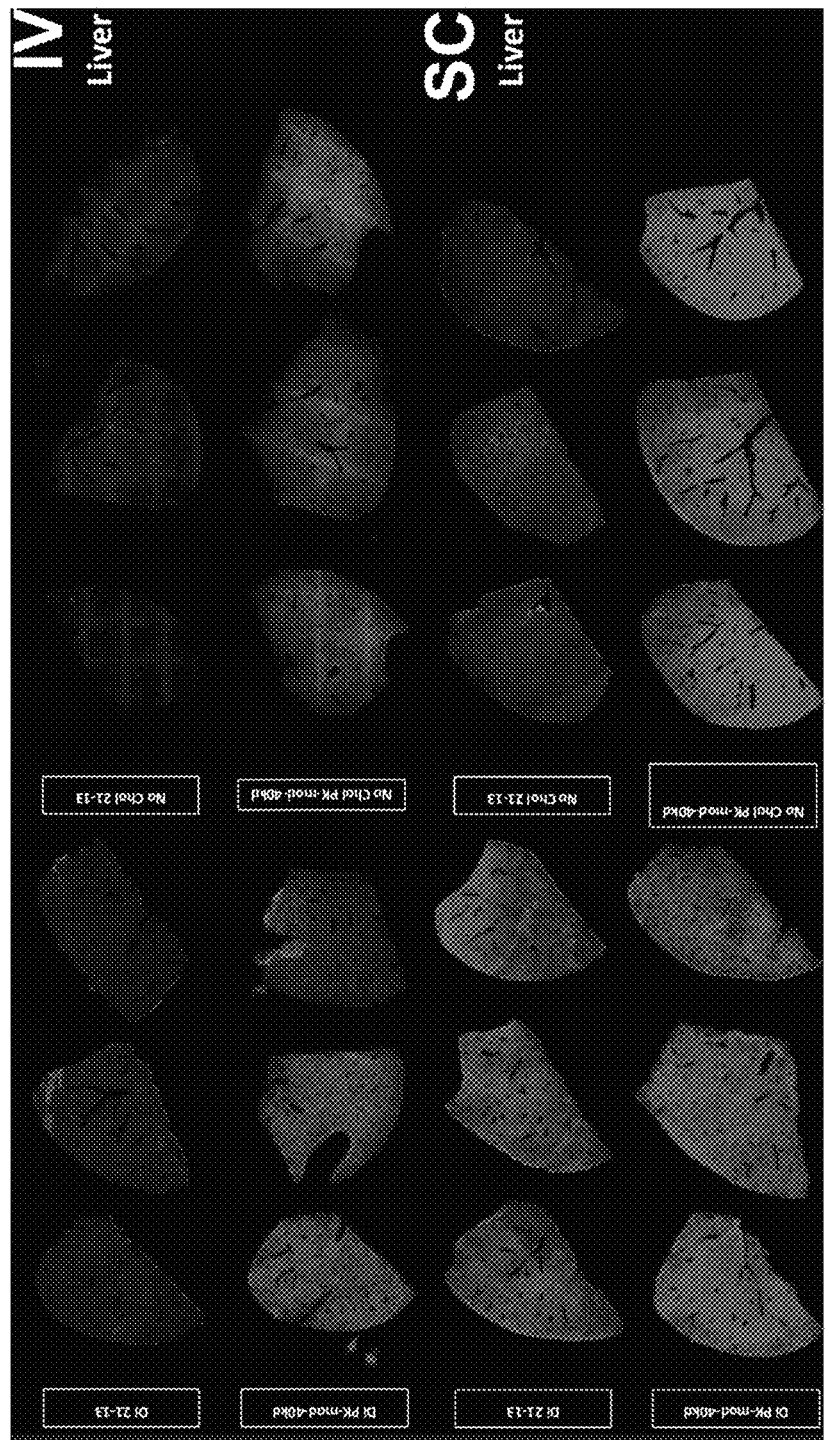
FIG. 38A-FIG. 38C depict the tissue distribution profile of PK-modifying anchors paired with an unconjugated siRNA or a Di-branched siRNA. The siRNAs were delivered via intravenous or subcutaneous administration. Polyethylene glycol (PEG) was used as the PK-modifying polymer.
Figure 38B:
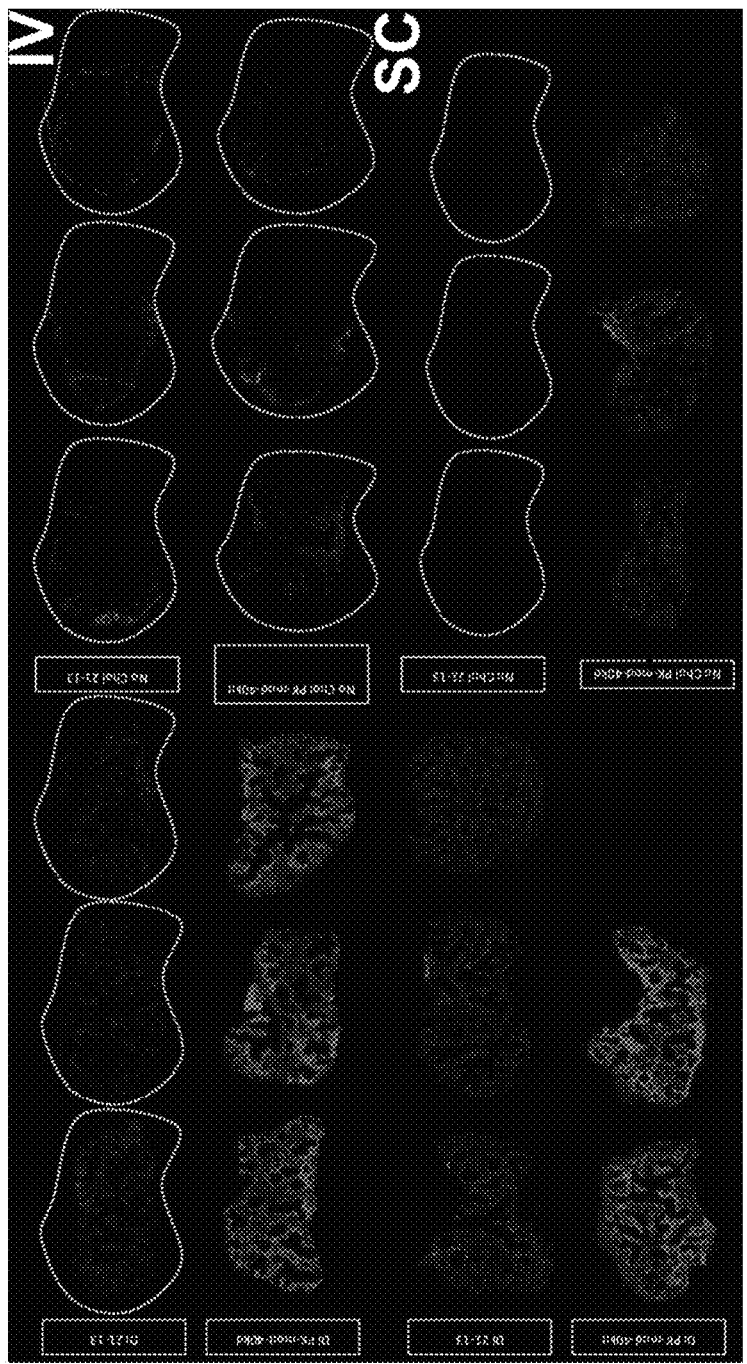
Figure 38C:
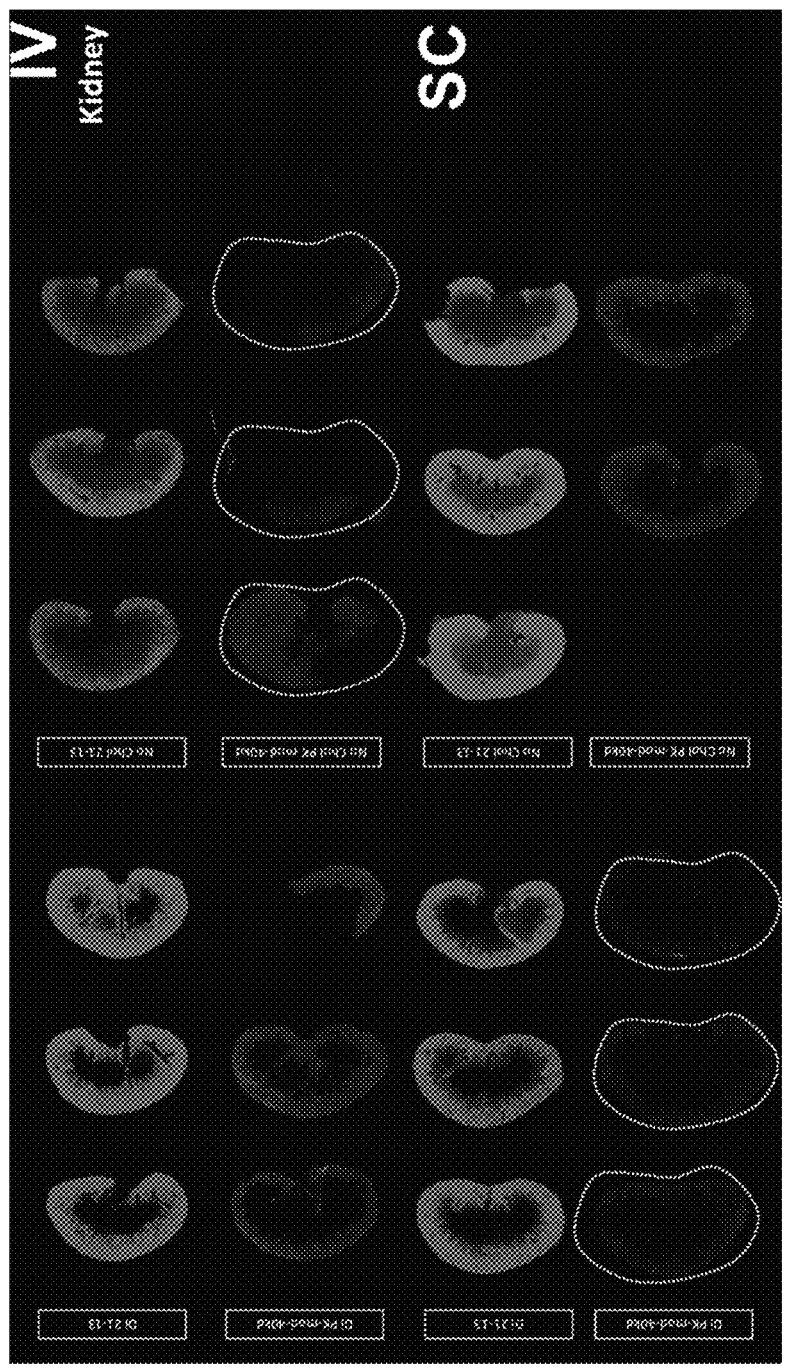

2.7 PK-Modifying Anchors Modulated Systemic In Vivo Biodistribution of Di-branched siRNA Compounds Administered Intravenously And Subcutaneously As shown at FIG. 38, the effect of PK-modifying anchors on biodistribution of unconjugated siRNAs and Di-siRNAs was determined, comparing intravenous and subcutaneous injection. Localization of siRNAs was tested with respect to liver (FIG. 38A), spleen (FIG. 38B), and kidney (FIG. 38C). The results demonstrate that PK-modifying anchors enhanced delivery of unconjugated and Di-siRNA parent asymmetric siRNAs to the liver and other secondary distribution organs after SC and IV administration. PK-modifying anchors also reduced kidney clearance for both siRNA scaffolds. The experiments were performed in triplicate, with florescent tissues images shown for each of the three mice used in each condition.

Figure 39:
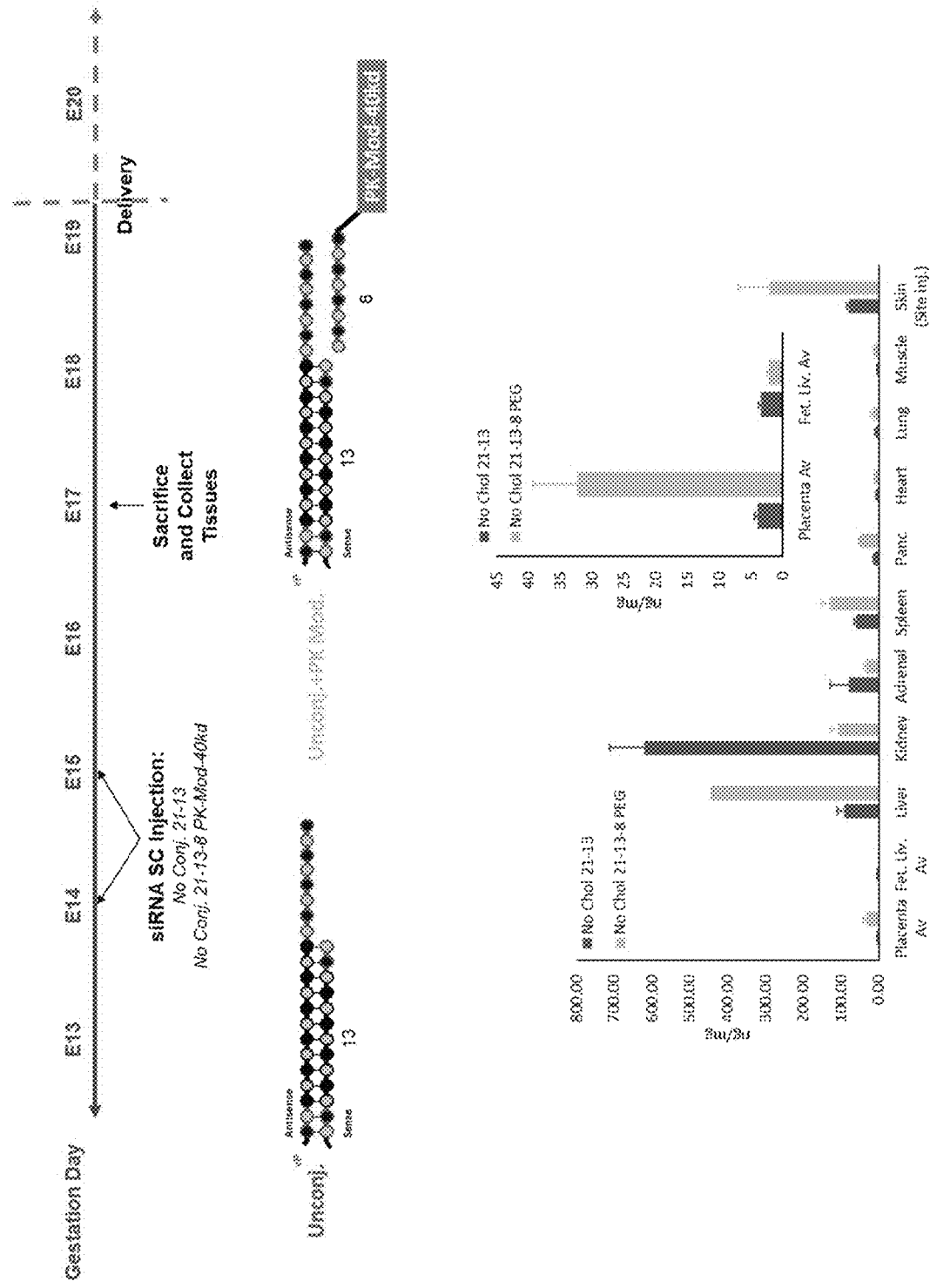
FIG. 39 depicts tissue distribution to the mouse placenta with PK-modifying anchors paired with an unconjugated siRNA. The siRNAs were delivered via subcutaneous administration. Two doses of 20 mg/kg were delivered, as depicted in the timeline. Pregnant female FVB/N mice (~9-12 weeks old, 4 mice/group) were used and tissues were collected 48 hours after the last injection. A peptide nucleic acid (PNA) hybridization assay was used for antisense quantification.

2.8 PK-Modifying Anchors Modulated Systemic In Vivo Biodistribution To The Placenta As shown at FIG. 39, the effect of PK-modifying anchors on biodistribution of unconjugated siRNAs to the mouse placenta was determined. Two separate 20 mg/kg subcutaneous injections were performed in pregnant female FVB/N mice (approximately 9-12 weeks old, 4 mice/group). Tissues were collected 48-hours after the last injection. The antisense strand was quantified by peptide nucleic acid (PNA) hybridization assay as previously described in Godinho et al. 2017 (Nucleic Acids Therapeutics). The results demonstrated that the PK-modifying anchors enhanced distribution by ten-fold to the placenta compared to siRNAs without PK-modifying anchors.

2.9 PK-Modifying Anchors Enable Gene Silencing In The Placenta

Figure 40:
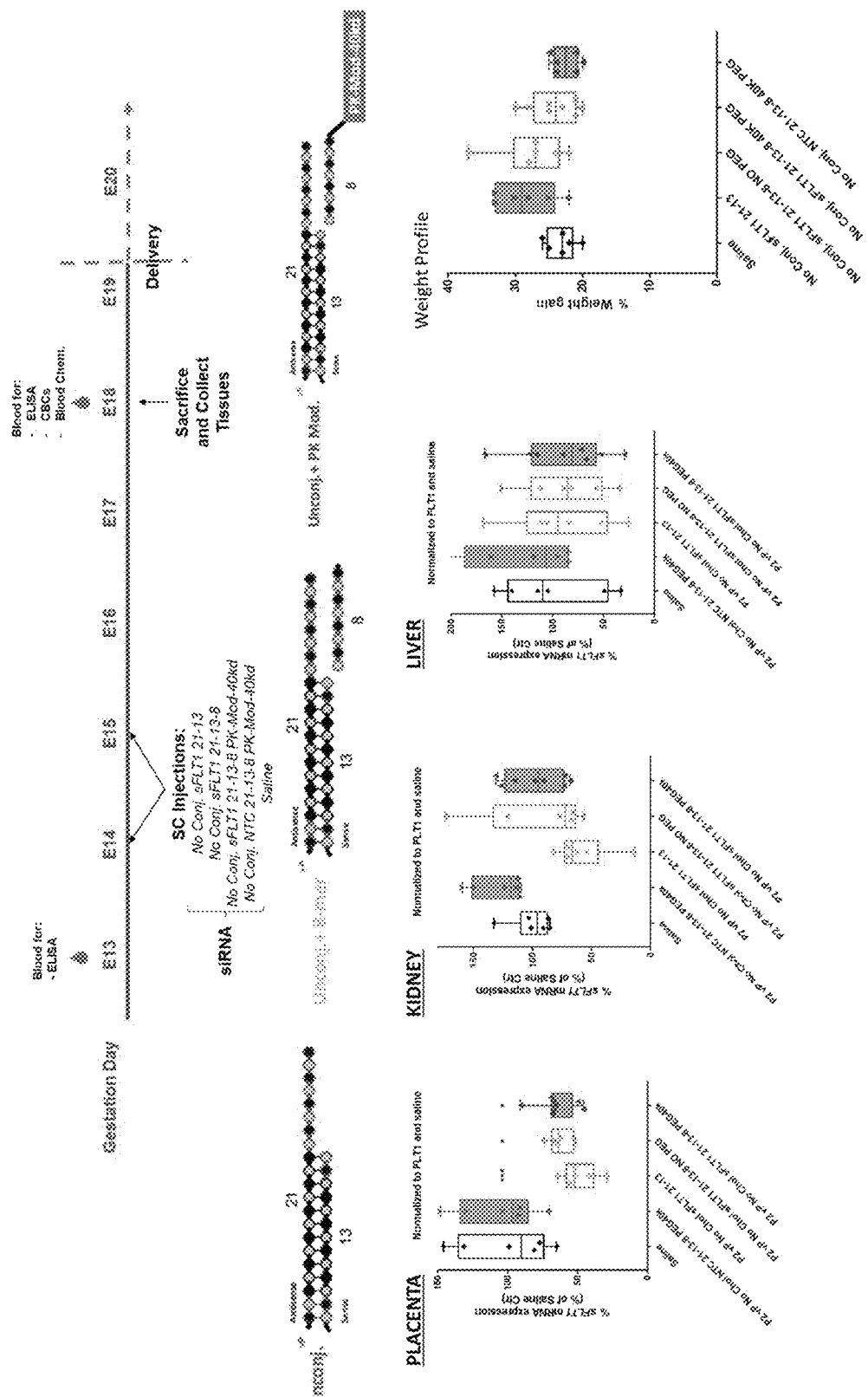
FIG. 40 depicts the efficacy of sFlt-1 mRNA silencing in select tissues with PK-modifying anchors paired with an unconjugated siRNA. The siRNAs were delivered via subcutaneous administration. Two doses of 20 mg/kg were delivered, as depicted in the timeline. Pregnant female FVB/N mice (~9-12 weeks old, 6-8 mice/group) were used. A branched DNA (bDNA) was used for mRNA quantification. The levels of the target mRNA, sFlt-1, were measured in placenta, liver, and kidney tissue. The weight profile of mice was also measured to demonstrate that using the PK-modified anchors did not cause acute systemic toxicity. A panel of blood chemistries and complete blood counts were also determined to demonstrate that using the PK-modified anchors did not cause acute systemic toxicity.

As shown at FIG. 40, the effect of PK-modifying anchors on target mRNA silencing of unconjugated siRNAs to the mouse placenta was determined. The experiment as recited in Example 2.9 was performed. The siRNAs employed target the sFlt-1 mRNA. The relative levels of sFlt-1 mRNA were determined using a branched DNA (bDNA) assay. The results demonstrate that target mRNA silencing with PK-modifying anchors was comparable to siRNAs without PK-modifying anchors. To demonstrate that the PK-modifying anchors do not cause acute systemic toxicity, the weight profile (% weight gain), blood chemistries, and complete blood cell counts of the mice were determined. The results demonstrated that weight profile blood chemistries, and complete blood cell counts of the mice were comparable between saline injected controls and PK-modifying anchor-injected mice. These results demonstrated that the PK-modifying anchors do not cause acute systemic toxicity.

Figure 41:
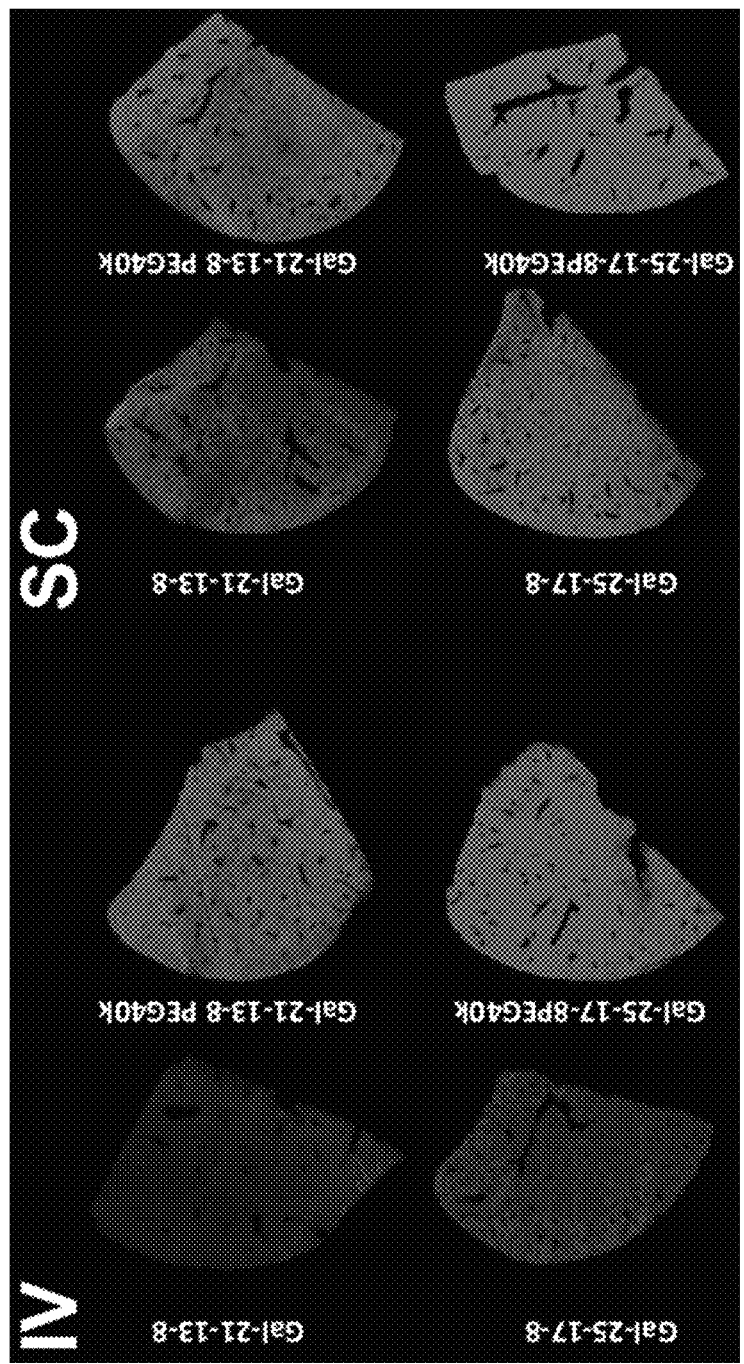
FIG. 41 depicts delivery of GalNAc-conjugated siRNAs to the liver via intravenous or subcutaneous administration. The distribution of 21-13-8 and 25-17-8 siRNA-PK-modifying anchors were compared. The 25-17-8 siRNA-PK-modifying anchor contained a conserved sequence from nucleotide position 18 to 25 in the 25-nucleotide antisense strand, which made up the antisense strand tail of the asymmetric siRNA. This conserved sequence tail of 8 nucleotides was complementary to the 8-nucleotide anchor.

2.10 PK-Modifying Anchors Modulated In Vivo Liver Biodistribution With GalNAc-Conjugated siRNAs As shown at FIG. 41, the effect of PK-modifying anchors on biodistribution to the liver with GalNAc-conjugated siRNAs was determined. The assay employed two different types of asymmetric siRNAs. The first was an siRNA with a 21-nucleotide antisense strand, a 13-nucleotide sense strand, and an 8-nucleotide anchor (denoted 21-13-8). The second was an siRNA with a 25-nucleotide antisense strand, a 17-nucleotide sense strand, and an 8-nucleotide anchor (denoted 25-17-8). The results demonstrated that the PK-modifying anchors enhanced distribution to the liver compared to siRNAs without PK-modifying anchors, for both intravenous and subcutaneous delivery, and in both the 21-13-8 siRNA format and the 25-17-18 siRNA format. This enhancement was particularly strong for hepatocytes in the liver. These results also demonstrate the unexpected enhancement of liver delivery that the PK-modifying anchors confer on a GalNAc-conjugated siRNA. As noted above in Example 2.3. the GalNAc conjugate is known to promote liver delivery for siRNAs, however, the addition of the PK-modifying anchors promoted a higher degree of liver delivery beyond the GalNAc conjugate and may be useful to enhance the therapeutic efficacy of GalNAc-conjugated siRNAs.

Example 3. Development Of A Conserved Universal Oligonucleotide Anchor Sequence

The above recited experiments of Example 1 and Example 2 were performed with an sFlt-1 mRNA-targeting asymmetric siRNA. This siRNA is of the 21-13 (antisense strand length-sense strand length) format. Accordingly, there is an 8-nucleotide long antisense tail to which the 8-nucleotide anchor sequence may bind. The tail sequence of the sFlt-1 mRNA-targeting asymmetric siRNA employed a G/C nucleotide rich tail sequence (G/C nucleotide content of 87.5%). A siRNA with a G/C nucleotide poor sequence was tested to determine if the PK-modifying anchors would successfully bind to their target antisense strand tail sequences. The sFlt-1 siRNA sequences and Htt mRNA-targeting siRNA sequences are recited below:
HTT10150:
Antisense strand, 21-nucleotide:
V(mU)#(fU)#(mA)(fA)(mU)(fC)(mU)(fC)(mU)(fU)(mU) (fA)(mC)#(fU)#(mG)#(fA)#(mU)#(fA)#(mU)#(fA)#(mC)
PK-modifying anchor, 8-nucleotide with a 40 kDa PEG moiety:
40k(mG)#(fU)#(mA)#(fU)#(mA)#(fU)#(mC)#(fA)
PK-modifying anchor, 6-nucleotide with a 40 kDa PEG moiety:
40k(mG)#(fU)#(mA)#(fU)#(mA)#(fU)
sFLT1-2283:
Antisense strand, 21-nucleotide:
V(mU)#(fA)#(mA)(fA)(mU)(fU)(mU)(fG)(mG)(fA)(mG) (fA)(mU)#(fC)#(mC)#(fG)#(mA) #(fG)#(mC)#(fG)#(mC)
Sense strand, 13-nucleotide:
(fA)#(mU)#(fC)(mU)(fC)(mC)(fA)(mA)(fA)(mU)(fU)# (mU)#(fA)
PK-modifying anchor, 8-nucleotide with a 40 kDa PEG moiety:
40k(mG)#(fC)#(mG)#(fC)#(mU)#(fC)#(mG)#(fG)

Figure 42:
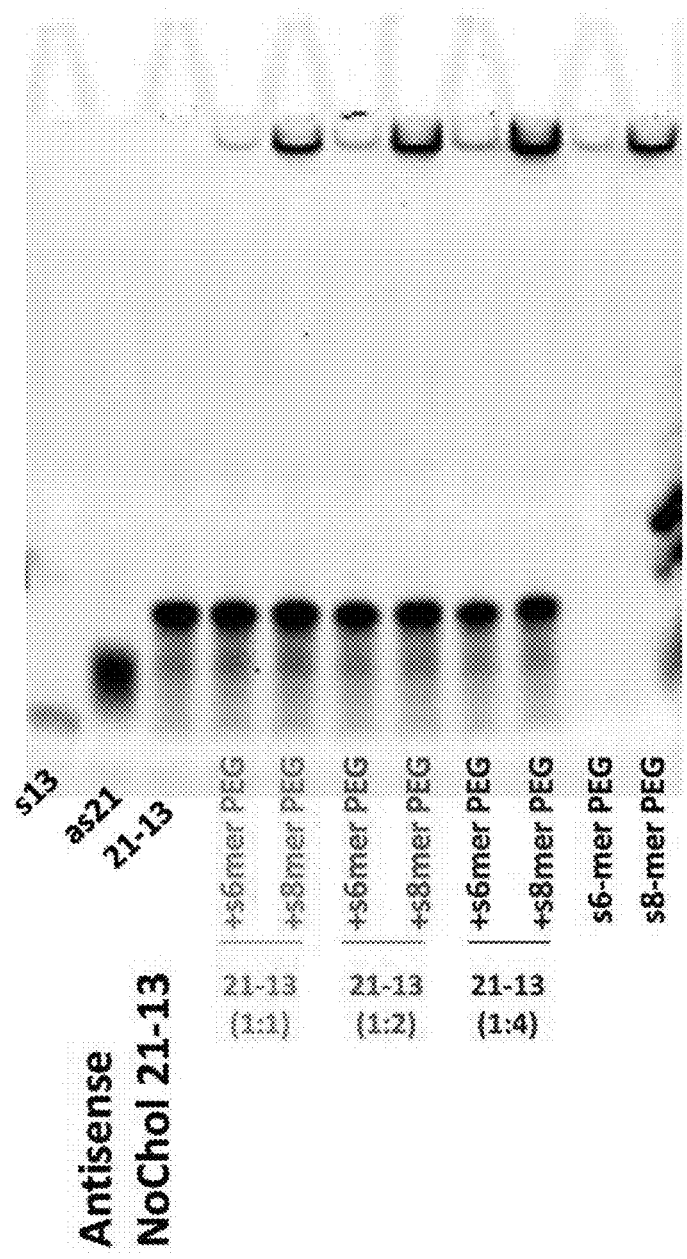
FIG. 42 depicts the results of a gel shift assay with an 8-nucleotide or 6-nucleotide PK-modifying anchor paired with a HTT-mRNA targeting asymmetric siRNA. The siRNA has a 21-nucleotide antisense strand and a 13-nucleotide sense strand. A 40 kDa PEG anchor was used. 1:1, 1:2, and 1:4 molar ratios of siRNA to anchor were used.

In the above recited sequences, "V" corresponds to a 5' vinylphosphonate moiety, "m" corresponds to a 2'-OMethyl modification, "f" corresponds to a 2'-Flouro modification, "#" corresponds to a phosphorothioate internucleotide linkage, "40k" corresponds to a 40 kDa PEG moiety, and the bold/underline portion of the antisense sequences correspond to the 8-nucleotide tail to which the PK-modifying anchors bind. As noted above, the sFlt-1 antisense strand tail and corresponding anchor have a G/C content of 87.5%, while the Htt antisense strand tail and corresponding anchor have a G/C content of 25%. As depicted in FIG. 42, there was no detectable shift of the siRNA in a gel-shift assay when using with the 6-nucleotide or 8-nucleotide anchor for the Htt siRNA. This was true at a 1:1, 1:2, and 1:4 molar ratio of siRNA to anchor. The results demonstrated that a G/C content poor tail sequence was insufficient to achieve binding of an anchor to a tail sequence.

Figure 43:
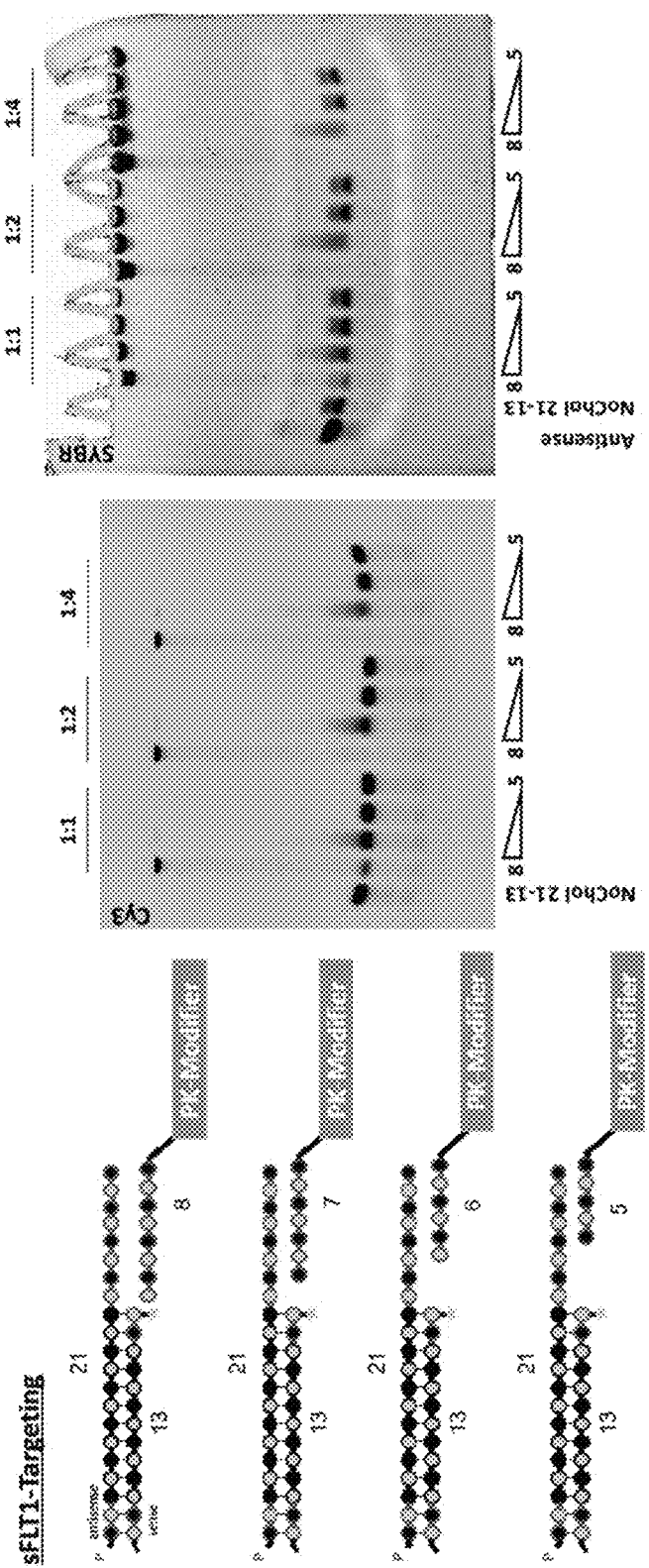
FIG. 43 depicts the results of a gel shift assay with an 8-nucleotide, 7-nucleotide, 6-nucleotide, or 5-nucleotide PK-modifying anchor paired with a sFlt-1 mRNA targeting asymmetric siRNA. The siRNA has a 21-nucleotide antisense strand and a 13-nucleotide sense strand. A 40 kDa PEG anchor was used. 1:1, 1:2, and 1:4 molar ratios of siRNA to anchor were used.
Figure 44:
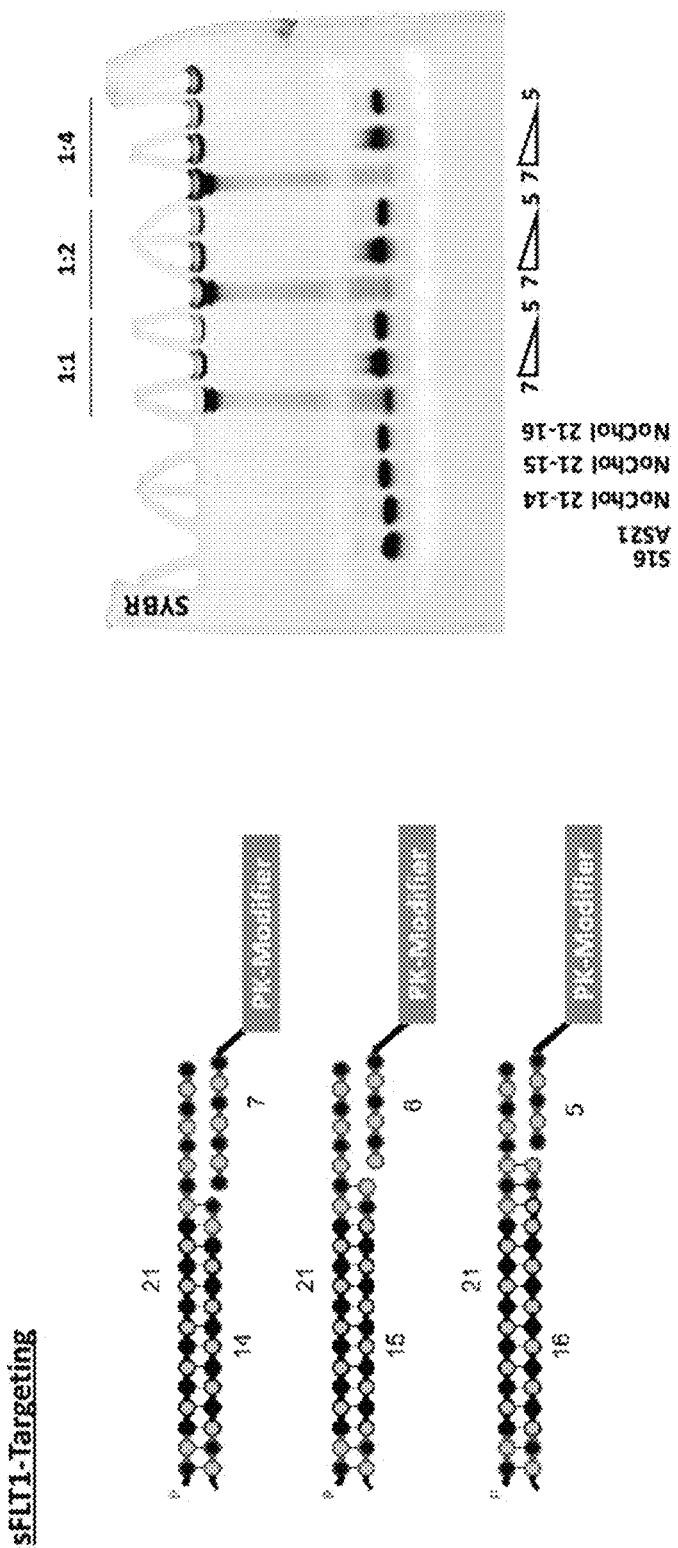
FIG. 44 depicts the results of a gel shift assay with a 7-nucleotide, 6-nucleotide, or 5-nucleotide PK-modifying anchor paired with a sFlt-1 mRNA targeting asymmetric siRNA. The siRNA has a 21-nucleotide antisense strand. The 7-nucleotide anchor was paired with a 14-nucleotide sense strand. The 6-nucleotide anchor was paired with a 15-nucleotide sense strand. The 5-nucleotide anchor was paired with a 16-nucleotide sense strand. A 40 kDa PEG anchor was used. 1:1, 1:2, and 1:4 molar ratios of siRNA to anchor were used.

In an effort to develop a conserved, universal anchor and antisense tail sequence, the length of the anchor and adjacent sense strand was altered to determine effect on anchor binding to the tail. As depicted in FIG. 43, a 21-13 siRNA was employed with an 8-nucleotide anchor, a 7-nucleotide anchor, a 6-nucleotide anchor, and a 5-nucleotide anchor. The 7-, 6-, and 5-nucleotide anchors each contain a gap in the sequence between the adjacent sense strand and the anchor (a 1-, 2-, and 3-nucleotide gap, respectively). When a gap is left within the sense strand and the oligonucleotide anchor, binding efficiency dropped due to the loss of the positive effects of coaxial stacking. A 7-nucleotide anchor required a four-fold molar amount to enable a complete shift in the gel electrophoresis assay. As depicted in FIG. 44, this reduced binding efficiency could be mitigated by increasing the length of the sense strand to close the gap between the sense strand and an anchor. A 7-nucleotide anchor, a 6-nucleotide anchor, and a 5-nucleotide anchor was used with a 14-nucleotide sense strand, a 15-nucleotide sense strand, and a 16-nucleotide sense strand, respectively. The gel-shift assay demonstrated that using a 14-nucleotide sense strand with a 7-nucleotide anchor mitigated the reduced binding efficiency compared to the 13-nucleotide sense strand/7-nucleotide anchor combination.

Figure 45:
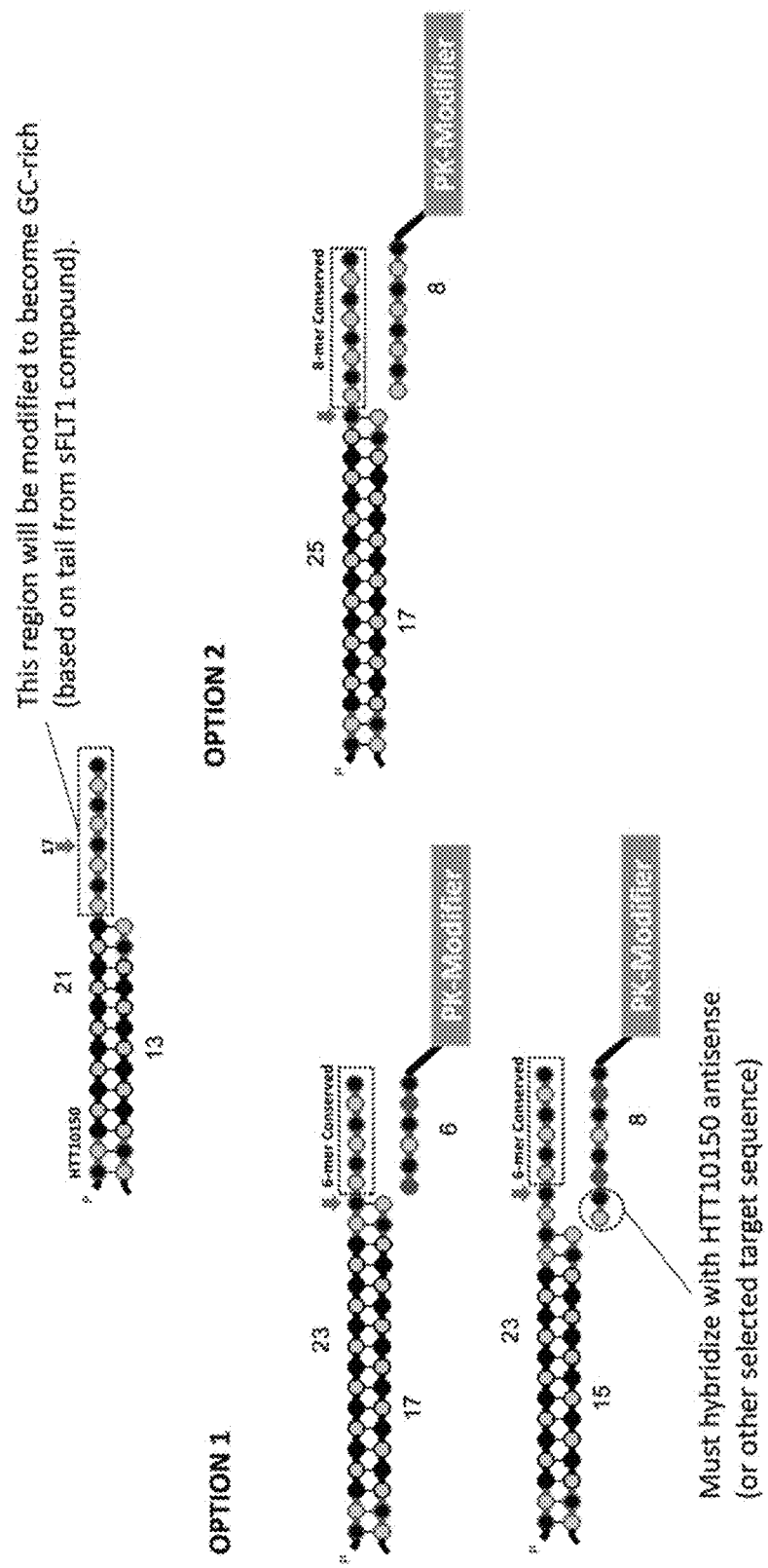
FIG. 45 schematically depicts the design of universal PK-modifying anchor sequences. Under Option 1, a 6-nucleotide universal sequence is engineered into the antisense strand, starting at nucleotide position 18 of a 23-nucleotide antisense strand. In a first instance under Option 1, a 17-nucleotide sense strand is used along with a 6-nucleotide anchor sequence that is complementary to the 6-nucleotide universal sequence on the antisense strand. In a second instance under Option 1, a 15-nucleotide sense strand is used along with an 8-nucleotide anchor sequence that is complementary to the 6-nucleotide universal sequence on the antisense strand with the other 2 nucleotides being complementary to nucleotides at positions 16 and 17 of the antisense strand, which will change depending on the target sequence selected for the antisense strand. Under Option 2, an 8-nucleotide universal sequence is engineered into the antisense strand, starting at nucleotide position 18 of a 25-nucleotide antisense strand. Under Option 2, a 17-nucleotide sense strand is used along with an 8-nucleotide anchor sequence that is complementary to the 8-nucleotide universal sequence on the antisense strand.

Several options were tested to design universal PK-modifying anchor sequences. Under Option 1, a 6-nucleotide universal sequence was engineered into the antisense strand, starting at nucleotide position 18 of a 23-nucleotide antisense strand. In a first instance under Option 1, a 17-nucleotide sense strand was used along with a 6-nucleotide anchor sequence that was complementary to the 6-nucleotide universal sequence on the antisense strand. In a second instance under Option 1, a 15-nucleotide sense strand was used along with an 8-nucleotide anchor sequence that was complementary to the 6-nucleotide universal sequence on the antisense strand with the other 2 nucleotides being complementary to nucleotides at positions 16 and 17 of the antisense strand, which will change depending on the target sequence selected for the antisense strand. Under Option 2, an 8-nucleotide universal sequence was engineered into the antisense strand, starting at nucleotide position 18 of a 25-nucleotide antisense strand. Under Option 2, a 17-nucleotide sense strand was used along with an 8-nucleotide anchor sequence that was complementary to the 8-nucleotide universal sequence on the antisense strand (FIG. 45).

Figure 46B:
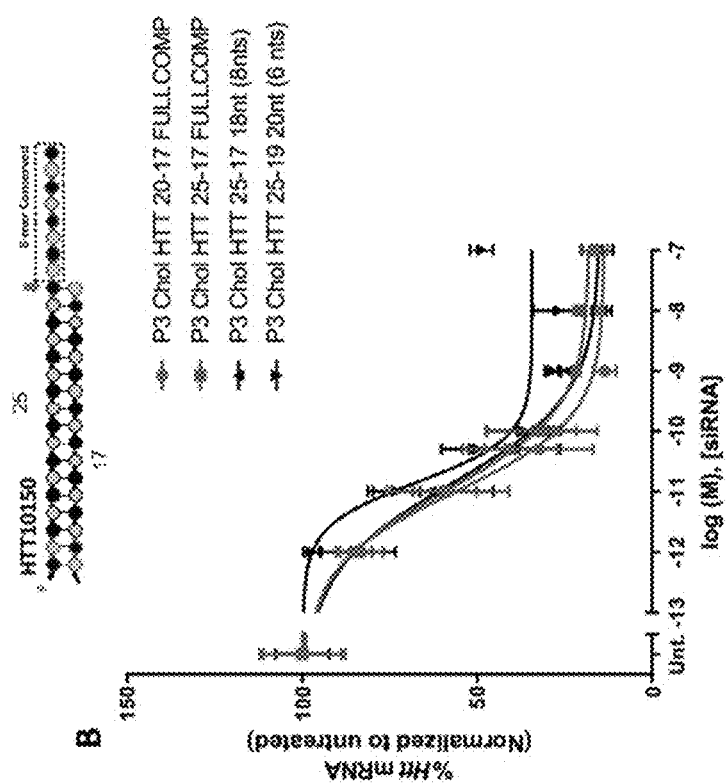
FIG. 46A-FIG. 46B depict the mRNA silencing efficacy of a target Htt mRNA. 23-nucleotide antisense strand sequences (FIG. 46A) and 25-nucleotide antisense strand sequences (FIG. 46B) were employed. Dose-responses were performed in Hela cells with a 72-hour incubation. A bDNA assay was used for mRNA assessment. Results were normalized to HPRT or PPIB.
Figure 46A:
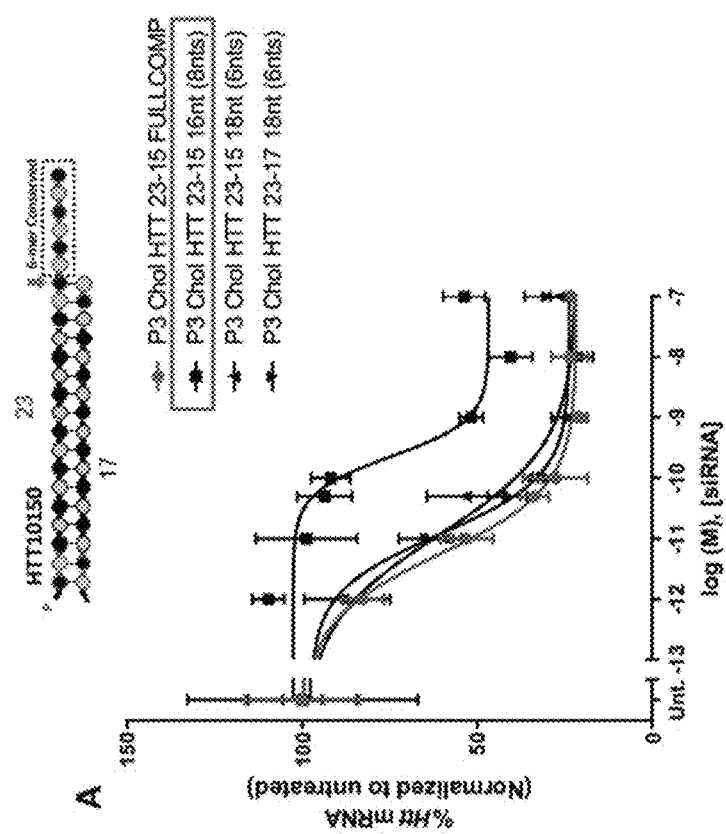

The three alternative universal PK-modifying anchor sequence approaches described above were tested against the Htt mRNA target. mRNA silencing efficacy of the target Htt mRNA was measured. Dose-responses were performed in Hela cells with a 72-hour incubation. A bDNA assay was used for mRNA assessment. Results were normalized to HPRT or PPIB. All 23-nucleotide based antisense sequences performed like the full complementary control except for the one where the conserved region was located from nucleotide 16 (FIG. 46A data point with box, "P3 Chol HTT 23-15 16nt (8 nts)"). Furthermore, all 25-nucleotide based antisense sequences performed like the full complementary control. The results demonstrate that the use of a conserved universal anchor sequence may be employed for any siRNA, thus overcoming any issues with a G/C content poor tail sequence (FIG. 46A-FIG. 46B).

In addition to the in vitro silencing experiments performed above, the effect of PK-modifying anchors with a conserved sequence on biodistribution was determined. The assay employed two different types of asymmetric siRNAs. The first was a sFlt-1 mRNA-targeting siRNA with a 21-nucleotide antisense strand, a 13-nucleotide sense strand, and an 8-nucleotide anchor (denoted 21-13-8). The second was a ApoE mRNA-targeting siRNA with a 25-nucleotide antisense strand, a 17-nucleotide sense strand, and an 8-nucleotide anchor (denoted 25-17-8). The 25-17-8 siRNA employed the conserved universal tail sequence described above, starting at position 18 of the antisense strand. Each siRNA had a GalNAc conjugate for liver delivery. The results demonstrated that the PK-modifying anchors with the conserved universal tail sequence also enhanced distribution to the liver compared to siRNAs without the conserved sequence, for both intravenous and subcutaneous delivery (FIG. 41).

The invention claimed is:

1. A method for treating a disease or a disorder in a patient in need thereof, comprising administering to the patient a compound comprising a first oligonucleotide, a second oligonucleotide, and a pharmacokinetic (PK)-modifying anchor, wherein:
   the first oligonucleotide is between 16 to 25 nucleotides in length, and comprises a 5' end, a 3' end, and complementarity to a target gene or a target mRNA;
   the second oligonucleotide is between 12 to 17 nucleotides in length, and comprises a 5' end and a 3' end; and
   the pharmacokinetic (PK)-modifying anchor comprises an anchor oligonucleotide between 5 to 8 nucleotides in length and comprising a 3' end and a 5' end, and at least one polymer conjugated to the 5' end, wherein the at least one polymer has a molecular weight between about 2,000 Da and about 40,000 Da, and wherein the at least one polymer is not a polypeptide,
   wherein a portion of the 5' end of the first oligonucleotide is complementary to the second oligonucleotide and a portion of the 3' end of the first oligonucleotide is complementary to the anchor oligonucleotide.

2. The method of claim 1, wherein the pharmacokinetic (PK)-modifying anchor further comprises a linker between the 5' end of the anchor oligonucleotide and the at least one polymer, the linker comprising an ethylene glycol chain, an alkyl chain, or a combination thereof.

3. The method of claim 1, wherein the first oligonucleotide comprises perfect complementarity to the target gene or the target mRNA.

4. The method of claim 1, wherein the at least one polymer is selected from the group consisting of a hydrophobic polycarbonate, a polyester, an amphiphilic block copolymer, a hydrophobic block copolymer, and a polysaccharide.

5. The method of claim 4, wherein:
   the hydrophobic polycarbonate is poly(DTR carbonate).

6. The method of claim 4, wherein the polyester is selected from the group consisting of a polyhydroxyalkanoate, a polycaprolactone, a poly(hyroxybuterate-hydroxyvalerate), a polyglycolic acid, and a polylactic acid.

7. The method of claim 4, wherein the amphiphilic block copolymer is selected from the group consisting of a polyvinylpyrrolidone, a poly(2-ethyl-2-oxazoline), an acrylonitrile styrene acrylate, an N-(2-hydroxypropyl) methacrylamide, and a polyethylene glycol (PEG).

8. The method of claim 4, wherein the hydrophobic block copolymer is selected from the group consisting of a poly (N,N-dimethylacrylamide), a poly(N,N-diethylaniline), a poly(diphenylamine), and a poly(tetrahydrofurfuryl methacrylate).

9. The method of claim 4, wherein the polysaccharide is selected from the group consisting of a soluble polyglucose, a non-soluble polyglucose, a cellulose, a glycogen, and an amylopectin.

10. The method of claim 1, wherein the PK-modifying anchor comprises more than one polymer.

11. The method of claim 10, wherein the PK-modifying anchor comprises 2, 3, or 4 polymers.

12. The method of claim 1, wherein the first oligonucleotide is fully chemically modified.

13. The method of claim 1, wherein:
the number of nucleotides in the first oligonucleotide is the same as the number of nucleotides in the second oligonucleotide and the anchor oligonucleotide combined.

14. The method of claim 1, wherein the anchor oligonucleotide consists of 8 nucleotides complementary to the 3' end of the first oligonucleotide.

15. The method of claim 1, wherein the first oligonucleotide is not conjugated at the 5' end or at the 3' end.

16. The method of claim 1, wherein the first oligonucleotide comprises a greater number of nucleotides than the second oligonucleotide and the anchor oligonucleotide combined.

17. The method of claim 1, wherein the first oligonucleotide comprises fewer nucleotides than in the second oligonucleotide and the anchor oligonucleotide combined.

18. A method of delivering a compound to the liver of a subject, comprising administering to the subject a compound comprising:
a first oligonucleotide, wherein the first oligonucleotide comprises 16 to 25 contiguous nucleotides, a 5' end, a 3' end, and complementarity to a target gene or target mRNA;
a second oligonucleotide comprising 12 to 17 contiguous nucleotides, a 5' end, and a 3' end, wherein a portion of the 5' end of the first oligonucleotide is complementary to a portion of the second oligonucleotide, and wherein the second oligonucleotide comprises an N-Acetylgalactosamine (GalNAc) moiety or a derivative thereof conjugated to the 3' end; and
a pharmacokinetic (PK)-modifying anchor comprising an anchor oligonucleotide comprising a 5' end, a 3' end, and at least one polymer conjugated to the 5' end, wherein the anchor oligonucleotide comprises about 5 to about 15 nucleotides that are complementary to the 3' end of the first oligonucleotide, and wherein the at least one polymer is at least about 2,000 Da.

19. A method for treating a disease or a disorder in a patient in need thereof, comprising administering to the patient a compound comprising a first oligonucleotide, a second oligonucleotide, and a pharmacokinetic (PK)-modifying anchor, wherein:
the first oligonucleotide is between 16 to 25 nucleotides in length, and comprises a 5' end, a 3' end, a complementarity to a target gene or target mRNA;
the second oligonucleotide is between 12 to 17 nucleotides in length, and comprises a 5' end and a 3' end; and
the pharmacokinetic (PK)-modifying anchor comprises an anchor oligonucleotide between 5 to 8 nucleotides in length and comprising a 3' end and a 5' end, and at least one polymer conjugated to the 5' end, wherein the at least one polymer is at least about 2,000 Da,
wherein a portion of the 5' end of the first oligonucleotide is complementary to the second oligonucleotide and a portion of the 3' end of the first oligonucleotide is complementary to the anchor oligonucleotide, and
wherein the second oligonucleotide further comprises conjugate moiety $X^c$ at the 3' end, at the 5' end, at an internal position, or a mixture thereof.

20. The method of claim 19,
wherein the second oligonucleotide is attached to $X^c$ with a linker L.

21. The method of claim 20, wherein L comprises an ethylene glycol chain, an alkyl chain, a peptide, RNA, DNA, a phosphodiester, a phosphorothioate, a phosphoramidate, an amide, a carbamate, or a combination thereof.

22. The method of claim 20, wherein $X^c$ is attached at the 3' end of the second oligonucleotide.

23. The method of claim 19, wherein $X^c$ is selected from the group consisting of a fatty acid, a steroid, a secosteroid, a lipid, a ganglioside, a nucleoside analog, and an endocannabinoid.

24. The method of claim 19, wherein $X^c$ comprises an N-Acetylgalactosamine (GalNAc) moiety or a derivative thereof.

25. The method of claim 19, wherein $X^c$ has an affinity for one or both of a low-density lipoprotein and an intermediate density lipoprotein.

26. The method of claim 19, wherein $X^c$ is a saturated or unsaturated moiety having fewer than three double bonds.

27. The method of claim 19, wherein $X^c$ has an affinity for high density lipoprotein.

28. The method of claim 19, wherein $X^c$ is a polyunsaturated moiety having three or more double bonds.

29. A method for treating a disease or a disorder in a patient in need thereof, comprising administering to the patient a compound comprising a first oligonucleotide, a second oligonucleotide, and a pharmacokinetic (PK)-modifying anchor, wherein:
the first oligonucleotide comprises a 5' end, a 3' end, and complementarity to a target gene or target mRNA;
the second oligonucleotide comprises a 5' end and a 3' end; and
the pharmacokinetic (PK)-modifying anchor comprises an anchor oligonucleotide comprising a 3' end and a 5' end, and at least one polymer conjugated to the 5' end, wherein the at least one polymer is at least about 2,000 Da,
wherein a portion of the 5' end of the first oligonucleotide is complementary to the second oligonucleotide and a portion of the 3' end of the first oligonucleotide is complementary to the anchor oligonucleotide, wherein:
a) the first oligonucleotide is between 21 nucleotides to 25 nucleotides in length;
b) the second oligonucleotide is between 13 nucleotides and 17 nucleotides in length; and
c) the anchor oligonucleotide is between 5 nucleotides and 8 nucleotides in length;
a) the first oligonucleotide is 21 nucleotides in length;
b) the second oligonucleotide is 13 nucleotides in length; and
c) the anchor oligonucleotide is 8 nucleotides in length;

a) the first oligonucleotide is 23 nucleotides in length;
b) the second oligonucleotide is 15 nucleotides in length; and
c) the anchor oligonucleotide is 8 nucleotides in length; or
a) the first oligonucleotide is 25 nucleotides in length;
b) the second oligonucleotide is 17 nucleotides in length; and
c) the anchor oligonucleotide is 8 nucleotides in length.

30. A method for treating a disease or a disorder in a patient in need thereof, comprising administering to the patient:
   a first oligonucleotide, wherein the first oligonucleotide is 21 nucleotides in length, with a 5' end and a 3' end, and is complementary to a target gene or a target mRNA;
   a second oligonucleotide, wherein the second oligonucleotide is 13 nucleotides in length, with a 5' end and a 3' end, and is complementary to nucleotides 1-13 of the first oligonucleotide; and
   an anchor oligonucleotide, wherein the anchor oligonucleotide is 8 nucleotides in length, with a 5' end, a 3' end, and is complementary nucleotides 14-21 of the first oligonucleotide,
   wherein the second oligonucleotide is attached to a molecule comprising a cholesterol, a docosanoic acid, a docosahexaenoic acid, or an N-acetylgalactosamine at the 3' end,
   wherein the anchor oligonucleotide is attached to a polyethylene glycol polymer comprising a molecular weight of between 10,000 and 40,000 Daltons at the 5' end,
   wherein the first oligonucleotide comprises complementarity to both the second oligonucleotide and the anchor oligonucleotide to form a duplex, and wherein the 5' end of the second oligonucleotide is not connected to the 3' end of the anchor oligonucleotide.

31. A method for treating a disease or a disorder in a patient in need thereof, comprising administering to the patient:
   an oligonucleotide duplex comprising a first oligonucleotide, wherein the first oligonucleotide is 25 nucleotides in length, with a 5' end and a 3' end, and comprises complementarity to a target gene or a target mRNA;
   a second oligonucleotide, wherein the second oligonucleotide is 17 nucleotides in length, with a 5' end and a 3' end, is hydrophobically modified, and is complementary to nucleotides 1-17 of the first oligonucleotide; and
   an anchor oligonucleotide, wherein the anchor oligonucleotide is 8 nucleotides in length, with a 5' end and a 3' end, and is complementarity to nucleotides 18-25 of the first oligonucleotide, wherein the anchor oligonucleotide comprises a pharmacokinetic-modifying moiety.

32. A method for treating a disease or a disorder in a patient in need thereof, comprising administering to the patient an siRNA duplex comprising:
   a first RNA strand between 21 nucleotides and 25 nucleotides in length and comprising complementarity to a target gene or a target mRNA;
   a second RNA strand between 13 nucleotides and 17 nucleotides in length and having homology with a target sequence; and
   an anchor oligonucleotide strand between 5 nucleotides and 8 nucleotides in length, wherein the anchor oligonucleotide strand comprises a polymeric pharmacokinetic-modifying moiety selected from the group consisting of a hydrophilic polycarbonate, a polyethylene glycol (PEG), a block co-polymer, a poloxamer, a polysaccharide, and a poly(lactic-co-glycolic acid) (PLGA),
   wherein the first RNA strand can pair with the second RNA strand to form an asymmetric siRNA, and the anchor oligonucleotide strand binds to a single stranded region of the siRNA.

* * * * *